(12) United States Patent
Reitz et al.

(10) Patent No.: US 11,358,935 B2
(45) Date of Patent: Jun. 14, 2022

(54) PRODRUGS OF LANICEMINE AND THEIR METHOD OF USE

(71) Applicant: Biohaven Pharmaceutical Holding Company Ltd., New Haven, CT (US)

(72) Inventors: Allen B. Reitz, Lansdale, PA (US); Jeffery Claude Pelletier, Lafayette Hill, PA (US)

(73) Assignee: Biohaven Pharmaceutical Holding Company Ltd., New Haven, CT (US)

( * ) Notice: Subject to any disclaimer, the term of this patent is extended or adjusted under 35 U.S.C. 154(b) by 43 days.

(21) Appl. No.: 16/464,008

(22) PCT Filed: Nov. 22, 2017

(86) PCT No.: PCT/US2017/063098
§ 371 (c)(1),
(2) Date: May 24, 2019

(87) PCT Pub. No.: WO2018/098344
PCT Pub. Date: May 31, 2018

(65) Prior Publication Data
US 2020/0299238 A1 Sep. 24, 2020

Related U.S. Application Data

(60) Provisional application No. 62/426,924, filed on Nov. 28, 2016.

(51) Int. Cl.
*C07D 213/40* (2006.01)
(52) U.S. Cl.
CPC .................. *C07D 213/40* (2013.01)

(58) Field of Classification Search
CPC .................................................... C07D 213/40
See application file for complete search history.

(56) References Cited

U.S. PATENT DOCUMENTS

| | | | |
|---|---|---|---|
| 4,769,466 A | 9/1988 | Griffith et al. | |
| 5,607,935 A | 3/1997 | Griffith et al. | |
| 2007/0270498 A1 | 11/2007 | Chow et al. | |
| 2016/0280647 A1 | 9/2016 | Nordvall et al. | |

FOREIGN PATENT DOCUMENTS

WO 2016/025721 A1 2/2016

OTHER PUBLICATIONS

Harikrishnan, J Med Chem, 2012, vol. 55, 6162-6175., (Year: 2012).*
Shuman, Am Chem Soc, vol. 27, 1962, 1970-1972. (Year: 1962).*
International Search Report issued in corresponding PCT Patent Application No. PCT/US2017/063098, dated Mar. 19, 2018.

* cited by examiner

*Primary Examiner* — D Margaret M Seaman
(74) *Attorney, Agent, or Firm* — Locke Lord LLP; Ralph A. Loren; Nicholas J. DiCeglie, Jr.

(57) ABSTRACT

Pharmaceutical compositions of the invention include substituted Lanicemine prodrugs useful for the treatment of conditions associated with dysregulation of NMDA receptor activity such as depression and depressive disorders through the release of Lanicemine, Prodrugs of Lanicemine have enhanced stability to hepatic metabolism and are delivered into systemic circulation by oral administration, and then cleaved to release Lanicemine in the plasma via either an enzymatic or general biophysical release process.

32 Claims, No Drawings

PRODRUGS OF LANICEMINE AND THEIR METHOD OF USE

CROSS REFERENCE TO RELATED APPLICATIONS

This application is a 35 U.S.C. § 371 National Phase Application of International PCT Patent Application No. PCT/US2017/063098 filed on Nov. 22, 2017, which application claims the benefit of priority to U.S. Provisional Patent Application No. 62/426,924 filed on Nov. 28, 2016. The entire contents of these applications are incorporated herein by reference in their entireties.

FIELD OF INVENTION

The present invention describes compounds and methods useful as prodrug agents, useful for the treatment of diseases and conditions associated with the N-methyl-D-aspartate receptor (NMDA receptor).

BACKGROUND OF THE INVENTION

The N-methyl-D-aspartate receptor (NMDA receptor) is an ion channel and glutamate receptor found in nerve cells. The NMDA receptor is activated by glutamate, glycine or D-serine, and once activated, it allows passage of positively charged ion through the cell membrane (Furukawa, H.; Singh, S. K; Mancusso, R.; Gouaux, E. Nature, 2005, 438, 7065, 185-192.). It has been demonstrated that NMDA receptor activity is critical to synaptic plasticity (Scatton B. Fundamental and clinical pharmacology, 1993, 7, 8, 389-400) and that this receptor plays a role in the pathology of a number of diseases and conditions. Depression, depressive disorder, and major depressive disorder (MDD) are associated with the NMDA receptor. Current estimates indicate that over 121 million people across the globe suffer from MDD alone. Overall, the treatment of depression, depressive disorder, and major depressive disorder (MDD) is inadequate to meet the needs of patients (Reus, G. Z; Abelaira, H. M; Tuon, T.; Ignacio, Z. M; Titus, S. E; Rodrigues, A. L. S.; Quevedo, J. Advances in protein chemistry and structural biology, 2016, 103, 169-202.). There is a clear and compelling need to identify novel therapies for the treatment of depression, depressive disorder, and major depressive disorder (MDD).

Separately, it has been established that the NMDA receptor plays a role in pain, including neuropathic pain (Bennett, G. J. Journal of pain and symptom management, 2000, 19, S1, S2-6.) and that suppression of NMDA receptor activity can suppress pain sensation, including neuropathic pain (Elliott, K.; Kest, B.; Man, A.; Kao, B.; Inturrisi, C. E. Neuropsychopharmacology, 1995, 13, 4, 347-356). Pain, including neuropathic pain remains a major medical needs and there is a clear and compelling need to develop novel therapies for the treatment of pain, including neuropathic pain.

The NMDA receptor has also been shown to play a role on a number of additional diseases and conditions including but not limited to Rett Syndrome (Patrizi, A.; Picard, N. Simon, A. J.; Gunner, G.; Centofante, E.; Andrews, N. A.; Fagiolini, M. Biological Psychiatry, 2016, 79, 9, 755-764), suicidal ideation (Rajkumar, R.; Famn, J.; Yeo, E. Y. M.; Dawe, G. S. Pharmacological Research, 2015, 99, 23-35), bipolar disorder, bipolar depression, (Iadarola, N. D.; Niciu, M. J.; Richards, E. M.; Vande Voort, J. L.; Ballard, E. D.; Lundin, N. B.; Nugent, A. C.; Machado-Vieira, R.; Zarate, C. A., Jr. Therapeutic Advances in Chronic Disease, 2015, 6, 3, 97-114), obsessive compulsive disorder (Wu, P. L.; Lane, H. Y.; Tang, H. S.; Tsai, G. E. BioMedicine, 2012, 2, 2, 75-79), status epilepticus (Zeiler, F. A.; Teitelbaum, L; Gillman, L. M.; West, M. Neurocritical Care, 2014, 20, 3, 502-513), and sarin gas poisoning (Weissman, B. A.; Raveh, L. Toxicology and Applied Pharmacology, 2008, 232, 2, 351-358). Rett Syndrome, suicidal ideation, bipolar disorder, bipolar depression, obsessive compulsive disorder, status epilepticus, and sarin gas poisoning are all difficult to treat or poorly treated with current therapies. There is a clear and pressing need for additional therapies and for Rett Syndrome, suicidal ideation, bipolar disorder, bipolar depression, obsessive compulsive disorder, status epilepticus, and sarin gas poisoning.

BRIEF SUMMARY OF THE INVENTION

The present invention is directed toward lanicemine derivatives of formula (I),

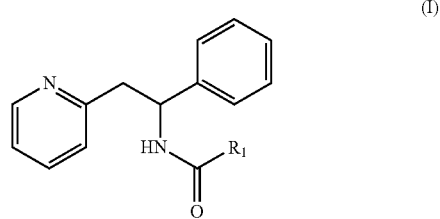

including enantiomers, diastereomers, hydrates, solvates, pharmaceutically acceptable salts, and complexes thereof, wherein:

$R^1$ is selected from the group consisting of $C_1$-$C_6$ fluoroalkyl, $OR^2$, $(CR^{6a}R^{6b})_m NHR^7$,

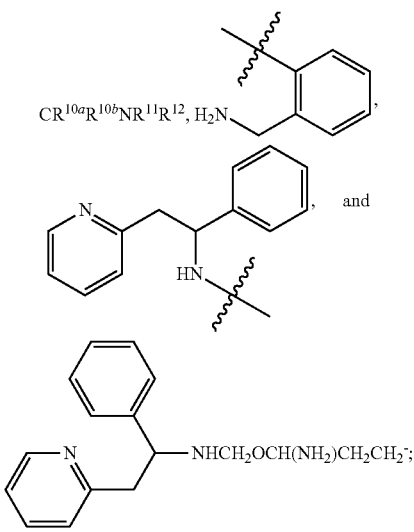

$R^2$ is selected from the group consisting of $CH_2(CH_2)_n NR^{3a}R^{3b}$,

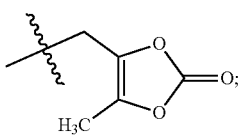

$R^{3a}$ and $R^{3b}$ are independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, and $CO_2R^4$;

$R^{3a}$ and $R^{3b}$ cannot both be $C_1$-$C_6$ alkyl;

$R^{3a}$ and $R^{3b}$ are taken together with the atom to which they are bound to form an optionally substituted three to six membered saturated heterocyclic ring consisting of two to five carbon atoms and a member selected from the group consisting of O, $NR^5$, S, and $SO_2$;

n is 1 or 2;

$R^4$ is selected from the group consisting of $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted phenyl, and optionally substituted benzyl;

$R^5$ is selected from the group consisting of $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{6a}$ and $R^{6b}$ are at each occurrence independently selected from the group consisting of hydrogen, optionally substituted $C_1$-$C_6$ alkyl, optionally substituted $C_3$-$C_7$ branched alkyl, optionally substituted $C_3$-$C_7$ cycloalkyl, $C_2$-$C_6$ alkenyl, and $C_2$-$C_6$ alkynyl;

$R^{6a}$ and $R^{6b}$ are taken together with the atom to which they are bound to form an optionally substituted 6 membered ring;

m is 1, 2, or 3;

$R^7$ is selected from the group consisting of $COCR^{8a}R^{8b}(NHR^9)$,

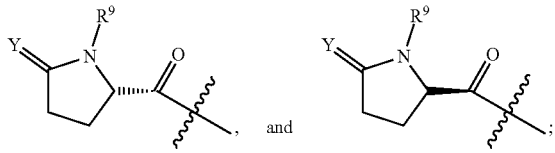

$R^{8a}$ and $R^{8b}$ are at each occurrence independently selected from the group consisting of hydrogen, $CH_3$, $CH(CH_3)_2$, $CH_2CH(CH_3)_2$, $CH(CH_3)CH_2CH_3$, $CH_2OH$, $CH(OH)CH_3$, $CH_2Ph$, $CH_2$(4-OH-Ph), $(CH_2)_4NH_2$, $(CH_2)_3NHC(NH_2)NH$, $C_2$(3-indole), $CH_2$(5-imidazole), $CH_2CO_2H$, $CH_2CH_2CO_2H$, $CH_2CONH_2$, and $CH_2CH_2CONH_2$;

$R^9$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

Y is at each occurrence independently selected from the group consisting of $H_2$ or O;

$R^{10a}$ and $R^{10b}$ are at each occurrence independently selected from the group consisting of hydrogen, $CH_3$, $CH_2CH_3$, $CH(CH_3)_2$, $CH_2CH(CH_3)_2$, $CH(CH_3)CH_2CH_3$, $CH_2OH$, $CH_2OCH_2Ph$, $CH(OH)CH_3$, $CH_2Ph$, $CH_2$(4-OH-Ph), $(CH_2)_4NH_2$, $(CH_2)NHC(NH_2)NH$, $CH_2$(3-indole), $CH_2$(5-imidazole), $CH_2$(CCH), $CH_2$(cyclohexyl), $CH_2CO_2H$, $CH_2CH_2CO_2H$, $CH_2CONH_2$, and $CH_2CH_2CONH_2$;

$R^{10a}$ and $R^{10b}$ are taken together with the atom to which they are bound to form an optionally substituted three to six membered saturated carbocyclic ring;

$R^{11}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_1$-$C_6$ haloalkyl, and $C_2$-$C_6$ alkynyl:

$R^{12}$ is at each occurrence independently selected from the group consisting of hydrogen, $C_1$-$C_6$ alkyl, $COCR^{13a}R^{13b}NR^{15a}R^{15b}$, $COCR^{13a}R^{13b}OR^{14}$, $SO_2CR^{13a}R^{13b}NR^{15a}R^{15b}$, $COCR^{13a}R^{15b}NHSO_2R^{15a}$,

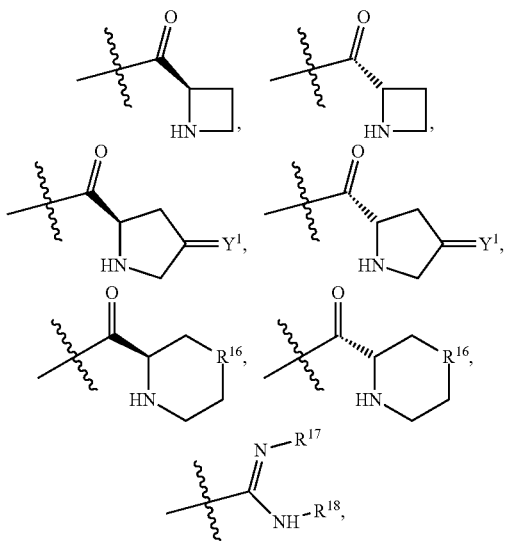

and $(CR^{19a}R^{19b})_qNHR^{20}$, and when $R^{12}$ is hydrogen, $R^{11}$ cannot be hydrogen;

$R^{11}$ and $R^{12}$ are taken together with the atom to which they are bound to form an optionally substituted four to six membered saturated heterocyclic ring containing a nitrogen atom and optionally containing an additional heteroatom from the group consisting of N and O;

$R^{13a}$ and $R^{13b}$ are at each occurrence independently selected from the group consisting hydrogen, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$;

$R^{13a}$ and $R^{13b}$ are taken together with the atom to which they are bound to form an optionally substituted three to six membered saturated carbocyclic ring;

$R^{13a}$ and $R^{13b}$ are taken together with the atom to which they are bound to form an optionally substituted six membered saturated heterocyclic ring with one O atom within the ring;

$R^{13a}$ and $R^{14}$ are taken together with the atoms to which they are bound to form an optionally substituted four to six membered ring containing one nitrogen atom;

$R^{13a}$ and $R^{15a}$ are taken together with the atoms to which they are bound to form an optionally substituted four to six membered ring containing one nitrogen atom;

$Y^1$ is at each occurrence independently selected from the group consisting of $H_1$, O, and —H/—$OCH_2Ph$;

$R^{14}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{15a}$ and $R^{15b}$ are at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl $C_1$-$C_6$ fluoroalkyl, $COR^{21}$, $CH_2R^{21}$, $SO_2R^{22}$, an optionally substituted four to six membered saturated heterocyclic ring containing a heteroatom selected from the group consisting of $NR^{24}$ and O, $COCHR^{23}NH_2$,

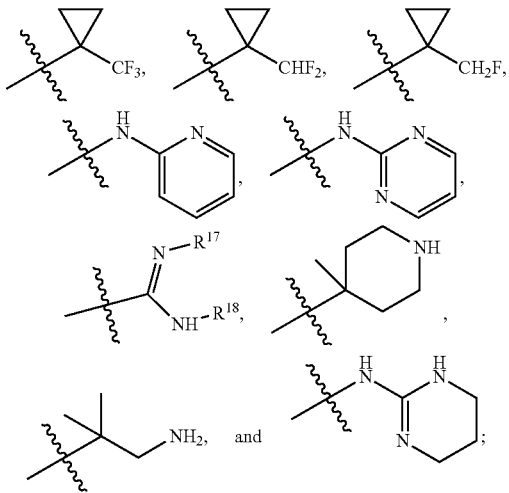

$R^{15a}$ and $R^{15b}$ are taken together with the atom to which they are bound to form an optionally substituted three to six membered saturated heterocyclic ring consisting of two to five carbon atoms and a member selected from the group consisting of O, $NR^5$, S, and $SO_2$;
$R^{16}$ is at each occurrence independently selected from the group consisting of $CH_2$, O, C=O, and NH;
$R^{17}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;
$R^{18}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;
$R^{17}$ and $R^{18}$ are taken together with the atoms to which they are bound to form an optionally substituted five or six membered ring containing two nitrogen atoms;
$R^{19a}$ and $R^{19b}$ are at each occurrence independently selected from the group consisting of hydrogen, optionally substituted $C_1$-$C_6$, alkyl, optionally substituted $C_3$-$C_7$ branched alkyl, optionally substituted $C_3$-$C_7$ cycloalkyl, optionally substituted $C_2$-$C_6$ alkenyl, and optionally substituted $C_2$-$C_6$ alkynyl;
$R^{19a}$ and $R^{19b}$ are taken together with the atom to which they are bound to form an optionally substituted 3 to 6 membered carbocyclic ring;
$R^{20}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;
q is 1, or 2;
$R^{21}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, $C_1$-$C_6$ fluoroalkyl, optionally substituted aryl, and optionally substituted heteroaryl;
$R^{22}$ is at each occurrence independently selected from the group consisting of $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted aryl, optionally substituted heteroaryl;
$R^{23}$ is selected from the group consisting H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$;
$R^{24}$ is at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted aryl, optionally substituted heteroaryl, $COR^{25}$, and $SO_2$—$C_{1-6}$alkyl;
$R^{25}$ is at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted aryl, optionally substituted heteroaryl, $C_1$-$C_6$ alkoxy, and $C_1$-$C_6$ alkylamino.

The compounds of the present invention include compounds having formula (II):

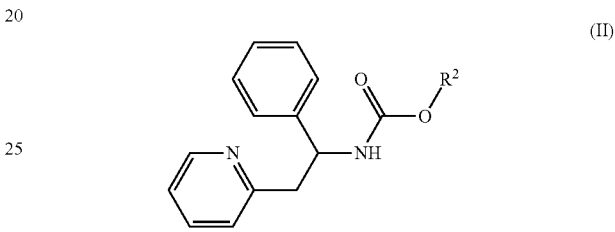

including enantiomers, diastereomers, hydrates, solvates, pharmaceutically acceptable salts, and complexes thereof.

The compounds of the present invention include compounds having formula (II):

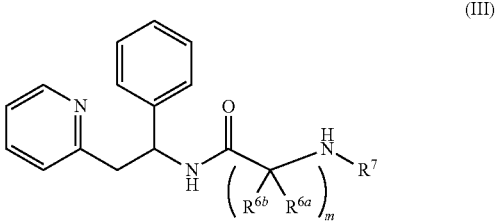

including enantiomers, diastereomers, hydrates, solvates, pharmaceutically acceptable salts, and complexes thereof.

The compounds of the present invention include compounds having formula (IV):

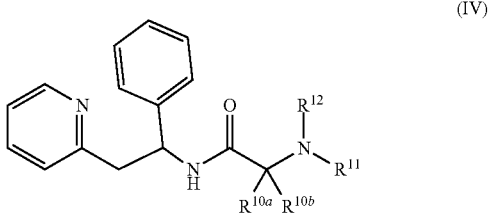

including enantiomers, diastereomers, hydrates, solvates, pharmaceutically acceptable salts, and complexes thereof.

The compounds of the present invention include compounds having formula (V):

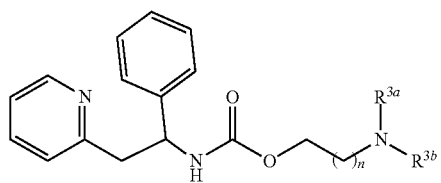
(V)

including enantiomers, diastereomers, hydrates, solvates, pharmaceutically acceptable salts, and complexes thereof.

The compounds of the present invention include compounds having formula (VI):

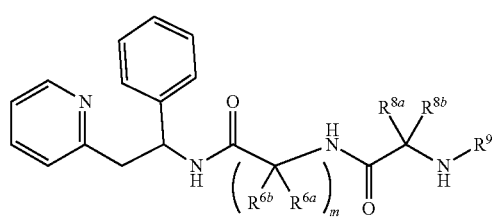
(VI)

including enantiomers, diastereomers, hydrates, solvates, pharmaceutically acceptable salts, and complexes thereof.

The compounds of the present invention include compounds having formula (VII):

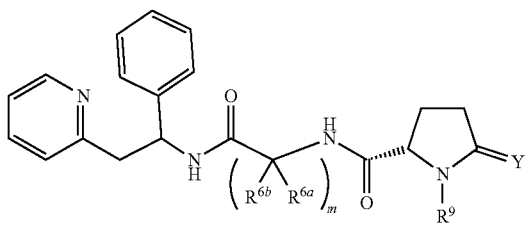
(VII)

including enantiomers, diastereomers, hydrates, solvates, pharmaceutically acceptable salts, and complexes thereof.

The compounds of the present invention include compounds having formula (VIII):

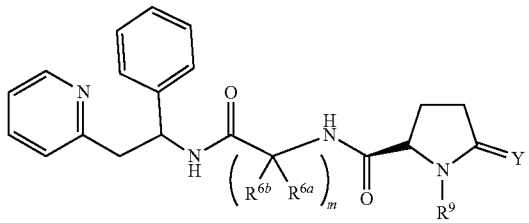
(VIII)

including enantiomers, diastereomers, hydrates, solvates, pharmaceutically acceptable salts, and complexes thereof.

The compounds of the present invention include compounds having formula (IX):

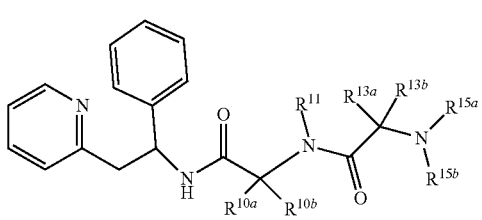
(IX)

including enantiomers, diastereomers, hydrates, solvates, pharmaceutically acceptable salts, and complexes thereof.

The compounds of the present invention include compounds having formula (X):

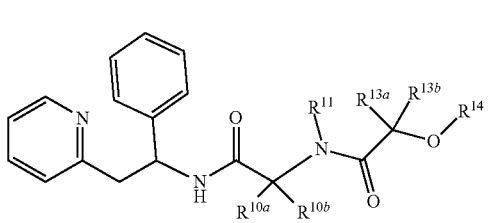
(X)

including enantiomers, diastereomers, hydrates, solvates, pharmaceutically acceptable salts, and complexes thereof.

The compounds of the present invention include compounds having formula (XI):

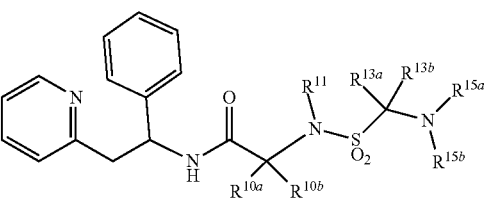
(XI)

including enantiomers, diastereomers, hydrates, solvates, pharmaceutically acceptable salts, and complexes thereof.

The compounds of the present invention include compounds having formula (XII):

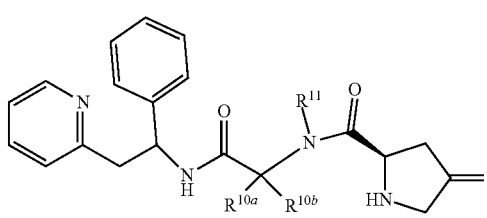
(XII)

including enantiomers, diastereomers, hydrates, solvates, pharmaceutically acceptable salts, and complexes thereof.

The compounds of the present invention include compounds having formula (XIII):

(XIII)

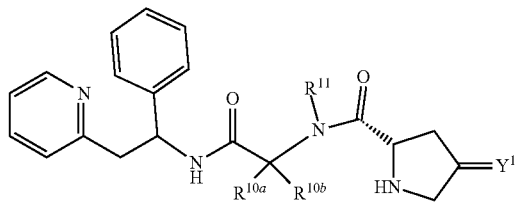

including enantiomers, diastereomers, hydrates, solvates, pharmaceutically acceptable salts, and complexes thereof.

The compounds of the present invention include compounds having formula (XIV):

(XIV)

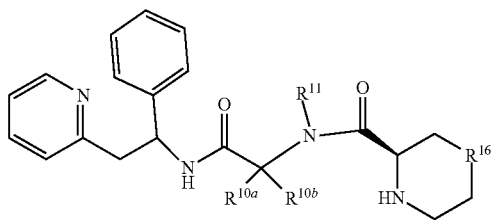

including enantiomers, diastereomers, hydrates, solvates, pharmaceutically acceptable salts, and complexes thereof.

The compounds of the present invention include compounds having formula (XV):

(XV)

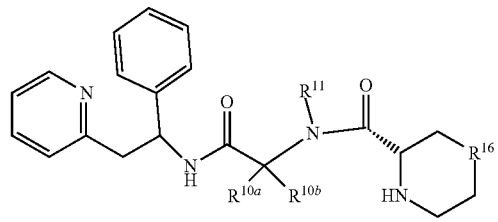

including enantiomers, diastereomers, hydrates, solvates, pharmaceutically acceptable salts, and complexes thereof.

The compounds of the present invention include compounds having formula (XVI):

(XVI)

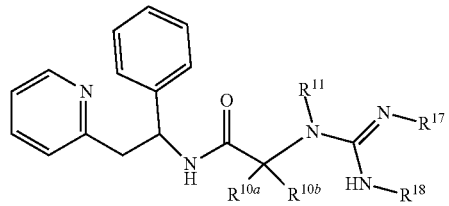

including enantiomers, diastereomers, hydrates, solvates, pharmaceutically acceptable salts, and complexes thereof.

The compounds of the present invention include compounds having formula (XVII):

(XVII)

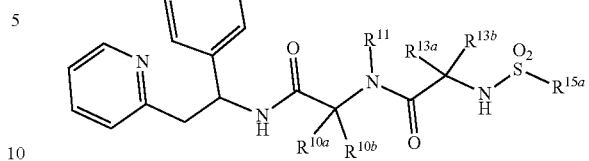

including enantiomers, diastereomers, hydrates, solvates, pharmaceutically acceptable salts, and complexes thereof.

The present invention further relates to compositions comprising:

an effective amount of one or more compounds according to the present invention and an excipient.

The present invention also relates to a method for treating or preventing depression and depressive disorders, said method comprising administering to a subject an effective amount of a compound or composition according to the present invention.

The present invention yet further relates to a method for treating or preventing depression and depressive disorders, wherein said method comprises administering to a subject a composition comprising an effective amount of one or more compounds according to the present invention and an excipient.

The present invention also relates to a method for treating or preventing disease or conditions associated with depression and depressive disorders. Said methods comprise administering to a subject an effective amount of a compound or composition according to the present invention.

The present invention yet further relates to a method for treating or preventing disease or conditions associated with depression and depressive disorders, wherein said method comprises administering to a subject a composition comprising an effective amount of one or more compounds according to the present invention and an excipient.

The present invention also relates to a method for treating or preventing major depressive disorder (MDD), said method comprising administering to a subject an effective amount of a compound or composition according to the present invention.

The present invention yet further relates to a method for treating or preventing major depressive disorder (MDD), wherein said method comprises administering to a subject a composition comprising an effective amount of one or more compounds according to the present invention and an excipient.

The present invention also relates to a method for treating or preventing diseases and conditions associated with major depressive disorder (MDD). Said methods comprise administering to a subject an effective amount of a compound or composition according to the present invention.

The present invention yet further relates to a method for treating or preventing diseases and conditions associated with major depressive disorder (MDD), wherein said method comprises administering to a subject a composition comprising an effective amount of one or more compounds according to the present invention and an excipient.

The present invention also relates to a method for treating or preventing pain, said method comprising administering to a subject an effective amount of a compound or composition according to the present invention.

The present invention yet further relates to a method for treating or preventing pain, wherein said method comprises administering to a subject a composition comprising an effective amount of one or more compounds according to the present invention and an excipient.

The present invention also relates to a method for treating or preventing diseases and conditions associated with pain. Said methods comprise administering to a subject an effective amount of a compound or composition according to the present invention.

The present invention yet further relates to a method for treating or preventing diseases and conditions associated with pain, wherein said method comprises administering to a subject a composition comprising an effective amount of one or more compounds according to the present invention and an excipient.

The present invention also relates to a method for treating or preventing neuropathic pain, said method comprising administering to a subject an effective amount of a compound or composition according to the present invention.

The present invention yet further relates to a method for treating or preventing neuropathic pain, wherein said method comprises administering to a subject a composition comprising an effective amount of one or more compounds according to the present invention and an excipient.

The present invention also relates to a method for treating or preventing diseases and conditions associated with neuropathic pain. Said methods comprise administering to a subject an effective amount of a compound or composition according to the present invention.

The present invention yet further relates to a method for treating or preventing diseases and conditions associated with neuropathic pain, wherein said method comprises administering to a subject a composition comprising an effective amount of one or more compounds according to the present invention and an excipient.

The present invention also relates to a method for treating or preventing diseases and conditions associated with dysregulation of NMDA receptor activity such as Rett Syndrome, suicidal ideation, bipolar disorder, bipolar depression, obsessive compulsive disorder, sarin gas poisoning, and status epilepticus, said method comprising administering to a subject an effective amount of a compound or composition according to the present invention.

The present invention yet further relates to a method for treating or preventing diseases and conditions associated with dysregulation of NMDA receptor activity such as Rett Syndrome, suicidal ideation, bipolar disorder, bipolar depression, obsessive compulsive disorder, sarin gas poisoning, and status epilepticus, wherein said method comprises administering to a subject a composition comprising an effective amount of one or more compounds according to the present invention and an excipient.

The present invention further relates to a process for preparing the Lanicemine prodrugs of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The prodrugs of the present invention are capable of treating and preventing diseases associated with dysregulation of NMDA receptor activity such as depression and depressive disorders by releasing Lanicemine in vivo. Prodrugs of Lanicemine have enhanced stability to hepatic metabolism and are delivered into systemic circulation by oral administration, and are then cleaved to release Lanicemine in the plasma via either an enzymatic or general biophysical release process. The pro-drugs of the present invention are also capable of treating and preventing other disease states and conditions in which NMDA receptor activity is dysregulated. Disease states and conditions in which NMDA receptor activity is dysregulated include, but are not limited to major depressive disorder (MDD), pain, neuropathic pain, Rett Syndrome, suicidal ideation, bipolar disorder, bipolar depression, obsessive compulsive disorder, sarin gas poisoning, and status epilepticus.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_1$-$C_6$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as ($C_1$-$C_6$alkyl)$_2$amino, the alkyl groups may be the same or different.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo [3.1.1]heptanyl, 1,3-dimethyl[2.2.1]heptan-2-yl, bicyclo [2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., $-CF_3$, $CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term v cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein, Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocyclyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiophenyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 71H-pyrrolo[2,3-d]pyrimidinyl, pyrido[2,3-d]pyrimidinyl, benzo [d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

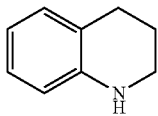

is, for the purposes of the present invention, considered a heterocyclic unit. 6,7-Dihydro-5H-cyclopentapyrimidine having the formula:

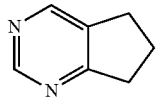

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

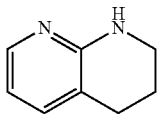

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^{26}$, —SR$^{26}$, —N(R$^{26}$)$_2$, —N$^{26}$C(O)R$^{26}$, —SO$_2$R$^{26}$, —SO$_2$OR$^{26}$, —SO$_2$N(R$^{26}$)$_2$, —C(O)R$^{26}$, —C(O)OR$^{26}$, —C(O)N(R$^{26}$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^{26}$; wherein R$^{26}$, at each occurrence, independently is hydrogen, —OR$^{27}$, —SR$^{27}$, —C(O)R$^{27}$, —C(O)OR$^{27}$, —C(O)N (R$^{27}$)$_2$, —SO$_2$R$^{27}$, —S(O)$_2$OR$^{27}$, —N(R$^{27}$)$_2$, —NR$^{27}$C(O) R$^{27}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{26}$ units taken together with the atom(s) to which they are bound form an optionally substituted carbocycle or heterocycle wherein said carbocycle or heterocycle has 3 to 7 ring atoms; wherein R$^{27}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{27}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) OR$^{28}$; for example, —OH, —OCH$_3$, —OCH$_2$CH$_3$, —OCH$_2$CH$_2$CH$_3$;
ii) —C(O)R$^{28}$; for example, —COCH$_3$, —COCH$_2$CH$_3$, —COCH$_2$CH$_2$CH$_3$;
iii) —C(O)OR$^{28}$; for example, —CO$_2$CH$_3$, —CO$_2$CH$_2$CH$_3$, —CO$_2$CH$_2$CH$_2$CH$_3$;
iv) —C(O)N(R$^{28}$)$_2$; for example, —CONH$_2$, —CONHCH$_3$, —CON(CH$_3$)$_2$;
v) —N(R$^{28}$)$_2$; for example, —NH$_2$, —NHCH$_3$, —N(CH$_3$)$_2$, —NH(CH$_2$CH$_3$);
vi) halogen: —F, —Cl, —Br, and —I;
vii) —CH$_e$X$_g$; wherein X is halogen, n is from 0 to 2, e+g=3; for example, —CH$_2$F, —CHF$_2$, —CF$_3$, —CCl$_3$, or —CBr$_3$;
viii) —SO$_2$R$^{28}$; for example, —SO$_2$H; —SO$_2$CH$_3$; —SO$_2$C$_6$H$_5$;
ix) $C_1$-$C_6$ linear, branched, or cyclic alkyl;
x) Cyano
xi) Nitro;
xii) N(R$^{28}$)C(O)R$^{28}$;
xiii) Oxo (=O);
xiv) Heterocycle; and
xv) Heteroaryl.
wherein each R$^{28}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g. optionally substituted $C_3$-$C_4$ cycloalkyl); or two R$^{28}$ units can be taken together to form a ring comprising 3-7 ring atoms. In certain aspects, each R$^{28}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_1$-$C_6$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the prodrug agent described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemric and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, naphthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^{13})_2$, each $R^{13}$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

As used herein, the term "Lanicemine prodrug" shall mean a compound that are cleaved to release Lanicemine in the plasma via either an enzymatic or general biophysical release process.

As used herein, the term "prodrug agent" shall mean a compound that are cleaved to release Lanicemine in the plasma via either an enzymatic or general biophysical release process.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The Prodrug Agents:

The prodrug agents of the present invention are N-substituted Lanicemine analogs, and include all enantiomeric and diastereomeric forms and pharmaceutically accepted salts thereof having the formula (I):

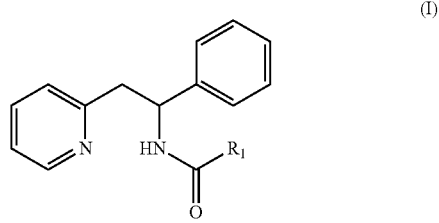

(I)

including hydrates, solvates, pharmaceutically acceptable salts, and complexes thereof, wherein:

$R^1$ is selected from the group consisting of $C_1$-$C_6$ fluoroalkyl, $OR^2$, $(CR^{6a}R^{6b})_m NHR^7$,

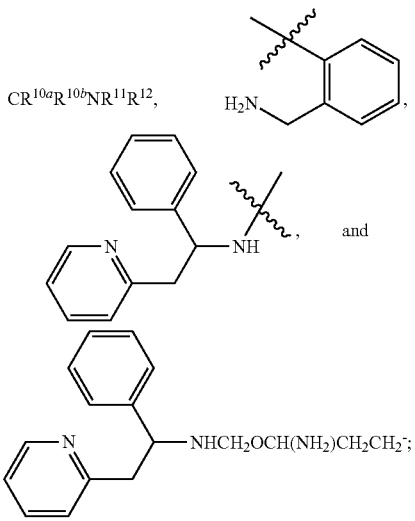

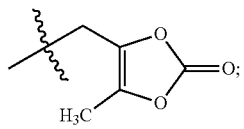 [SMILES: *Cc1oc(=O)oc1C]

$R^2$ is selected from the group consisting of $CH_2(CH_2)_n NR^{3a}R^{3b}$,

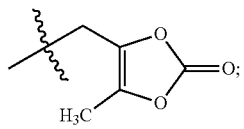 [SMILES: *Cc1oc(=O)oc1C]

$R^{3a}$ and $R^{3b}$ are independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, and $CO_2R^4$;

$R^{3a}$ and $R^{3b}$ cannot both be $C_1$-$C_6$ alkyl;

$R^{3a}$ and $R^{3b}$ are taken together with the atom to which they are bound to form an optionally substituted three to six membered saturated heterocyclic ring consisting of two to five carbon atoms and a member selected from the group consisting of O, $NR^5$, S, and $SO_2$;

n is 1 or 2;

$R^4$ is selected from the group consisting of $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted phenyl, and optionally substituted benzyl;

$R^5$ is selected from the group consisting of $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{6a}$ and $R^{6b}$ are at each occurrence independently selected from the group consisting of hydrogen, optionally substituted $C_1$-$C_6$ alkyl, optionally substituted $C_3$-$C_7$ branched alkyl, optionally substituted $C_2$-$C_6$ alkenyl, optionally substituted $C_2$-$C_6$ alkynyl, and optionally substituted $C_3$-$C_7$ cycloalkyl;

$R^{6a}$ and $R^{6b}$ are taken together with the atom to which they are bound to form an optionally substituted 6 membered ring;

m is 1, 2, or 3;

$R^7$ is selected from the group consisting of $COCR^{8a}R^{8b}(NHR^9)$

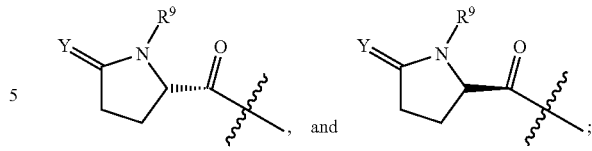

$R^{8a}$ and $R^{8b}$ are at each occurrence independently selected from the group consisting of hydrogen, $CH_3$, $CH(CH_3)_2$, $CH_2CH(CH_3)_2$, $CH(CH_3)CH_2CH_3$, $CH_2OH$, $CH(OH)CH_3$, $CH_2Ph$, $CH_2(4$-$OH$-$Ph)$, $(CH_2)_4NH_2$, $(CH_2)_3NHC(NH_2)NH$, $CH_2(3$-$indole)$, $CH_2(5$-$imidazole)$, $CH_2CO_2H$, $CH_2CH_2CO_2H$, $CH_2CONH_2$, and $CH_2CH_2CONH_2$;

$R^9$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_{2-6}$ alkynyl;

Y is at each occurrence independently selected from the group consisting of $H_2$ or O;

$R^{10a}$ and $R^{10b}$ are at each occurrence independently selected from the group consisting of hydrogen, $CH_3$, $CH_2CH_3$, $CH(CH_3)_2$, $CH_2CH(CH_3)_2$, $CH(CH_3)CH_2CH_3$, $CH_2OH$, $CH_2OCH_2Ph$, $CH(OH)CH_3$, $CH_2Ph$, $CH_2(4$-$OH$-$Ph)$, $(CH_2)_4 NH_2$, $(CH_2)_3NHC(NH_2)NH$, $CH_2(3$-$indole)$, $CH_2(5$-$imidazole)$, $CH_2(CCH)$, $CH_2(cyclohexyl)$, $CH_2CO_2H$, $CH_2CH_2CO_2H$, $CH_2CONH_2$, and $CH_2CH_2CONH_2$;

$R^{10a}$ and $R^{10b}$ are taken together with the atom to which they are bound to form an optionally substituted three to six membered saturated carbocyclic ring;

$R^{11}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_1$-$C_6$ haloalkyl, and $C_2$-$C_6$ alkynyl;

$R^{12}$ is at each occurrence independently selected from the group consisting of hydrogen, $C_1$-$C_6$ alkyl, $COCR^{13a}R^{13b}R^{15a}R^{15b}$, $COCR^{13a}R^{13b}OR^{14}$, $SO_2CR^{13a}R^{13b}NR^{15a}R^{15b}$, $COCR^{13a}R^{13b}NHSO_2R^{15a}$,

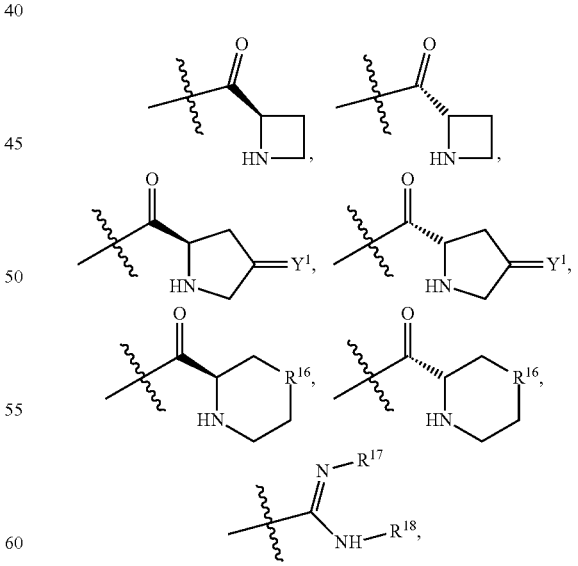

and $(CR^{19a}R^{19b})_q NHR^{20}$, and when $R^{12}$ is hydrogen, $R^{11}$ cannot be hydrogen;

$R^{11}$ and $R^{12}$ are taken together with the atom to which they are bound to form an optionally substituted four to six membered saturated heterocyclic ring containing a nitrogen atom and optionally containing an additional heteroatom from the group consisting of N and O;

$R^{13a}$ and $R^{13b}$ are at each occurrence independently selected from the group consisting hydrogen, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$;

$R^{13a}$ and $R^{13b}$ are taken together with the atom to which they are bound to form an optionally substituted three to six membered saturated carbocyclic ring;

$R^{13a}$ and $R^{13b}$ are taken together with the atom to which they are bound to form an optionally substituted six membered saturated heterocyclic ring with one O atom within the ring;

$R^{13a}$ and $R^{14}$ are taken together with the atoms to which they are bound to form an optionally substituted four to six membered ring containing one nitrogen atom;

$R^{13a}$ and $R^{15a}$ are taken together with the atoms to which they are bound to form an optionally substituted four to six membered ring containing one nitrogen atom;

$Y^1$ is at each occurrence independently selected from the group consisting of H, O, and —H/—OCH$_2$Ph;

$R^{14}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{15a}$ and $R^{15b}$ are at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, $C_1$-$C_6$ fluoroalkyl, $COR^{21}$, $CH_2R^{21}$, $SO_2R^{22}$, an optionally substituted four to six membered saturated heterocyclic ring containing a heteroatom selected from the group consisting of $NR^{24}$ and O, $COCHR^{23}NH_2$

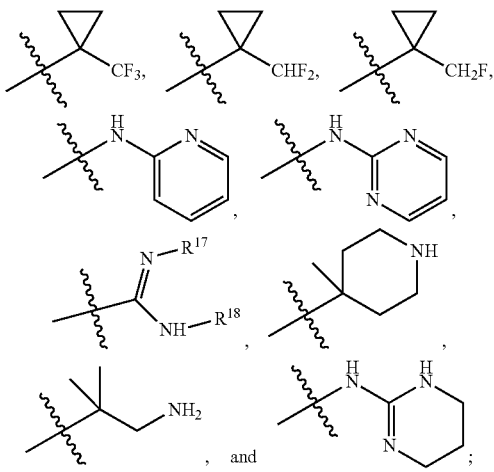

, and $R^{15a}$ and $R^{15b}$ are taken together with the atom to which they are bound to form an optionally substituted four to six membered saturated heterocyclic ring optionally containing one O atom within the ring;

$R^{16}$ is at each occurrence independently selected from the group consisting of $CH_2$, O, C=O, and NH;

$R^{17}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{18}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{17}$ and $R^{18}$ are taken together with the atoms to which they are bound to form an optionally substituted five or six membered ring containing two nitrogen atoms;

$R^{19a}$ and $R^{19b}$ are at each occurrence independently selected from the group consisting of hydrogen, optionally substituted $C_1$-$C_6$ alkyl, optionally substituted $C_3$-$C_7$ branched alkyl, optionally substituted $C_3$-$C_7$ cycloalkyl, optionally substituted $C_2$-$C_6$ alkenyl, and optionally substituted $C_2$-$C_6$ alkynyl;

$R^{19a}$ and $R^{19b}$ are taken together with the atom to which they are bound to form an optionally substituted 3 to 6 membered carbocyclic ring;

$R^{20}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

q is, or 2;

$R^{21}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, $C_1$-$C_6$ fluoroalkyl, optionally substituted aryl, and optionally substituted heteroaryl;

$R^{22}$ is at each occurrence independently selected from the group consisting of $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl optionally substituted aryl, optionally substituted heteroaryl;

$R^{23}$ is selected from the group consisting H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph) $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$;

$R^{24}$ is at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted aryl, optionally substituted heteroaryl, $COR^{25}$, and $SO_2$—$C_{1-6}$alkyl;

$R^{25}$ is at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted aryl, optionally substituted heteroaryl, $C_1$-$C_6$alkoxy, and $C_1$-$C_6$ alkylamino.

The compounds of the present invention include compounds having formula (II):

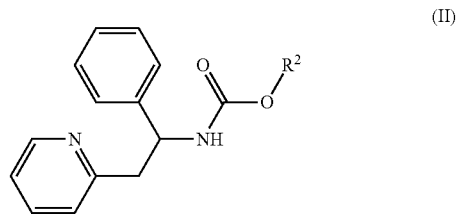

(II)

including enantiomers, diastereomers, hydrates, solvates, pharmaceutically acceptable salts, and complexes thereof.

The compounds of the present invention include compounds having formula (III):

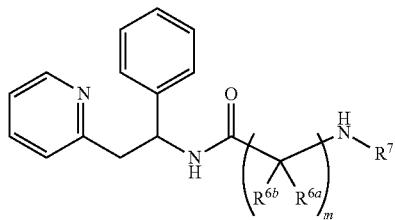

(III)

including enantiomers, diastereomers, hydrates, solvates, pharmaceutically acceptable salts, and complexes thereof.

The compounds of the present invention include compounds having formula (IV):

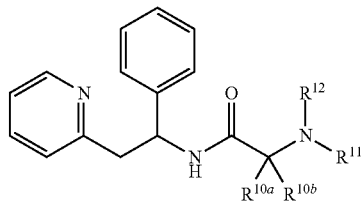

(IV)

including enantiomers, diastereomers, hydrates, solvates, pharmaceutically acceptable salts, and complexes thereof.

The compounds of the present invention include compounds having formula (V):

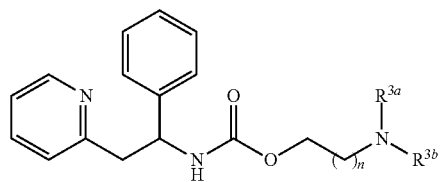

(V)

including enantiomers, diastereomers, hydrates, solvates, pharmaceutically acceptable salts, and complexes thereof.

The compounds of the present invention include compounds having formula (VI):

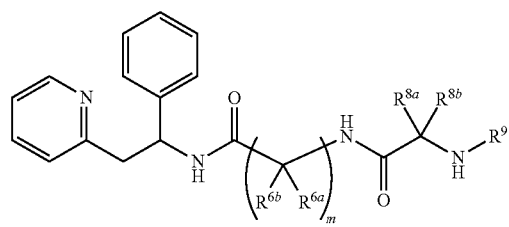

(VI)

including enantiomers, diastereomers, hydrates, solvates, pharmaceutically acceptable salts, and complexes thereof.

The compounds of the present invention include compounds having formula (VII):

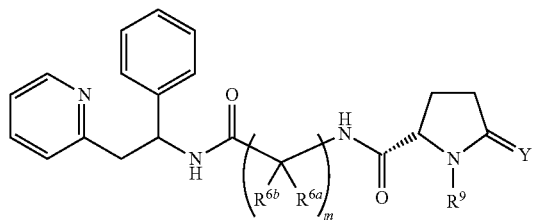

(VII)

including enantiomers, diastereomers, hydrates, solvates, pharmaceutically acceptable salts, and complexes thereof.

The compounds of the present invention include compounds having formula (VIII):

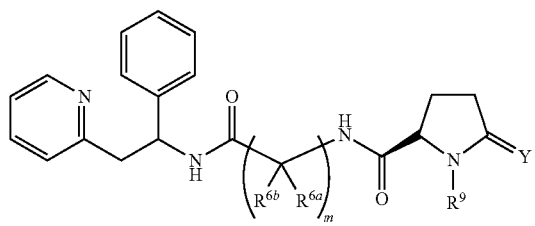

(VIII)

including enantiomers, diastereomers, hydrates, solvates, pharmaceutically acceptable salts, and complexes thereof.

The compounds of the present invention include compounds having formula (IX):

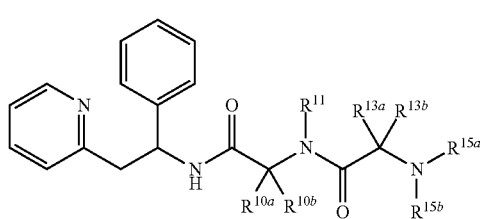

(IX)

including enantiomers, diastereomers, hydrates, solvates, pharmaceutically acceptable salts, and complexes thereof.

The compounds of the present invention include compounds having formula (X):

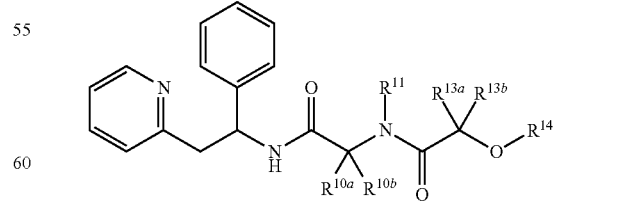

(X)

including enantiomers, diastereomers, hydrates, solvates, pharmaceutically acceptable salts, and complexes thereof.

The compounds of the present invention include compounds having formula (XI):

(XI)

including enantiomers, diastereomers, hydrates, solvates, pharmaceutically acceptable salts, and complexes thereof.

The compounds of the present invention include compounds having formula (XII):

(XII)

including enantiomers, diastereomers, hydrates, solvates, pharmaceutically acceptable salts, and complexes thereof.

The compounds of the present invention include compounds having formula (XIII):

(XIII)

including enantiomers, diastereomers, hydrates, solvates, pharmaceutically acceptable salts, and complexes thereof.

The compounds of the present invention include compounds having formula (XIV):

(XIV)

including enantiomers, diastereomers, hydrates, solvates, pharmaceutically acceptable salts, and complexes thereof.

The compounds of the present invention include compounds having formula (XV):

(XV)

including enantiomers, diastereomers, hydrates, solvates, pharmaceutically acceptable salts, and complexes thereof.

The compounds of the present invention include compounds having formula (XVI):

(XVI)

including enantiomers, diastereomers, hydrates, solvates, pharmaceutically acceptable salts, and complexes thereof.

The compounds of the present invention include compounds having formula (XVII):

(XVII)

including enantiomers, diastereomers, hydrates, solvates, pharmaceutically acceptable salts, and complexes thereof.

In some embodiments $R^1$ is $C_1$-$C_6$ fluoroalkyl.

In some embodiments $R^1$ is $OR^2$.

In some embodiments $R^1$ is $(CR^{6a}R^{6b})_m NHR^7$.

In some embodiments $R^1$ is $CR^{10a}R^{10b}NR^{11}R^{12}$.

In some embodiments $R^1$ is

In some embodiments $R^1$ is

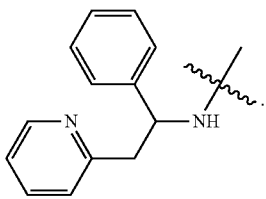 [SMILES: *NC(Cc1ccccn1)c1ccccc1]

In some embodiments $R^1$ is

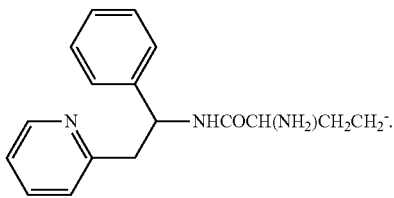

In some embodiments $R^2$ is $CH_2(CH_2)_nNR^{3a}R^{3b}$.
In some embodiments $R^2$ is

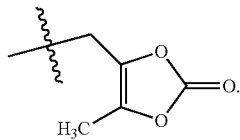 [SMILES: *Cc1oc(=O)oc1C]

In some embodiments $R^{3a}$ is hydrogen.
In some embodiments $R^{3a}$ is $C_1$-$C_6$ alkyl.
In some embodiments $R^{3a}$ is $C_3$-$C_7$ cycloalkyl.
In some embodiments $R^{3a}$ is $C_3$-$C_7$ branched alkyl.
In some embodiments $R^{3a}$ is $C_2$-$C_6$ alkenyl.
In some embodiments $R^{3a}$ is $C_2$-$C_6$ alkynyl.
In some embodiments $R^{3b}$ is $CO_2R^4$.
In some embodiments $R^{3b}$ is hydrogen.
In some embodiments $R^{3b}$ is $C_1$-$C_6$ alkyl.
In some embodiments $R^{3b}$ is $C_3$-$C_7$ cycloalkyl.
In some embodiments $R^{3b}$ is $C_3$-$C_7$ branched alkyl.
In some embodiments $R^{3b}$ is $C_2$-$C_6$ alkenyl.
In some embodiments $R^{3b}$ is $C_2$-$C_6$ alkynyl.
In some embodiments $R^{3a}$ is $CO_2R^4$.
In some embodiments $R^{3a}$ and $R^{3b}$ are taken together with the atom to which they are bound to form an optionally substituted three to six membered saturated heterocyclic ring consisting of two to five carbon atoms and a member selected from the group consisting of O, $NR^5$, S, and $SO_2$;
In some embodiments n is 1.
In some embodiments n is 2.
In some embodiments $R^4$ is $C_1$-$C_6$ alkyl.
In some embodiments $R^4$ is $C_3$-$C_7$ branched alkyl.
In some embodiments $R^4$ is $C_3$-$C_7$ cycloalkyl.
In some embodiments $R^4$ is $C_2$-$C_6$ alkenyl.
In some embodiments $R^4$ is $C_2$-$C_6$ alkynyl.
In some embodiments $R^4$ is optionally substituted phenyl.
In some embodiments $R^4$ is benzyl.
In some embodiments $R^5$ is $C_1$-$C_6$ alkyl
In some embodiments $R^5$ is $C_3$-$C_7$ branched alkyl
In some embodiments $R^5$ is $C_3$-$C_7$ cycloalkyl.
In some embodiments $R^5$ is $C_2$-$C_6$ alkenyl.
In some embodiments $R^5$ is $C_2$-$C_6$ alkynyl.
In some embodiments $R^{6a}$ is hydrogen.
In some embodiments $R^{6a}$ is optionally substituted $C_1$-$C_6$ alkyl.
In some embodiments $R^{6a}$ is optionally substituted $C_3$-$C_7$ branched alkyl.
In some embodiments $R^{6a}$ is optionally substituted $C_3$-$C_7$ cycloalkyl.
In some embodiments $R^{6a}$ is optionally substituted $C_2$-$C_6$ alkenyl.
In some embodiments $R^{6a}$ is optionally substituted $C_2$-$C_6$ alkynyl.
In some embodiments $R^{6b}$ is hydrogen.
In some embodiments $R^{6b}$ is optionally substituted $C_1$-$C_6$ alkyl.
In some embodiments $R^{6b}$ is optionally substituted $C_3$-$C_7$ branched alkyl.
In some embodiments $R^{6b}$ is optionally substituted $C_3$-$C_7$ cycloalkyl.
In some embodiments $R^{6b}$ is optionally substituted $C_2$-$C_6$ alkenyl.
In some embodiments $R^{6b}$ is optionally substituted $C_2$-$C_6$ alkynyl.
In some embodiments $R^{6a}$ and $R^{6b}$ are taken together with the atom to which they are bound to form an optionally substituted 6 membered ring.
In some embodiments m is 1.
In some embodiments m is 2.
In some embodiments m is 3.
In some embodiments $R^7$ is $COCR^{5a}R^{5b}(NHR^9)$.
In some embodiments R is

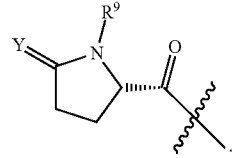

In some embodiments $R^7$ is

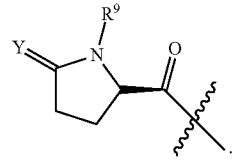

In some embodiments $R^8$ is hydrogen.
In some embodiments $R^{8a}$ is $CH_3$.
In some embodiments $R^{8a}$ is $CH(CH_3)_2$.
In some embodiments $R^{8a}$ is $CH_2CH(CH_3)_2$.
In some embodiments $R^{8a}$ is $CH(CH_3)CH_2CH_3$.
In some embodiments $R^{8a}$ is $CH_2OH$.
In some embodiments $R^{8a}$ is $CH(OH)CH_3$.
In some embodiments $R^{8a}$ s $CH_2Ph$.
In some embodiments $R^{8a}$ is $CH_2(4\text{-}OH\text{-}Ph)$.
In some embodiments $R^{8a}$ is $(CH_2)_4NH_2$.
In some embodiments $R^{8a}$ is $(CH_2)_3NHC(NH_2)NH$.
In some embodiments $R^{8a}$ is $CH_2(3\text{-indole})$.
In some embodiments $R^{8a}$ is $CH_2(5\text{-imidazole})$.
In some embodiments $R^{8a}$ is $CH_2CO_2H$.
In some embodiments $R^{8a}$ is $CH_2CH_2CO_2H$.
In some embodiments $R^{8a}$ is $CH_2CONH_2$.
In some embodiments $R^{8a}$ is $CH_2CH_2CONH_2$.
In some embodiments $R^{8b}$ is hydrogen.

In some embodiments $R^{8b}$ is $CH_5$.
In some embodiments $R^{8b}$ is $CH(CH_3)_2$.
In some embodiments $R^{8b}$ is $CH_2CH(CH_3)_2$.
In some embodiments $R^{8b}$ is $CH(CH_3)CH_2CH_3$.
In some embodiments $R^{8b}$ is $CH_2OH$.
In some embodiments $R^{8b}$ is $CH(OH)CH_3$.
In some embodiments $R^{8b}$ is $CH_2Ph$.
In some embodiments $R^{8b}$ is $CH_2(4\text{-}OH\text{-}Ph)$.
In some embodiments $R^{8b}$ is $(CH_2)_4NH_2$.
In some embodiments $R^{8b}$ is $(CH_2)_3NHC(NH_2)NH$.
In some embodiments $R^{8b}$ is $CH_2(3\text{-indole})$.
In some embodiments $R^{8b}$ is $CH_2(5\text{-imidazole})$.
In some embodiments $R^{8b}$ is $CH_2CO_2H$.
In some embodiments $R^{8b}$ is $CH_2CH_2CO_2H$.
In some embodiments $R^{8b}$ is $CH_2CONH_2$.
In some embodiments $R^{8b}$ is $CH_2CH_2CONH_2$.
In some embodiments $R^9$ is hydrogen.
In some embodiments $R^9$ is $C_1$-$C_6$ alkyl.
In some embodiments $R^9$ is $C_3$-$C_7$ branched alkyl.
In some embodiments $R^9$ is $C_3$-$C_7$ cycloalkyl.
In some embodiments $R^9$ is $C_2$-$C_6$ alkenyl.
In some embodiments $R^9$ is $C_2$-$C_6$ alkynyl.
In some embodiments Y is $H_2$.
In some embodiments Y is O.
In some embodiments $R^{10a}$ is hydrogen.
In some embodiments $R^{10a}$ is $CH_3$.
In some embodiments $R^{10a}$ is $CH_2CH_3$.
In some embodiments $R^{10a}$ is $CH(CH_3)_2$.
In some embodiments $R^{10a}$ is $CH_2CH(CH_3)_2$.
In some embodiments $R^{10a}$ is $CH(CH_3)CH_2CH_3$.
In some embodiments $R^{10a}$ is $CH_2OH$.
In some embodiments $R^{10a}$ is $CH_2OCH_2Ph$.
In some embodiments $R^{10a}$ is $CH(OH)CH_3$.
In some embodiments $R^{10a}$ is $CH_2Ph$.
In some embodiments $R^{10a}$ is $CH_2(4\text{-}OH\text{-}Ph)$.
In some embodiments $R^{10a}$ is $(CH_2)_4NH_2$.
In some embodiments $R^{10a}$ is $(CH)_3NHC(NH_2)NH$.
In some embodiments $R^{10a}$ is $CH_2(3\text{-indole})$.
In some embodiments $R^{10a}$ is $CH_2(5\text{-imidazole})$.
In some embodiments $R^{10a}$ is $CH_2(CCH)$.
In some embodiments $R^{10a}$ is $CH_2(\text{cyclohexyl})$.
In some embodiments $R^{10a}$ is $CH_2CO_2H$.
In some embodiments $R^{10a}$ is $CH_2CH_2CO_2H$.
In some embodiments $R^{10a}$ is $CH_2CONH_2$.
In some embodiments $R^{10a}$ is $CH_2CH_2CONH_2$.
In some embodiments $R^{10b}$ is hydrogen.
In some embodiments $R^{10b}$ is $CH_3$.
In some embodiments $R^{10b}$ is $CH_2CH_3$.
In some embodiments $R^{10b}$ is $CH(CH_3)_2$.
In some embodiments $R^{10b}$ is $CH_2CH(CH_3)_2$.
In some embodiments $R^{10b}$ is $CH(CH_3)CH_2CH_3$.
In some embodiments $R^{10b}$ is $CH_2OH$.
In some embodiments $R^{10b}$ is $CH_2OCH_2Ph$.
In some embodiments $R^{10b}$ is $CH(OH)CH_3$.
In some embodiments $R^{10b}$ is $CH_2Ph$.
In some embodiments $R^{10b}$ is $CH_2(4\text{-}OH\text{-}Ph)$.
In some embodiments $R^{10b}$ is $(CH_2)_4NH_2$.
In some embodiments $R^{10b}$ is $(CH_2)_3NHC(NH_2)NH$.
In some embodiments $R^{10b}$ is $CH_2(3\text{-indole})$.
In some embodiments $R^{10b}$ is $CH_2(5\text{-imidazole})$.
In some embodiments $R^{10b}$ is $CH_2(CCH)$.
In some embodiments $R^{10b}$ is $CH_2(\text{cyclohexyl})$.
In some embodiments $R^{10b}$ is $CH_2CO_2H$.
In some embodiments $R^{10b}$ is $CH_2CH_2CO_2H$.
In some embodiments $R^{10b}$ is $CH_2CONH_2$.
In some embodiments $R^{10b}$ is $CH_2CH_2CONH_2$.

In some embodiments $R^{10a}$ and $R^{10b}$ are taken together with the atom to which they are bound to form an optionally substituted three to six membered saturated carbocyclic ring.
In some embodiments $R^{11}$ is hydrogen.
In some embodiments $R^{11}$ is of $C_1$-$C_6$ alkyl.
In some embodiments $R^{11}$ is $C_3$-$C_7$ branched alkyl.
In some embodiments $R^{11}$ is $C_3$-$C_7$ cycloalkyl.
In some embodiments $R^{11}$ is $C_2$-$C_6$ alkenyl.
In some embodiments $R^{11}$ is $C_1$-$C_6$ haloalkyl.
In some embodiments $R^{11}$ is $C_2$-$C_6$ alkynyl.
In some embodiments $R^{12}$ is hydrogen.
In some embodiments $R^{12}$ is $C_1$-$C_6$ alkyl.
In some embodiments $R^{12}$ is $COCR^{13a}R^{13b}NR^{15a}R^{15b}$.
In some embodiments $R^{12}$ is $COCR^{13a}R^{13b}OR^{14}$.
In some embodiments $R^{12}$ is $SO_2CR^{13a}R^{13b}NR^{15a}R^{15b}$.
In some embodiments $R^{12}$ is $COCR^{13a}R^{13b}NHSO_2R^{15a}$.
In some embodiments $R^{12}$ is

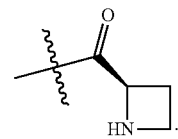 [SMILES: *C(=O)[C@H]1CCN1]

In some embodiments $R^{12}$ is

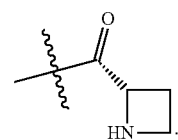

In some embodiments $R^{12}$ is

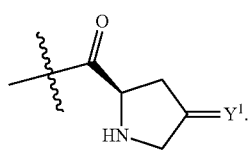

In some embodiments $R^{12}$ is

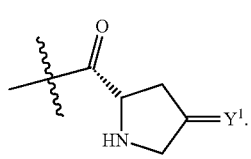

In some embodiments $R^{12}$ is

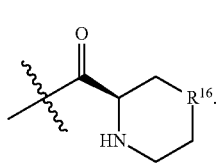

In some embodiments $R^{12}$ is

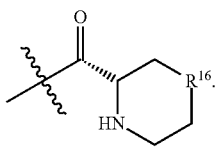

In some embodiments $R^{12}$ is

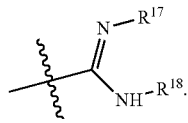

In some embodiments $R^{12}$ is $(CR^{19a}R^{19b})_q NHR^{20}$.

In some embodiments $R^{11}$ and $R^{12}$ are taken together with the atom to which they are bound to form an optionally substituted four to six membered saturated heterocyclic ring containing a nitrogen atom and optionally containing an additional heteroatom from the group consisting of N and O.

In some embodiments $R^{13a}$ is hydrogen.
In some embodiments $R^{13a}$ is $CH_3$.
In some embodiments $R^{13a}$ is $CH_2CH_3$.
In some embodiments $R^{13a}$ is $CH_2CH_2CH_3$.
In some embodiments $R^{13a}$ $CH_2CCH$.
In some embodiments $R^{13a}$ is $CH(CH_3)_2$.
In some embodiments $R^{13a}$ is $CH_2CH(CH_3)_2$.
In some embodiments $R^{13a}$ is $CH(CH_3)CH_2CH_3$.
In some embodiments $R^{13a}$ is $CH_2OH$.
In some embodiments $R^{13a}$ is $CH_2OCH_2Ph$.
In some embodiments $R^{13a}$ is $CH_2CH_2OCH_2Ph$.
In some embodiments $R^{13a}$ is $CH(OH)CH_3$.
In some embodiments $R^{13a}$ is $CH_2Ph$.
In some embodiments $R^{13a}$ is $CH_2(cyclohexyl)$.
In some embodiments $R^{13a}$ is $CH_2(4\text{-}OH\text{-}Ph)$.
In some embodiments $R^{13a}$ is $(CH_2)_4NH_2$.
In some embodiments $R^{13a}$ is $(CH_2)_3NHC(NH_2)NH$.
In some embodiments $R^{13a}$ is $CH_2(3\text{-indole})$.
In some embodiments $R^{13a}$ is $CH_2(5\text{-imidazole})$.
In some embodiments $R^{13a}$ is $CH_2CO_2H$.
In some embodiments $R^{13a}$ is $CH_2CH_2CO_2H$.
In some embodiments $R^{13a}$ is $CH_2CONH_2$.
In some embodiments $R^{13a}$ is $CH_2CH_2CONH_2$.
In some embodiments $R^{13b}$ is hydrogen.
In some embodiments $R^{13b}$ is $CH_3$.
In some embodiments $R^{13b}$ is $CH_2CH_3$.
In some embodiments $R^{13b}$ is $CH_2CH_2CH_3$.
In some embodiments $R^{13b}$ is $CH_2CCH$.
In some embodiments $R^{13b}$ is $CH(CH_3)_2$.
In some embodiments $R^{13b}$ is $CH_2CH(CH_3)_2$.
In some embodiments $R^{13b}$ is $CH(CH_3)CH_2CH_3$.
In some embodiments $R^{13b}$ is $CH_2OH$.
In some embodiments $R^{13b}$ is $CH_2OCH_2Ph$.
In some embodiments $R^{13b}$ is $CH_2CH_2CH_2Ph$.
In some embodiments $R^{13b}$ is $CH(OH)CH_3$.
In some embodiments $R^{13b}$ is $CH_2Ph$.
In some embodiments $R^{13b}$ is $CH_2(cyclohexyl)$.
In some embodiments $R^{13b}$ is $CH_2(4\text{-}OH\text{-}Ph)$.
In some embodiments $R^{13b}$ is $(CH_2)_4NH_2$.
In some embodiments $R^{13b}$ is $(CH_2)_3NHC(NH_2)NH$.
In some embodiments $R^{13b}$ is $CH_2(3\text{-indole})$.
In some embodiments $R^{13b}$ is $CH_2(5\text{-imidazole})$.
In some embodiments $R^{13b}$ is $CH_2CO_2H$.
In some embodiments $R^{3b}$ is $CH_2CH_2CO_2H$.
In some embodiments $R^{13b}$ is $CH_2CONH_2$.
In some embodiments $R^{13b}$ is $CH_2CH_2CONH_2$.
In some embodiments $R^{13a}$ and $R^{13b}$ are taken together with the atom to which they are bound to form an optionally substituted three to six membered saturated carbocyclic ring.

In some embodiments $R^{13a}$ and $R^{13b}$ are taken together with the atom to which they are bound to form an optionally substituted six membered saturated heterocyclic ring with one O atom within the ring.

In some embodiments $R^{13a}$ and $R^{14}$ are taken together with the atoms to which they are bound to form an optionally substituted four to six membered ring containing one nitrogen atom.

In some embodiments $R^{13a}$ and $R^{15a}$ are taken together with the atoms to which they are bound to form an optionally substituted four to six membered ring containing one nitrogen atom.

In some embodiments $Y^1$ is
In some embodiments $Y^1$ is $H_2$.
In some embodiments $Y^1$ is O.
In some embodiments $Y^1$ is $—H/—OC_2Ph$.
In some embodiments $R^{14}$ is hydrogen.
In some embodiments $R^{14}$ is $C_1\text{-}C_6$ alkyl.
In some embodiments $R^{14}$ is $C_3\text{-}C_7$ branched alkyl.
In some embodiments $R^{14}$ is $C_3\text{-}C_7$ cycloalkyl.
In some embodiments $R^{14}$ is $C_2\text{-}C_6$ alkenyl.
In some embodiments $R^{14}$ is $C_2\text{-}C_6$ alkynyl.
In some embodiments $R^{15a}$ is hydrogen.
In some embodiments $R^{15a}$ is $C_1\text{-}C_6$ alkyl.
In some embodiments $R^{15a}$ is $C_3\text{-}C_7$ branched alkyl.
In some embodiments $R^{15a}$ is $C_3\text{-}C_7$ cycloalkyl.
In some embodiments $R^{15a}$ is $C_2\text{-}C_6$ alkenyl.
In some embodiments $R^{15a}$ is $C_2\text{-}C_6$ alkynyl.
In some embodiments $R^{15a}$ $C_1\text{-}C_6$ fluoroalkyl.
In some embodiments $R^{15a}$ is $COR^{21}$.
In some embodiments $R^{15a}$ is $CH_2R^{21}$.
In some embodiments $R^{15a}$ is $SO_2R^{22}$.
In some embodiments $R^{15a}$ is an optionally substituted four to six membered saturated heterocyclic ring containing a heteroatom selected from the group consisting of $NR^{24}$, and O.

In some embodiments $R^{15a}$ is $COCHR^2NH_2$.
In some embodiments $R^{15a}$ is

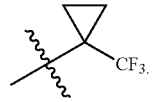 [SMILES: *C1(C(F)(F)F)CC1]

In some embodiments $R^{15a}$ is

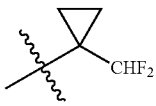 [SMILES: *C1(C(F)F)CC1]

In some embodiments $R^{15a}$ is

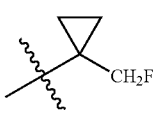

In some embodiments $R^{15a}$ is

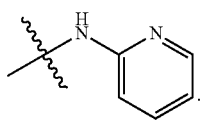

In some embodiments $R^{15a}$ is

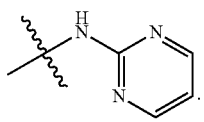

In some embodiments $R^{15a}$ is

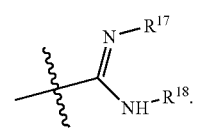

In some embodiments $R^{15a}$ is

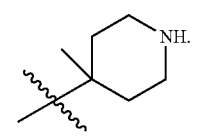

In some embodiments $R^{15a}$ is

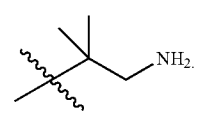

In some embodiments $R^{15a}$ is

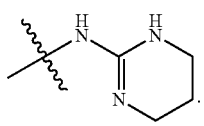

In some embodiments $R^{15b}$ is hydrogen.
In some embodiments $R^{15}$ b is $C_1$-$C_6$ alkyl.
In some embodiments $R^{15b}$ is $C_3$-$C_7$ branched alkyl.
In some embodiments $R^{15b}$ is $C_3$-$C_7$ cycloalkyl.
In some embodiments $R^{15b}$ is $C_2$-$C_6$ alkenyl.
In some embodiments $R^{15b}$ is $C_2$-$C_6$ alkynyl.
In some embodiments $R^{15b}$ is $C_1$-$C_6$ fluoroalkyl.
In some embodiments $R^{15b}$ is $COR^{21}$.
In some embodiments $R^{15b}$ is $CH_2R^{21}$.
In some embodiments $R^{15b}$ is $SO_2R^{22}$.
In some embodiments $R^{15b}$ is an optionally substituted four to six membered saturated heterocyclic ring containing a heteroatom selected from the group consisting of $NR^{24}$ and O.

In some embodiments $R^{5b}$ is $COCHR^{23}NH_2$.
In some embodiments $R^{15b}$ is

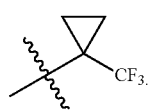 [SMILES: *C1(C(F)(F)F)CC1]

In some embodiments $R^{15b}$ is

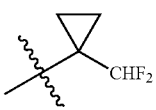 [SMILES: *C1(C(F)F)CC1]

In some embodiments $R^{15b}$ is

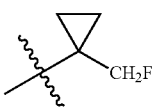

In some embodiments $R^{15b}$ is

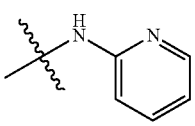

In some embodiments $R^{15b}$ is

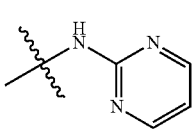

In some embodiments $R^{15b}$ is

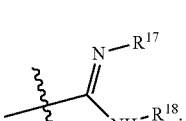

In some embodiments $R^{15b}$ is

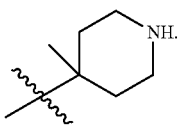 [SMILES: *C1(C)CCNCC1]

In some embodiments $R^{15b}$ is

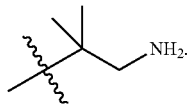 [SMILES: *C(C)(C)CN]

In some embodiments $R^{15b}$ is

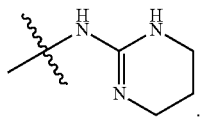 [SMILES: *NC1=NCCCN1]

In some embodiments $R^{15a}$ and $R^{15b}$ are taken together with the atom to which they are bound to form an optionally substituted four to six membered saturated heterocyclic ring optionally containing one O atom within the ring.
In some embodiments $R^{16}$ is $CH_2$.
In some embodiments $R^{16}$ is O.
In some embodiments $R^{16}$ is C=O.
In some embodiments $R^{16}$ is NH.
In some embodiments $R^{17}$ is hydrogen.
In some embodiments $R^{17}$ is $C_1$-$C_6$ alkyl.
In some embodiments $R^{17}$ is $C_3$-$C_7$ branched alkyl.
In some embodiments $R^{17}$ is $C_3$-$C_7$ cycloalkyl.
In some embodiments $R^{17}$ is $C_2$-$C_6$ alkenyl.
In some embodiments $R^{17}$ is $C_2$-$C_6$ alkynyl.
In some embodiments $R^{18}$ is hydrogen.
In some embodiments $R^{18}$ is $C_1$-$C_6$ alkyl.
In some embodiments $R^{18}$ is $C_3$-$C_7$ branched alkyl.
In some embodiments $R^{18}$ is $C_3$-$C_7$ cycloalkyl.
In some embodiments $R^{18}$ is $C_2$-$C_6$ alkenyl.
In some embodiments $R^{18}$ is $C_2$-$C_6$ alkynyl.
In some embodiments $R^{17}$ and $R^{18}$ are taken together with the atoms to which they are bound to form an optionally substituted five or six membered ring containing two nitrogen atoms.
In some embodiments $R^{19a}$ is hydrogen.
In some embodiments $R^{19a}$ is optionally substituted $C_1$-$C_6$ alkyl.
In some embodiments $R^{19a}$ is optionally substituted $C_3$-$C_7$ branched alkyl.
In some embodiments $R^{19a}$ is optionally substituted $C_3$-$C_7$ cycloalkyl.
In some embodiments $R^{19a}$ is optionally substituted $C_2$-$C_6$ alkenyl.
In some embodiments $R^{19a}$ is optionally substituted $C_2$-$C_6$ alkynyl.
In some embodiments $R^{19b}$ is hydrogen.
In some embodiments $R^{19b}$ is optionally substituted $C_1$-$C_6$ alkyl.
In some embodiments $R^{19b}$ is optionally substituted $C_3$-$C_7$ branched alkyl.
In some embodiments $R^{19b}$ is optionally substituted $C_3$-$C_7$ cycloalkyl.
In some embodiments $R^{19b}$ is optionally substituted $C_2$-$C_6$ alkenyl.
In some embodiments $R^{19b}$ is optionally substituted $C_2$-$C_6$ alkynyl.
In some embodiments $R^{19a}$ and $R^{19b}$ are taken together with the atom to which they are bound to form an optionally substituted 3 membered carbocyclic ring.
In some embodiments $R^{19a}$ and $R^{19b}$ are taken together with the atom to which they are bound to form an optionally substituted 4 membered carbocyclic ring.
In some embodiments $R^{19a}$ and $R^{19b}$ are taken together with the atom to which they are bound to form an optionally substituted 5 membered carbocyclic ring.
In some embodiments $R^{19a}$ and $R^{19b}$ are taken together with the atom to which they are bound to form an optionally substituted 6 membered carbocyclic ring.
In some embodiments $R^{20}$ is hydrogen.
In some embodiments $R^{20}$ is $C_1$-$C_6$ alkyl.
In some embodiments $R^{20}$ is $C_3$-$C_7$ branched alkyl.
In some embodiments $R^{20}$ is $C_3$-$C_7$ cycloalkyl.
In some embodiments $R^{20}$ is $C_2$-$C_6$ alkenyl.
In some embodiments $R^{20}$ is $C_2$-$C_6$ alkynyl.
In some embodiments q is 1.
In some embodiments q is 2.
In some embodiments $R^{21}$ is hydrogen.
In some embodiments $R^{21}$ is $C_1$-$C_6$ alkyl.
In some embodiments $R^{21}$ is $C_3$-$C_7$ branched alkyl.
In some embodiments $R^{21}$ is $C_3$-$C_7$ cycloalkyl.
In some embodiments $R^{21}$ is $C_2$-$C_6$ alkenyl.
In some embodiments $R^{21}$ is $C_2$-$C_6$ alkynyl.
In some embodiments $R^{21}$ is $C_1$-$C_6$ fluoroalkyl.
In some embodiments $R^{21}$ is optionally substituted aryl.
In some embodiments $R^{21}$ is optionally substituted heteroaryl.
In some embodiments $R^{22}$ is $C_1$-$C_6$ alkyl.
In some embodiments $R^{22}$ is $C_3$-$C_7$ branched alkyl.
In some embodiments $R^{22}$ is $C_3$-$C_7$ cycloalkyl.
In some embodiments $R^{22}$ is $C_2$-$C_6$ alkenyl.
In some embodiments $R^{22}$ is $C_2$-$C_6$ alkynyl.
In some embodiments $R^{22}$ is optionally substituted aryl.
In some embodiments $R^{22}$ is optionally substituted heteroaryl
In some embodiments $R^{23}$ is hydrogen.
In some embodiments $R^{23}$ is $CH_3$.
In some embodiments $R^{23}$ is $CH_2CH_3$.
In some embodiments $R^{23}$ is $CH_2CH_2CH_2$.
In some embodiments $R^{23}$ is $CH_2CCH$.
In some embodiments $R^{23}$ is $CH(CH_3)_2$.
In some embodiments $R^{23}$ is $CH_2CH(CH_3)_2$.
In some embodiments $R^{23}$ is $CH(CH_3)CH_2CH_3$.
In some embodiments $R^{23}$ is $CH_2OH$.
In some embodiments $R^{23}$ is $CH_2OCH_2Ph$.
In some embodiments $R^{23}$ is $CH_2CH_2OCH_2Ph$.
In some embodiments $R^{23}$ is $CH(OH)CH_3$.
In some embodiments $R^{23}$ is $CH_2Ph$.
In some embodiments $R^{23}$ is $CH_2(cyclohexyl)$.
In some embodiments $R^{23}$ is $CH_2(4\text{-OH-Ph})$.
In some embodiments $R^{23}$ is $(CH_2)_4NH_2$.
In some embodiments $R^{23}$ is $(CH_2)_3NHC(NH_2)NH$.
In some embodiments $R^{23}$ is $CH_2(3\text{-indole})$.
In some embodiments $R^{23}$ is $CH_2(5\text{-imidazole})$.
In some embodiments $R^{23}$ is $CH_2CO_2H$.
In some embodiments $R^{23}$ is $CH_2CH_2CO_2H$.
In some embodiments $R^{23}$ is $CH_2CONH_2$.
In some embodiments $R^{23}$ is $CH_2CH_2CONH_2$.
In some embodiments $R^{24}$ is hydrogen.
In some embodiments $R^{24}$ is $C_1$-$C_6$ alkyl.
In some embodiments $R^{24}$ is $C_3$-$C_7$ branched alkyl.
In some embodiments $R^{24}$ is $C_3$-$C_7$ cycloalkyl.
In some embodiments $R^{24}$ is $C_2$-$C_6$ alkenyl.
In some embodiments $R^{24}$ is $C_2$-$C_6$ alkynyl.
In some embodiments $R^{24}$ is optionally substituted aryl.
In some embodiments $R^{24}$ is optionally substituted heteroaryl.

In some embodiments $R^{24}$ is $COR^{25}$.
In some embodiments $R^{24}$ is $SO_2$—$C_{1-6}$alkyl.
In some embodiments $R^{25}$ is hydrogen.
In some embodiments $R^{25}$ is $C_1$-$C_6$ alkyl.
In some embodiments $R^{25}$ is $C_3$-$C_7$ branched alkyl.
In some embodiments $R^{25}$ is $C_3$-$C_7$ cycloalkyl.
In some embodiments $R^{25}$ is $C_2$-$C_6$ alkenyl.
In some embodiments $R^{25}$ is $C_2$-$C_6$ alkynyl.
In some embodiments $R^{25}$ is optionally substituted aryl.
In some embodiments $R^{25}$ is optionally substituted heteroaryl.
In some embodiments $R^{25}$ is $C_1$-$C_6$ alkoxy.
In some embodiments $R^{25}$ is $C_1$-$C_6$ alkylamino.

Exemplary non-limiting embodiments of the invention include 2-(methylamino)-N-(2-oxo-2-((2-(2-pyridyl)-1-(phenyl)ethyl)amino)ethyl)acetamide;
(S)—N-(2-oxo-2-((2-(2-pyridyl)-1-(phenyl)ethyl)amino)ethyl)pyrrolidine-2-carboxamide;
(R)-2-amino-N-(2-oxo-2-((2-(2-pyridyl)-1-(phenyl)ethylamino)ethyl)propanamide;
3-amino-N-(2-oxo-2-((2-(2-pyridyl)-1-(phenyl)ethyl)amino)ethyl) propanamide;
1-amino-N-(2-oxo-2-((2-(2-pyridyl)-1-(phenyl)ethyl)amino)ethyl)cyclopropane-1-carboxamide;
(S)—N-(2-oxo-2-((2-(2-pyridyl)-1-phenyl)ethyl)amino)ethyl)azetidine-2-carboxamide;
2-amino-2-methy-N-(2-oxo-2-((2-(2-pyridyl)-1-(phenyl)ethyl)amino)ethyl)propanamide;
(S)-2-(methylamino)-N-(2-oxo-2-((2-(2-pyridyl)-1-(phenyl)ethyl)amino)ethyl)propanamide;
(R)-2-(methylamino)-N-(2-oxo-2-((2-(2-pyridyl)-1-(phenyl)ethyl)amino)ethyl)propanamide;
(R)-2-amino-3-hydroxy-N-(2-oxo-2-((2-(4-pyridyl2-pyridyl)-1-(phenyl)ethyl)amino)ethyl)propanamide;
(R)-2-amino-N-(2-oxo-2((2-(2-pyridyl)-1-(phenyl)ethyl)amino)ethyl)pent-4-ynamide;
(S)-2-amino-N-(2-oxo-2-((2-(2-pyridyl)-1-(phenyl)ethyl)amino)ethyl)pent-4-ynamide;
(R)—N-(2-oxo-2-((2-(2-pyridyl)-1-(phenyl)ethyl)amino)ethyl)pyrrolidine-2-carboxamide;
1-amino-N-(2-oxo-2-((2-(2-pyridyl)-1-(phenyl)ethylamino)ethyl)cyclobutane-1-carboxamide;
(S)-2-amino-N-(2-oxo-2-((2-(2-pyridyl)-1-(phenyl)ethyl)amino)ethyl)pentanamide;
(R)-2-amino-3-methyl-N-(2-oxo-2-((2-(2-pyridyl)-1-(phenyl)ethyl)amino)ethyl)butanamide;
(S)-4-oxo-N-(2-oxo-2-(2-(2-pyridyl)-1-(phenyl)ethyl)amino)ethyl)pyrrolidine-2-carboxamide;
(S)—N-(2-oxo-2-((2-(2-pyridyl)-1-(phenyl)ethyl)amino)ethyl)piperidine-2-carboxamide;
(S)—N-(2-oxo-2-((2-(2-pyridyl)-1-(phenyl)ethyl)amino)ethyl)morpholine-3-carboxamide;
(R)—N-(2-oxo-2-((2-(2-pyridyl)-1-(phenyl)ethyl)amino)ethyl)morpholine-3-carboxamide;
(R)-2-amino-4-methyl-N-(2-oxo-2-((2-(2-pyridyl)-1-(phenyl)ethyl)amino)ethyl)pentanamide;
(R)-4-oxo-N-(2-oxo-2-((2-(2-pyridyl-1-(phenyl)ethyl)amino)ethyl)piperidine-2-carboxamide;
4-amino-N-(2-oxo-2-((2-(2-pyridyl)-1-(phenyl)ethyl)amino)ethyl)tetrahydro-2H-pyran-4-carboxamide;
(R)-2-amino-N1-(2-oxo-2-((2-(2-pyridyl)-1-(phenyl)ethyl)amino)ethyl)pentanediamide;
(R)-2-amino-N-(2-oxo-2-((2-(2-pyridyl)-1-(phenyl)ethyl)amino)ethyl)-3-phenylpropanamide;
(R)-2-amino-3-cyclohexyl-N-(2-oxo-2 ((2 (2-pyridyl)-1-(phenyl)ethyl)amino)ethyl)propanamide;
(R)-2-amino-3-(benzyloxy)-N-(2-oxo-2-((2-(2-pyridyl-1-(phenyl)ethyl)amino)ethyl)propanamide;
(S)-2-amino-3-(benzyloxy)-N-(2-oxo-2-((2-(2-pyridyl)-1-(phenyl)ethyl)amino)ethyl)propanamide;
(R)-2-amino-3-(1H-indol-3-yl)-N-(2-oxo-2-((2-(2-pyridyl)-1-(phenyl)ethyl)amino)ethyl)propanamide;
(2S,4R)-4-(benzyloxy)-N-(2-oxo-2-((2-(2-pyridyl)-1-(phenyl)ethyl)amino)ethyl)pyrrolidine-2-carboxamide;
(S)—N-(2-oxo-2-((2-(2-pyridyl)-1-(phenyl)ethyl)amino)ethyl)piperazine-2-carboxamide;
(R)-2-amino-4-(benzyloxy)-N-(2-oxo-2-(2-(2-pyridyl)-1-(phenyl)ethyl)amino)ethyl)butanamide;
(S)-1-glycyl-N-(2-(2-pyridyl)-1-(phenyl)ethyl)azetidine-2-carboxamide;
(S)-1-(3-aminopropanoyl)-N-(2-(2-pyridyl)-1-(phenyl)ethyl)azetidine-2-carboxamide;
(S)-1-(1-(aminomethyl)cyclopropane-1-carbonyl)-N-(2-(2-pyridyl)-1-(phenyl)ethyl)azetidine-2-carboxamide;
(S)-1-(1 (aminomethyl)cyclopentane-1-carbonyl)-N-(2-(2-pyridyl)-1-(phenyl)ethyl)azetidine-2-carboxamide;
(S)-1-glycyl-N-(2-(2-pyridyl)-1-(phenyl)ethyl)piperidine-2-carboxamide;
(S)-1-(3-aminopropanoyl)-N-(2-(2-pyridyl)-1-(phenyl)ethyl)piperidine-2-carboxamide;
(S)-1-(3-aminopropanoyl)-N-(2-(2-pyridyl)-1-(phenyl)ethyl)piperidine-2-carboxamide;
(R)-1-(methylglycyl)-N-(2-(2-pyridyl)-1-(phenyl)ethyl)piperidine-2-carboxamide;
1-(2-aminoacetamido)-N-(2-(2-pyridyl)-1-(phenyl)ethyl)cyclopropane-1-carboxamide;
1-(2-(methylamino)acetamido)-N-(2-(2-pyridyl)-1-(phenyl)ethyl)cyclopropane-1-carboxamide;
1-(2-aminoacetamido)-N-(2-(2-pyridyl)-1-(phenyl)ethyl)cyclobutane-1-carboxamide;
1-(2-(methylamino)acetamido)-N-(2-(2-pyridyl)-1-(phenyl)ethyl)cyclobutane-1-carboxamide;
1-(3-amino-2,2-dimethylpropanamido)-N-(2-(2-pyridyl)-1-(phenyl)ethyl)cyclobutane-1-carboxamide;
1-(aminomethyl)-N-(1-((2-(2-pyridyl)-1-(phenyl)ethyl)carbamoyl)cyclobutyl)cyclopentane-1-carboxamide;
1-(2-(isopropylamino)acetamido)-N-(2-(2-pyridyl)-1-(phenyl)ethyl)cyclobutane-1-carboxamide;
1-(2-(isopropylamino)acetamido)-N-(2-(2-pyridyl)-1-(phenyl)ethyl)cyclobutane-1-carboxamide;
1-(aminomethyl)-N-(1-((2-(2-pyridyl)-1-(phenyl)ethyl)carbamoyl)cyclobutyl)cyclohexane-1-carboxamide;
(R)-1-(2-aminopropanamido)-N-(2-(2-pyridyl)-1-(phenyl)ethylcyclobutane-1-carboxamide;
(R)-1-(2-amino-3-methylbutanamido)-N-(2-(2-pyridyl)-1-(phenyl)ethyl)cyclobutane-1-carboxamide;
(S)-2-(2-aminoacetamido)-3-phenyl-N-(2-(2-pyridyl)-1-(phenyl)ethyl)propanamide;
(S)-2-(2-(methylamino)acetamido)-3-phenyl-N-(2-(2-pyridyl)-1-(phenyl)ethyl)propanamide;
(S)-2-((R)-2-aminopropanamido)-3-phenyl-N-(2-(2-pyridyl)-1-(phenyl)ethyl)propanamide;
(S)-2-((S)-2-aminopropanamido)-3-phenyl-N-(2-(2-pyridyl)-1-(phenyl)ethyl)propanamide;
(R)-2-amino-3-methyl-N—((S)-1-oxo-3-phenyl-1-((2-(2-pyridyl)-1-(phenyl)ethyl)amino)propan-2-yl)butanamide;
(S)-2-amino-2-methyl-N-(1-oxo-3-phenyl-1-((2-(2-pyridyl)-1-(phenyl)ethyl)amino)propan-2-yl)propanamide;
(S)-1-amino-N-(1-oxo-3-phenyl-1-((2-(2-pyridyl)-1-(phenyl)ethyl)amino)propan-2-yl)cyclopropane-1-carboxamide;

(S)-1-amino-N-(1-oxo-3-phenyl-1-((2-(2-pyridyl)-1-(phenyl)ethyl)amino)propan-2-yl)cyclobutane-1-carboxamide;
1-(3-amino-2,1-dimethylpropanamido)-N-(2-(2-pyridyl)-1-(phenyl)ethyl)cyclobutane-1-carboxamide;
(R)-2-(2-aminopropanamido)-2-methyl-N-(2-(2-pyridyl)-1-(phenyl)ethyl)propanamide;
(S)-2-(2-aminopropanamido)-2-methyl-N-(2-(2-pyridyl)-1-(phenyl)ethyl)propanamide;
2-(2-aminoacetamido)-2-methyl-N-(2-(2-pyridyl)-1-(phenyl)ethyl)propanamide;
(R)-2-amino-N-(2-methyl-1-oxo-1-((2-(2-pyridyl)-1-(phenyl)ethyl)amino)propan-2-yl)-3-phenylpropanamide;
(S)-2-amino-3-(benzyloxy)-N-(2-methy-1-oxo-1-((2-(2-pyridyl)-1-(phenyl)ethyl)amino)propan-2-yl)propanamide;
1-amino-N-(2-methyl-1-oxo-1-((2-(2-pyridyl)-1-(phenyl)ethyl)amino)propan-2-yl)cyclopropane-1-carboxamide;
1-amino-N-(2-methyl-1-oxo-1-((2-(2-pyridyl)-1-(phenyl)ethyl)amino)propan-2-yl)cyclobutane-1-carboxamide;
2-amino-2-methyl-N-(2-methyl-1-oxo-1-((2-(2-pyridyl)-1-(phenyl)ethyl)amino)propan-2-yl)propanamide;
3-amino-2,2-dimethyl-N-(2-methyl-1-oxo-1-((2-(2-pyridyl)-1-(phenyl)ethyl)amino)propan-2-yl)propanamide;
1-(aminomethyl)-N-(2-methyl-1-oxo-1-((2-(2-pyridyl)-1-(phenyl)ethyl)amino)propan-2-yl)cyclopropane-1-carboxamide;
1-(aminomethyl)-N-(2-methyl-1-oxo-1-((2-(2-pyridyl)-1-(phenyl)ethyl)amino)propan-2-yl)cyclopentane-1-carboxamide;
1-(aminomethyl)-N-(2-methyl-1-oxo-1-((2-(2-pyridyl)-1-(phenyl)ethyl)amino)propan-2-yl)cyclohexane-1-carboxamide;
2-methyl-2-(2-(methylamino)acetamido)-N-(2-(2-pyridyl)-1-(phenyl)ethyl)propanamide;
2-(2-(ethylamino)acetamido)-2 methyl-N-(2-(2-pyridyl)-1-(phenyl)ethyl)propanamide;
2-(2-(isopropylamino)acetamido)-2-methyl-N-(2-(2-pyridyl)-1-(phenyl)ethyl)propanamide;
2-(2-(tert-butylamino)acetamido)-2-methyl-N-(2-(2-pyridyl)-1-(phenyl)ethyl)propanamide;
(S)-2-(2-aminoacetamido)-N-(2-(2-pyridyl)-1-(phenyl)ethyl)propanamide;
(S)-2-amino-N—((S)-1-oxo-1-((2-(2-pyridyl)-1-(phenyl)ethylamino)propan-2-yl)propanamide;
(R)-2-amino-N—((S)-1-oxo-1-((2-(2-pyridyl)-1-(phenyl)ethyl)amino)propan-2-yl)propanamide;
3-Amino-N,2,2-trimethyl-N-(2-oxo-2-((2-(2-pyridyl)-1-(phenyl)ethyl)amino)ethyl)propanamide;
1-(aminomethyl)-N-methyl-N-(2-oxo-2-((2-(2-pyridyl)-1-(phenyl)ethyl)amino)ethyl)cyclopropane-1-carboxamide;
1-(aminomethyl)-N-methyl-N-(2-oxo-2-((2-(2-pyridyl)-1-(phenyl)ethylamino)ethyl)cyclopentane-1-carboxamide;
1-(aminomethyl)-N-methyl-N-(2-oxo-2-((2-(2-pyridyl)-1-(phenyl)ethyl)amino)ethyl)cyclohexane-1-carboxamide;
N-methyl-2-(methylamino)-N-(2-oxo-2-((2-(2-pyridyl)-1-(phenyl)ethyl)amino)ethyl)acetamide;
2-(ethylamino)-N-methyl-N-(2-oxo-2-((2(2-pyridyl)-1-(phenyl)ethyl)amino)ethyl)acetamide;
2-(isopropylamino)-N-methyl-N-(2-oxo-2-((2-(2-pyridyl)-1-(phenyl)ethyl)amino)ethyl)acetamide;
2-(tert-butylamino)-N-methyl-N-(2-oxo-2-((2-(2-pyridyl)-1-(phenyl)ethyl)amino)ethyl)acetamide,
2-(dimethylamino)-N-methyl-N-(2-oxo-2-((2-(2-pyridyl)-1-(phenyl)ethyl)amino)ethyl)acetamide;
2-amino-N-methyl-N-(2-oxo-2-((2-(2-pyridyl)-1-(phenyl)ethyl)amino)ethyl)acetamide;
(S)-2-amino-N-methyl-N-(2-oxo-2-((2-(2-pyridyl)-1-(phenyl)ethyl)amino)ethyl)propanamide;
(R)-2-amino-N-methyl-N-(2-oxo-2-((2-(2-pyridyl)-1-(phenyl)ethyl)amino)ethyl)propanamide;
3-amino-N-methyl-N-(2-oxo-2-((2-(2-pyridyl)-1-(phenyl)ethylamino)ethyl)propanamide;
2-amino-N-ethyl-N-(2-oxo-2-((2-(2-pyridyl)-1-(phenyl)ethylamino)ethyl)acetamide;
2-amino-N-isopropyl-N-(2-oxo-2-((2-(2-pyridyl)-1-(phenyl)ethyl)amino)ethyl)acetamide;
2-(aminomethyl)-N-(2-(2-pyridyl)-1-(phenyl)ethyl)benzamide;
tert-butyl (4-oxo-4-((2-(2-pyridyl)-1-(phenyl)ethyl)amino)butyl)carbamate;
4-amino-N-(2-(2-pyridyl)-1-(phenyl)ethyl)butanamide;
(S)—N-(4-oxo-4-((2-(2-pyridyl)-1-(phenyl)ethyl)amino)butyl)pyrrolidine-2-carboxamide;
(S)-2-amino-4-methyl-N-(4-oxo-4-((2-(2-pyridyl)-1-(phenyl)ethyl)amino)butyl)pentanamide;
4-(2-aminoacetamido)-N-(2-(2-pyridyl)-1-(phenyl)ethyl)butanamide;
(S)-4-(2-aminopropanamido)-N-(2-(2-pyridyl)-1-(phenyl)ethylbutanamide;
(S)-2-amino-3-methyl-N-(4-oxo-4-((2-(2-pyridyl)-1-(phenyl)ethyl)amino)butyl)butanamide;
(S)-5-oxo-N-(4-oxo-4-((2-(2-pyridyl)-1-(phenyl)ethyl)amino)butyl)pyrrolidine-2-carboxamide;
(2S,3S)-2-amino-3-methyl-N-(4-oxo-4-((2-(2-pyridyl)-1-(phenyl)ethyl)amino)butyl)pentanamide;
(S)-4-amino-5-oxo-5-((4-oxo-4-((2-(2-pyridyl)-1-(phenyl)ethylamino)butyl)amino)pentanoic acid;
(S)-2-amino-4-(methylthio)-N-(4-oxo-4-((2-(2-pyridyl)-1-(phenyl)ethyl)amino)butyl)butanamide;
(S)-4-(2-amino-3-phenylpropanamido)-N-(2-(2-pyridyl)-1-(phenyl)ethylbutanamide;
(S)-3-amino-4-oxo-4-((4-oxo-4-((2-(2-pyridyl)-1-(phenyl)ethylamino) butyl)amino)butanoic acid;
(S)-4-amino-5-oxo-5-((4-oxo-4-(2-(2-pyridyl)-1-(phenyl)ethyl)amino)butyl) amino)pentanoic acid;
(S)-4-(2-amino-3-(1H-indol-3-yl)propanamido)-N-(2-(2-pyridyl)-1-(phenyl)ethyl)butanamide;
(S)—N-((1-(2-oxo-2-((2-(2-pyridyl)-1-(phenyl)ethyl)amino)ethyl)cyclohexyl) methyl)pyrrolidine-2-carboxamide;
(S)—N-((1-(2-oxo-2-((2-(2-pyridyl)-1-(phenyl)ethyl)amino)ethyl)cyclohexyl) methyl)pyrrolidine-2-carboxamide;
(S)-2-amino-4-methyl-N-((1-(2-oxo-2-((2-(2-pyridyl)-1-(phenyl)ethyl)amino) ethyl)cyclohexyl)methyl)pentanamide;
(S)-2-amino-3-methyl-N-((1-(2-oxo-2-((2-(2-pyridyl)-1-(phenyl)ethyl)amino)ethyl)cyclohexyl)methyl)butanamide;
2-amino-N-((1-(2-oxo-2((2-(2-pyridyl)-1-(phenyl)ethyl)amino)ethyl) cyclohexyl))methyl)acetamide;
(S)-2-amino-N-((1-(2-oxo-2-((2-(2-pyridyl)-1-(phenyl)ethyl)amino)ethyl) cyclohexyl)methyl)propanamide;
2-(methylamino)-N-((1-(2-oxo-1-((2-(2-pyridyl)-1-(phenyl)ethyl)amino)ethyl) cyclohexyl)methyl)acetamide;
(R)-2-amino-3-methyl-N-((1-(2-oxo-2-((2-(2-pyridyl)-1-(phenyl)ethyl)amino) ethyl)cyclohexyl)methyl)butanamide;
(S)-5-oxo-N-((1-(2-oxo-2-((2-(2-pyridyl)-1-(phenyl)ethyl)amino)ethyl) cyclohexyl)methyl)pyrrolidine-2-carboxamide;

(S)-2-amino-N1-((1-(2-oxo-2-((2-(2-pyridyl)-1-(phenyl) ethylamino)ethyl) cyclohexyl)methyl)pentanediamide;
(S)-2-amino-4-(methylthio)-N-((1-(2-oxo-2-((2-(2-pyridyl)-1-(phenyl)ethyl)amino)ethyl)cyclohexyl)methyl)butanamide;
(S)-2-amino-N-((1-(2-oxo-2-((2-(2-pyridyl)-1-(phenyl) ethyl)amino)ethyl) cyclohexyl)methyl)-3-phenylpropanamide;
(S)-3-amino-4-oxo-4-(((1-(2-oxo-2-((2-(2-pyridyl)-1-(phenyl)ethyl)amino) ethyl)cyclohexyl)methyl)amino)butanoic acid;
(S)-4-amino-5-oxo-5-(((1-(2-oxo-2-((2-(2-pyridyl)-1-(phenyl)ethyl)amino) ethyl)cyclohexyl)methyl)amino)pentanoic acid;
(S)-2-amino-3-(1H-indol-3 yl)-N-((1-(2-oxo-2-((2 (2-pyridyl)-1-(phenyl)ethyl)amino)ethyl)cyclohexyl) methyl)propanamide;
(R)-2-amino-3-methyl-N-(4-oxo-4-((2-(2-pyridyl)-1-(phenyl)ethyl)amino) butyl)butanamide;
(R)—N-4-oxo-4-((2-(2-pyridyl)-1-(phenyl)ethyl)amino) butyl)pyrrolidine-2-carboxamide;
(R)-5-oxo-N-(4-oxo-4-((2-(2-pyridyl)-1-(phenyl)ethyl) amino)butyl)pyrrolidine-2-carboxamide;
(R)-2-amino-3-methyl-N-((1-(2-oxo-2-((2-(2-pyridyl)-1-(phenyl)ethyl)amino)ethyl) cyclohexyl)methyl)butanamide;
(S)—N-((1-(2-oxo-2-((2-(2-pyridyl)-1-(phenyl)ethyl) amino)ethyl)cyclohexyl) methyl)pyrrolidine-2-carboxamide;
(R)-5-oxo-N-((1-(2-oxo-2-((2-(2-pyridyl)-1-(phenyl)ethyl) amino)ethyl)cyclohexyl) methyl)pyrrolidine-2-carboxamide;
4-amino-3,3-dimethyl-N-(2-(2-pyridyl)-1-(phenyl)ethyl)butanamide;
(S)-3-(benzyloxyl)-2-morpholino-N-(2-(2-pyridyl)-1-(phenyl)ethyl)propanamide;
(S)-3-benzyloxy-2-(dimethylamino)-N-(2-(2-pyridyl)-1-(phenyl)ethyl)propanamide;
2-(ethylamino)-N-methyl-N-(2-oxo-2-((2-(2-pyridyl)-1-(phenyl)ethyl)amino)ethyl)acetamide;
2-(isopropylamino)-N-methyl-N-(2-oxo-2-((2-(2-pyridyl)-1-(phenyl)ethyl)amino)ethyl)acetamide;
N-methyl-2-(methylsulfonamido)-N-(2-oxo-2-((2-(2-pyridyl)-1-(phenyl)ethyl)amino)ethyl)acetamide;
2-(tert-butoxy)-N-methyl-N-(2-oxo-2-((2-(2-pyridyl)-1-(phenyl)ethyl)amino)ethyl)acetamide;
N,4,4-trimethyl-N-(2-oxo-2-((2-(2-pyridyl)-1-(phenyl) ethyl)amino)ethyl) pentanamide;
tert-Butyl (2-(methyl(2-oxo-2-((2-(2-pyridyl)-1-(phenyl) ethylamino)ethyl)amino)-2-oxoethyl)(1-(trifluoromethyl) cyclopropyl)carbamate;
N-methyl-N-(2-oxo-2-((2-(2-pyridyl)-1-(phenyl)ethyl) amino)ethyl)-2-((1-(trifluoromethyl)cyclopropyl)amino) acetamide;
N-methyl-N-(2-oxo-2((2-(2-pyridyl)-1-(phenyl)ethyl) amino)ethyl)-2-((2,2,2-trifluoroethyl)amino)acetamide hydrochloride;
2-acetamido-N-methyl-N-(2-oxo-2-((2-(2-pyridyl)-1-(phenyl)ethyl)amino)ethyl) acetamide;
N-(2-(methyl(2-oxo-2-((2-(2-pyridyl)-1-(phenyl)ethyl) amino)ethyl)amino)-2-oxoethyl)propionamide;
N-(2-(methyl(2-oxo-2-((2-(2-pyridyl)-1-(phenyl)ethyl) amino)ethyl)amino)-2-oxoethyl)butylamide;
N-(2 (methyl(2-oxo-2-((2-(2-pyridyl)-1-(phenyl)ethyl) amino)ethyl)amino)-2-oxoethyl)isobutyramide;
N-(2-(methyl(2-oxo-2-((2-(2-pyridyl)-1-(phenyl)ethyl) amino)ethyl)amino)-2-oxoethyl)benzamide;
2,2,2-trifluoro-N-(2-(methyl(2-oxo-2-((2-(2-pyridyl)-1-(phenyl)ethyl)amino)ethyl)amino-2-oxoethyl)acetamide;
N-methyl-N-(2-oxo-2-((2-(2-pyridyl)-1-(phenyl)ethyl) amino)ethyl)-2-((1,1,1-trifluoro-2-methylpropan-2-yl) amino)acetamide;
2-(2-oxopiperazin-1-yl)-N-(2-(2-pyridyl)-1-(phenyl)ethyl-acetamide;
(S)—N-methyl-N-(2-oxo-2-((2-(2-pyridyl)-1-(phenyl) ethyl)amino)ethyl) piperazine-2-carboxamide;
(R)—N-methyl-N-(2-oxo-2-((2-(2-pyridyl)-1-(phenyl) ethyl)amino)ethyl) piperazine-2-carboxamide;
Benzyl(2-(((2-(2-pyridyl)-1-(phenyl)ethyl)carbamoyl)oxy) ethyl)carbamate;
2-aminoethyl (2-(2-pyridyl)-1-(phenyl)ethyl)carbamate;
Benzyl ethyl (2-(((2-(2-pyridyl)-1-(phenyl)ethyl)carbamoyl)oxy)ethyl)carbamate;
2-(Ethylamino)ethyl (2-(2-pyridyl)-1-(phenyl)ethyl)carbamate;
Benzylmethyl(2-(((2-(2-pyridyl)-1-(phenyl)ethyl)carbamoyl)oxy)ethyl)carbamate;
2-(Methylamino)ethyl (2-(2-pyridyl)-1-(phenyl)ethyl)carbamate;
Benzyl isopropyl(2 (((2-(2 pyridyl)-1-(phenyl)ethyl)carbamoyl)oxy)ethyl)carbamate;
2-(Isopropylamino)ethyl (2-(2-pyridyl)-1-(phenyl)ethyl)carbamate;
(5-methyl-2-oxo-1,3-dioxol-4-yl)methyl (2-(2-pyridyl)-1-(phenyl)ethyl)carbamate;
4-amino-2,2-dimethyl-N-(2-(2-pyridyl)-1-(phenyl)ethyl)butanamide;
(S)-2-amino-N1,N5-bis(2-(2-pyridyl)-1-(phenyl)ethyl)pentanediamide;
2-(dimethylamino)-N-(2-(2-pyridyl)-1-(phenyl)ethyl)acetamide;
and 1,3-bis(2-(2-pyridyl)-1-(phenyl)ethyl)urea.

For the purposes of the present invention, a compound depicted by the racemic formula will stand equally well for either of the two enantiomers or mixtures thereof, or in the case where a second chiral center is present, all diastereomers.

For the purposes of the present invention, a compound depicted by the racemic formula will stand equally well for either of the two enantiomers or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Process

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of formula (I) may be prepared according to the process outlined in schemes 1-21.

Scheme 1

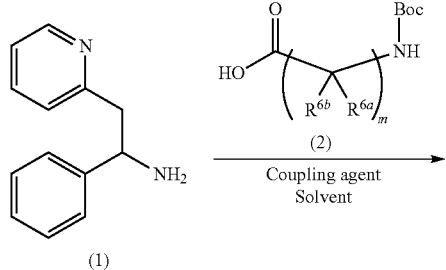

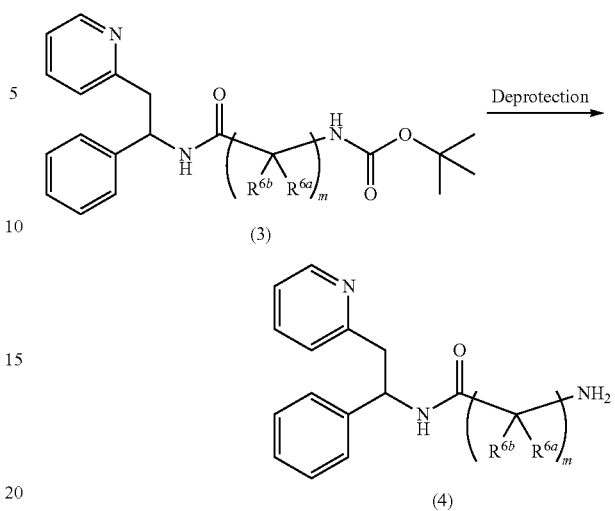

Lanicemine (1), a known compound, is reacted with a compound of the formula (2), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (3). A compound of the formula (3) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (4).

Scheme 2

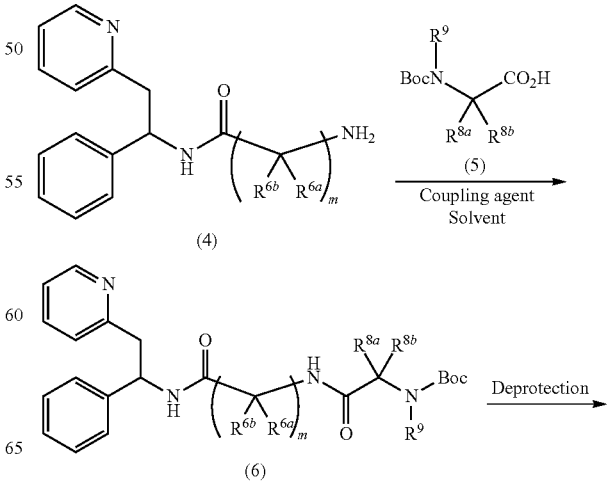

-continued

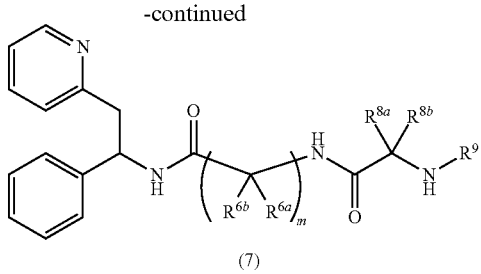

(7)

A compound of the formula (4) is reacted with a compound of the formula (5), a known compound or a compound made by known methods, in the presence of a coupling agent such as O-(benzotriazol-1-yl)-N,N,N',N'-tetramethyluronium hexafluorophosphate, N,N'-dicyclohexyl carbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, i-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (6). A compound of the formula (6) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (7).

Scheme 3

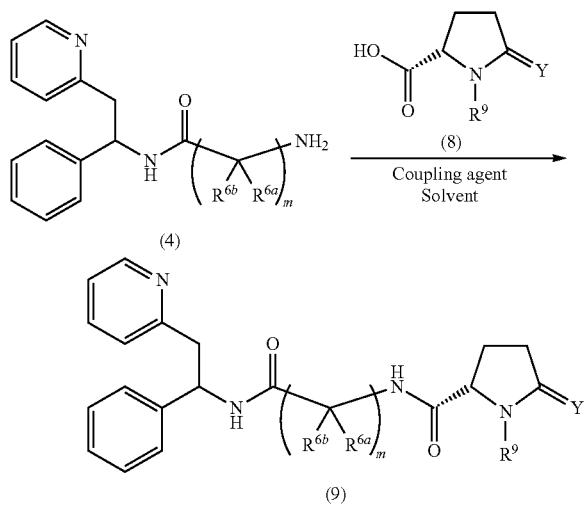

A compound of the formula (4) is reacted with a compound of (8), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (9).

Scheme 4

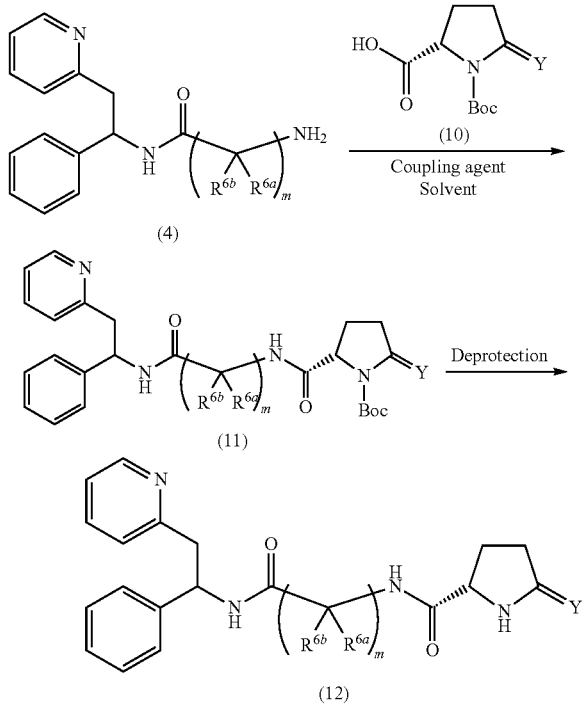

A compound of the formula (4) is reacted with a compound of (10), a known compound or a compound made by known methods, in the presence of a coupling agent such as O-(benzotriazol-1-yl)-N,N,N',N'-tetramethyluronium hexafluorophosphate, N,N'-dicyclohexyl carbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (11). A compound of the formula (11) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (12).

Scheme 5

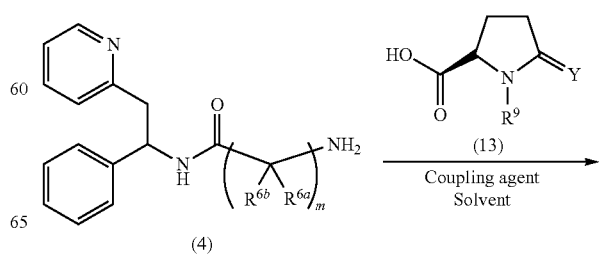

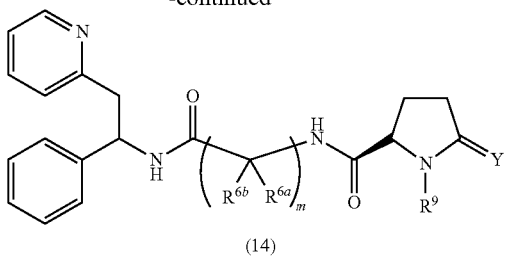

(14)

A compound of the formula (4) is reacted with a compound of (13), a known compound or a compound made by known methods, in the presence of a coupling agent such as O-(benzotriazol-1-yl)-N,N,N',N'-tetramethyluronium hexafluorophosphate, N,N'-dicyclohexyl carbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (14).

Scheme 6

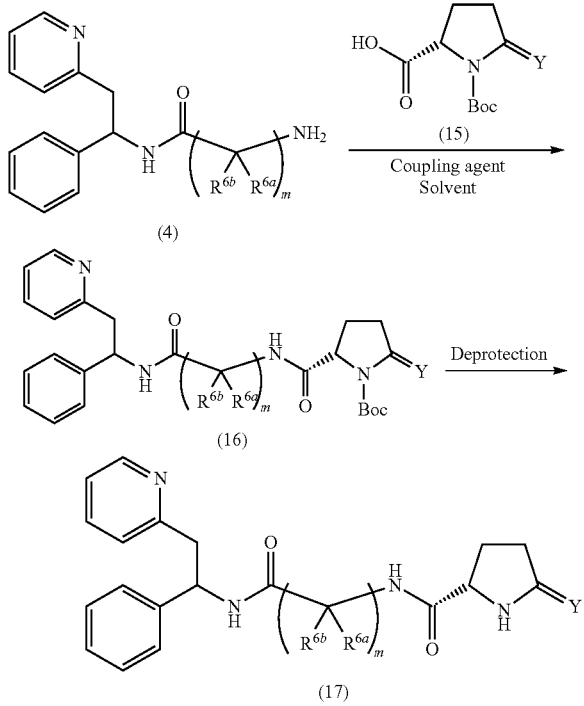

A compound of the formula (4) is reacted with a compound of (15), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (16). A compound of the formula (16) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (17).

Scheme 7

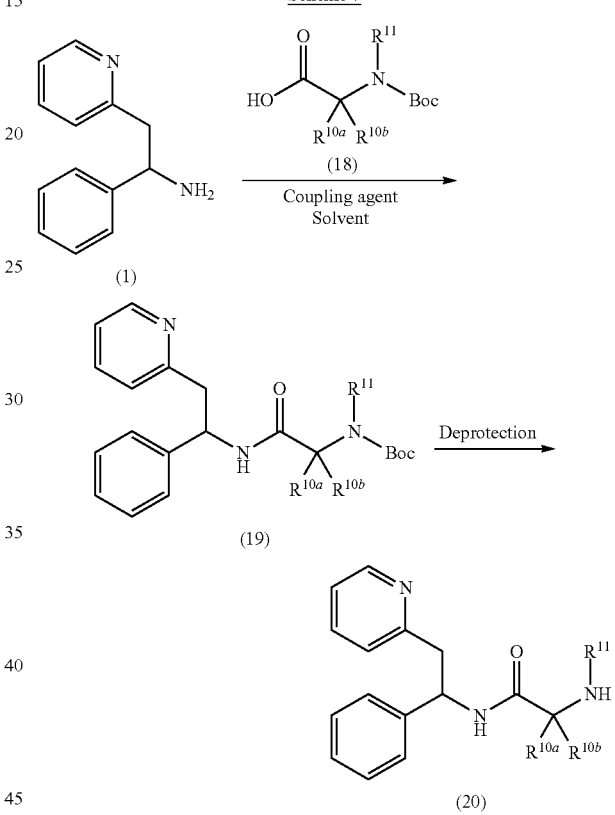

Lanicemine (1), a known compound, is reacted with a compound of the formula (18), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (19). A compound of the formula (19) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (20).

Scheme 8

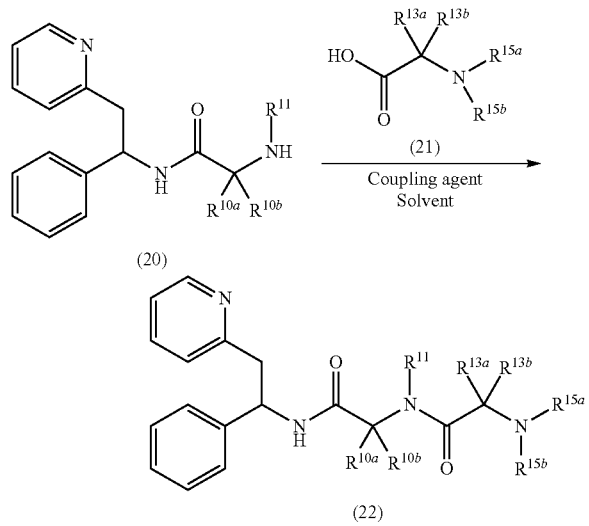

A compound of the formula (20) is reacted with a compound of (21), a known compound or a compound made by known methods, in the presence of a coupling agent such as O-(benzotriazol 1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (22).

Scheme 9

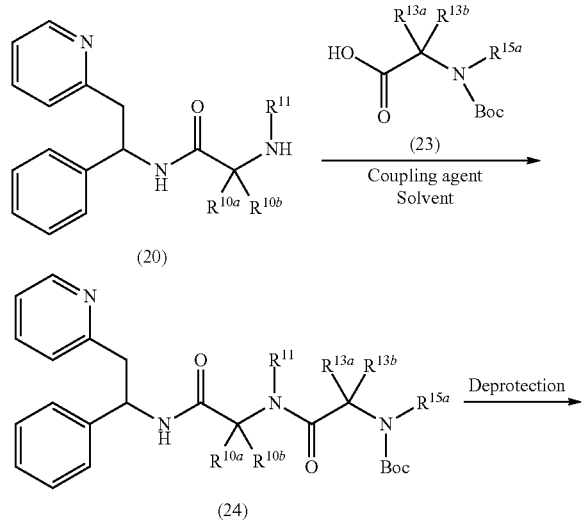

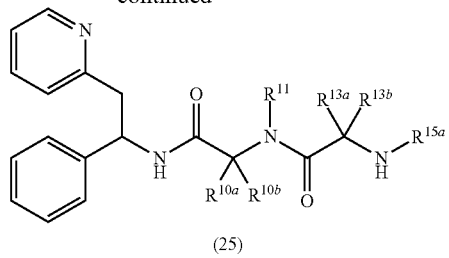

A compound of the formula (20) is reacted with a compound of (23), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-di methylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (24). A compound of the formula (24) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (25).

Scheme 10

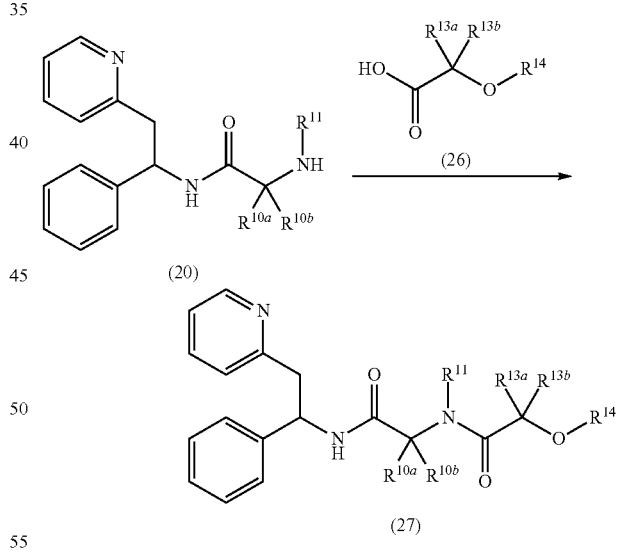

A compound of the formula (20) is reacted with a compound of (26), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (27).

Scheme 11

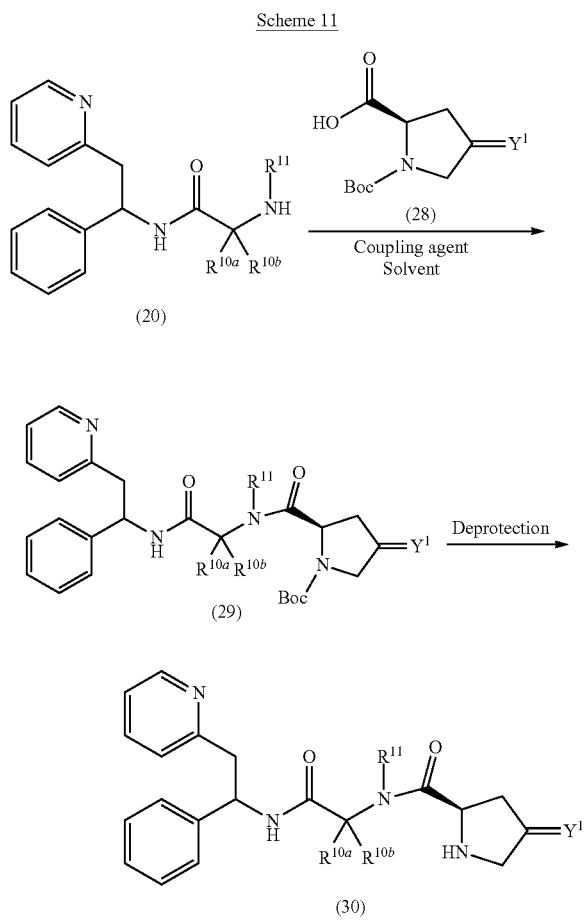

A compound of the formula (20) is reacted with a compound of (28), a known compound or a compound made by known methods, in the presence of a coupling agent such as O-(benzotriazol-1-yl)-N,N,N',N'-tetramethyluronium hexafluorophosphate, N,N'-dicyclohexyl carbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (29). A compound of the formula (29) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (30).

Scheme 12

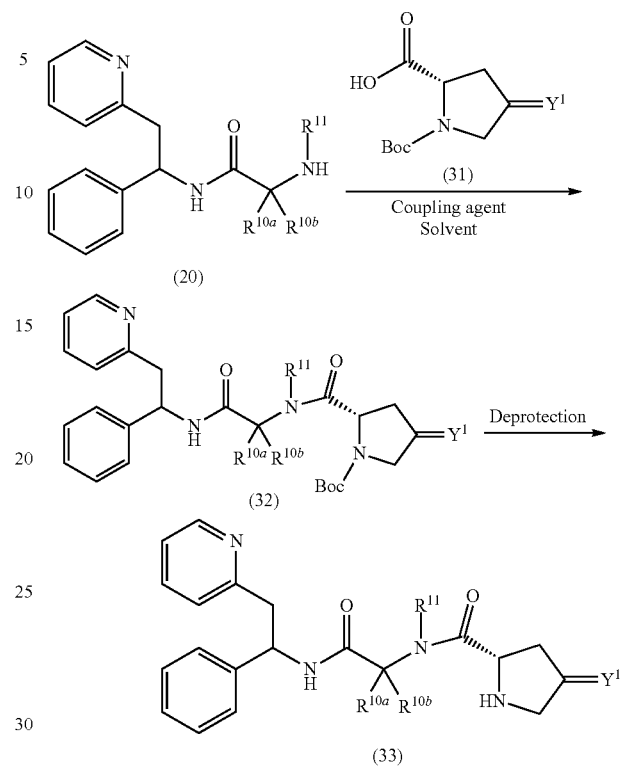

A compound of the formula (20) is reacted with a compound of (31), a known compound or a compound made by known methods, in the presence of a coupling agent such as O-(benzotriazol-1-yl)-N,N,N',N'-tetramethyluronium hexafluorophosphate, N,N'-dicyclohexyl carbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (32). A compound of the formula (32) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (33).

Scheme 13

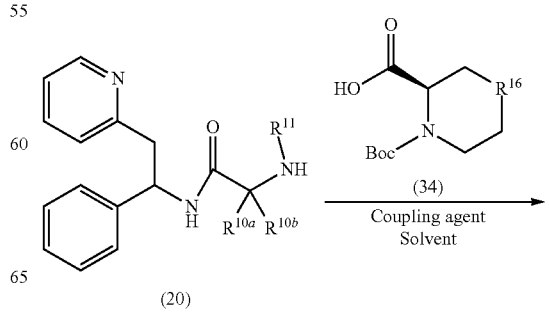

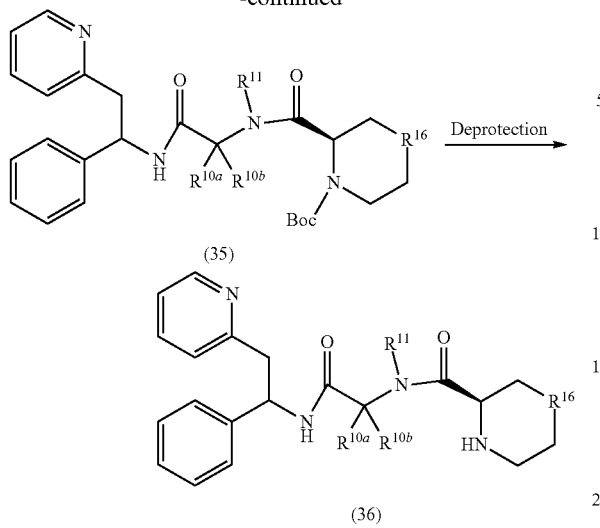

A compound of the formula (20) is reacted with a compound of (34), a known compound or a compound made by known methods, in the presence of a coupling agent such as O-(benzotriazol-1-yl)-N,N,N',N'-tetramethyluronium hexafluorophosphate, N,N'-dicyclohexyl carbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (35). A compound of the formula (35) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (36).

A compound of the formula (20) is reacted with a compound of (37), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (38). A compound of the formula (38) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (39).

A compound of the formula (25) is reacted with a compound of (40), a known compound or a compound made by known methods, in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (41).

Scheme 16

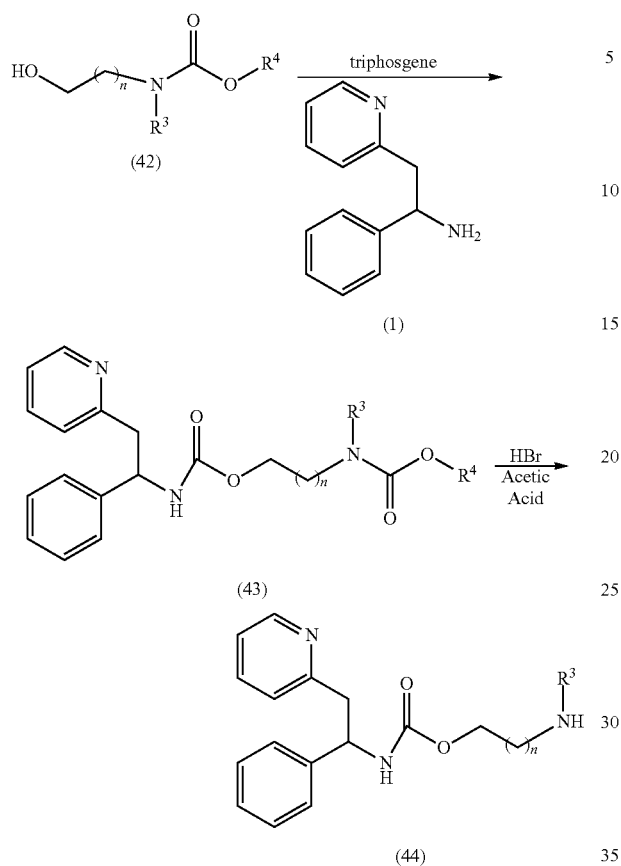

A compound of the formula (42), a known compound or a compound prepared by known methods, is reacted with triphosgene in the presence of a solvent such as N,N-dimethylformamide, 1,4-dioxane, tetrahydrofuran, methylene chloride, chloroform, and the like. The resulting product is then reacted with a compound of the formula (1) in the presence of a base such as triethylamine, diisopropylethylamine, N-methylmorpholine and the like, in the presence of a solvent such as N, N-dimethylformamide, 1,4-dioxane, tetrahydrofuran, methylene chloride and the like, optionally with heating, optionally with microwave irradiation to provide a compound of the formula (43). A compound of the formula (44) is reacted with hydrogen bromide in the presence of acetic acid, optionally in the presence of a solvent such as N, N-dimethylformamide, 1,4-dioxane, tetrahydrofuran, methylene chloride and the like, optionally with heating, optionally with microwave irradiation to provide a compound of the formula (44).

Scheme 17

R²—OH →(triphosgene)

(45)

A compound of the formula (45), a known compound or a compound prepared by known methods, is reacted with triphosgene in the presence of a solvent such as N,N-dimethylformamide. 1,4-dioxane, tetrahydrofuran, methylene chloride, chloroform, and the like to provide a compound of the formula (46). A compound of the formula (46) is reacted with a compound of the formula (1) in the presence of a base such as triethylamine, diisopropylethylamine, N-methylmorpholine, and the like, in the presence of a solvent such as N. N-dimethylformamide, 1,4-dioxane, tetrahydrofuran, methylene chloride and the like, optionally with heating, optionally with microwave irradiation to provide a compound of the formula (43).

Scheme 18

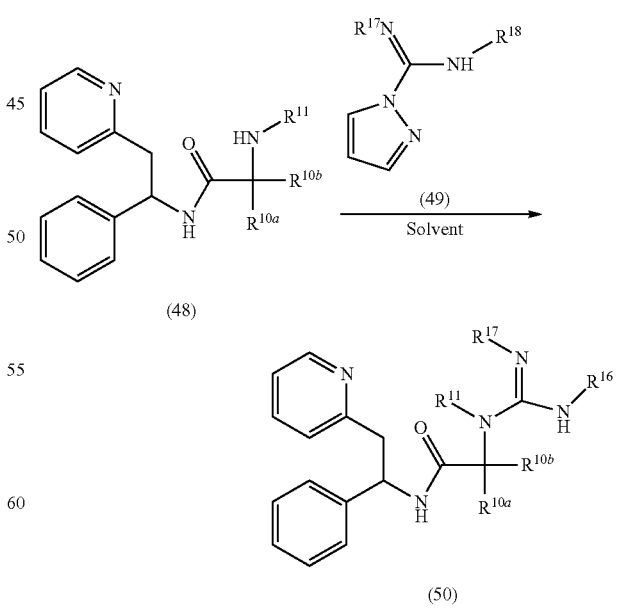

A compound of the formula (48), a known compound or a compound prepared by known methods, is reacted with a compound of the formula (49), a known compound or a compounds prepared using known methods, in the presence of a solvent such as N, N-dimethylformamide, 1,4-dioxane, tetrahydrofuran, methylene chloride and the like, optionally with heating, optionally with microwave irradiation to provide a compound of the formula (50).

Scheme 19

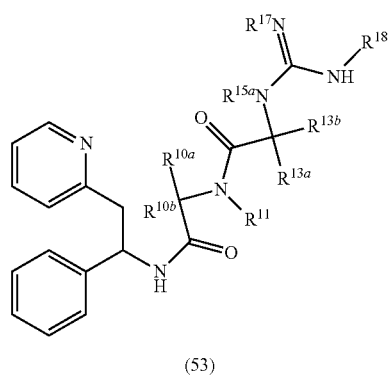

(51)

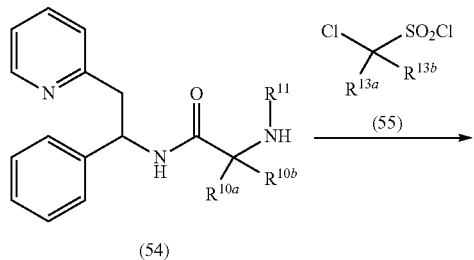

(53)

A compound of the formula (51), a known compound or a compound prepared by known methods, is reacted with a compound of the formula (52), a known compound or a compounds prepared using known methods, in the presence of a solvent such as N, N-dimethylformamide, 1,4-dioxane, tetrahydrofuran, methylene chloride and the like, optionally with heating, optionally with microwave irradiation to provide a compound of the formula (53).

Scheme 20

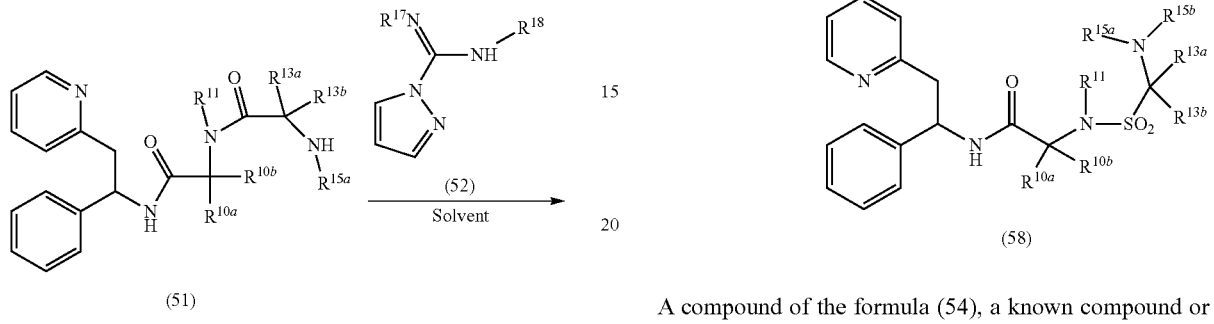

(54)

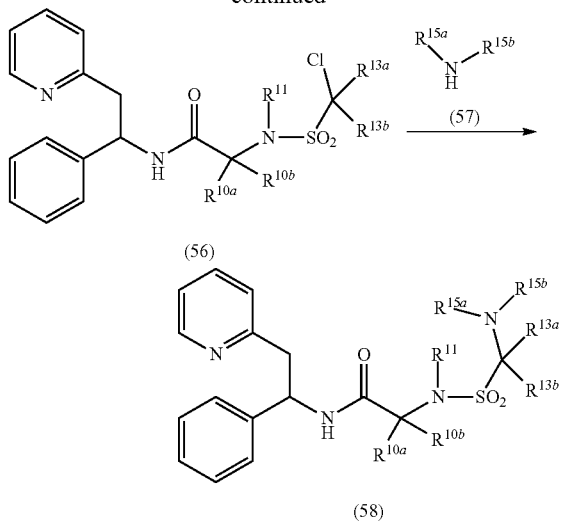

(56)

(58)

A compound of the formula (54), a known compound or a compound prepared by known methods, is reacted with a compound of the formula (55), a known compound or a compounds prepared using known methods, in the presence of a base such as triethylamine, diisopropylethylamine, N-methylmorpholine and the like, in the presence of a solvent such as N, N-dimethylformamide, 1,4-dioxane, tetrahydrofuran, methylene chloride and the like, optionally with heating, optionally with microwave irradiation to provide a compound of the formula (56). A compound of the formula (56) is reacted with a compound of the formula (57), a known compound or a compound prepared by known methods, in the presence of a solvent such as N, N-dimethylformamide, dimethylsulfoxide, 1,4-dioxane, tetrahydrofuran, methylene chloride and the like, optionally with heating, optionally with microwave irradiation to provide a compound of the formula (58).

Scheme 21

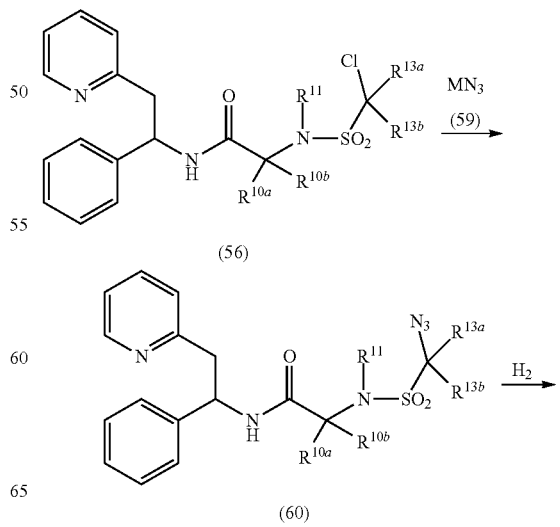

(56)

(60)

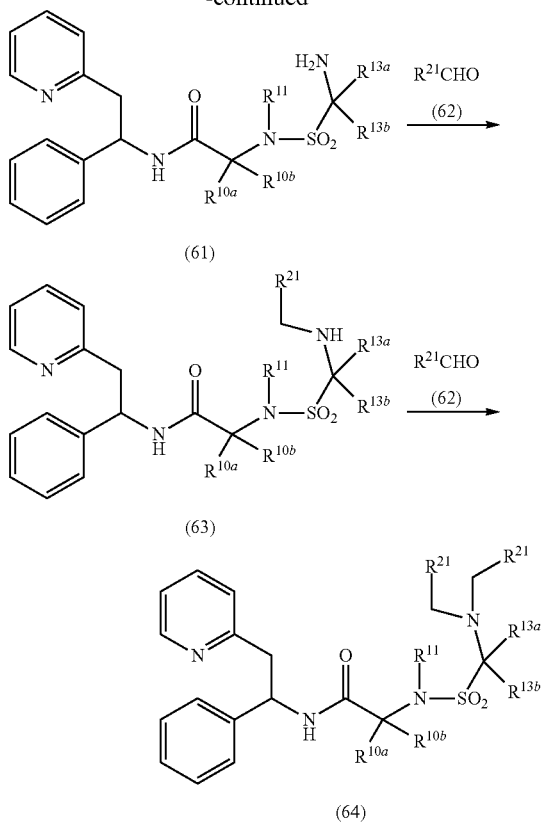

A compound of the formula (56) is reacted with a compound of the formula (59), a known compound or a compound prepared by known methods wherein M is a counter ion such as sodium, potassium, tetrabutyl ammonium, and the like, in the presence of a solvent such as N, N-dimethylformamide, dimethylsulfoxide, 1,4-dioxane, tetrahydrofuran, methylene chloride and the like, optionally with heating, optionally with microwave irradiation to provide a compound of the formula (60). A compound of the formula (60) is reacted with hydrogen in the presence of a catalyst such as palladium on carbon, palladium on barium sulfate, palladium (II) acetate, tetrakis(triphenylphosphine)palladium(0), dichlorobis (triphenylphosphine)palladium(I), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (61). A compound of the formula (61) is reacted with a compound of the formula (62), a known compound or a compound prepared by known methods, in the presence of a hydride source such as sodium borohydride, sodium cyanoborohydride, sodium triacetoxy borohydride, and the like, optionally in the presence of an acid such as acetic acid, trifluoroacetic acid, formic acid, and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, optionally with microwave irradiation to provide a compound of the formula (63). A compound of the formula (63) is reacted with a compound of the formula (62), a known compound or a compound prepared by known methods, in the presence of a hydride source such as sodium borohydride, sodium cyanoborohydride, sodium triacetoxy borohydride, and the like, optionally in the presence of an acid such as acetic acid, trifluoroacetic acid, formic acid, and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, optionally with microwave irradiation to provide a compound of the formula (64).

Schemes 1-21 describe the preparation of compounds containing chiral centers. Those skilled in the art of organic synthesis will recognize that the chemistry described in schemes 1-21 can be applied to prepare the enantiomer of the compounds described employing starting material containing the opposite stereochemistry. In the case of compounds with multiple chiral centers those skilled in the art of organic synthesis will recognize that the chemistry described in schemes 1-21 can be employed to prepare compounds of the disclosure from starting materials containing the desired chirality and each chiral center.

EXAMPLES

The following LC/MS procedure was used for the analysis of all examples listed here: LC/MS data were determined with a Waters Alliance 2695 HPLC/MS (Waters Symmetry C18, 4.6×75 mm, 3.5 µm) with a 2996 diode array detector from 210-400 nm; the solvent system is 5-95% acetonitrile in water (with 0.1% TFA) over nine minutes using a linear gradient, and retention times are in minutes. Mass spectrometry was performed on a Waters ZQ using electrospray in positive mode.

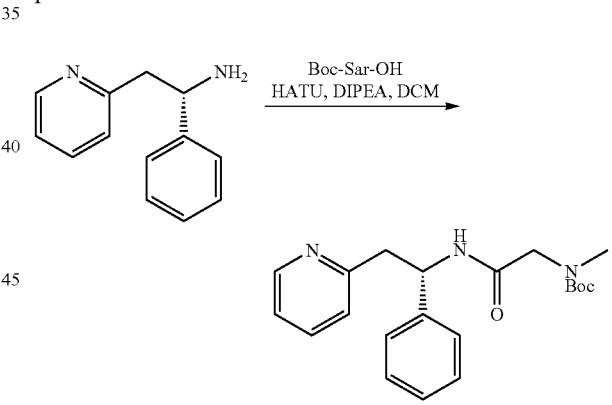

Example 1: Methyl-[(1-phenyl-2-pyridin-2-yl-ethylcarbamoyl)-methyl]-carbamic acid tert-butyl ester. To a solution of Lanicemine (250 mg, 1.26 mmol) in CH$_2$CL (20 mL) were added Boc-Sar-OH (262 mg, 1.39 mmol), (1-[bis(dimethylamino)methylene]-1H-1,2,3-triazolo[4,5-b]pyridinium 3-oxid hexafluorophosphate) (HATU) (575 mg, 1.51 mmol), and N,N-diisopropylethylamine (550 µL, 3.15 mmol) and the mixture was stirred at ambient temperature. After 19 hours the reaction was concentrated and the residue was diluted with ethyl acetate and washed with water, NaHCO$_3$ (sat) and brine. The combined organics were dried over Na$_2$SO$_4$, filtered and concentrate. The crude residues were adsorbed onto SiO$_2$ and purified via normal phase chromatography (50-100% Ethyl acetate/hexane, 20 minute gradient) to afford the title compound (465 mg, quant) as a colorless oil. LCMS: 370.2 m/z [M+H], 392.2 m/z [M+Na].

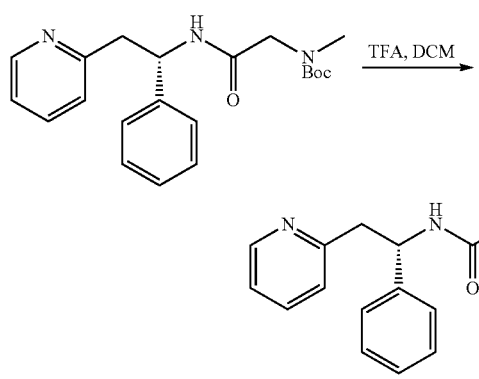

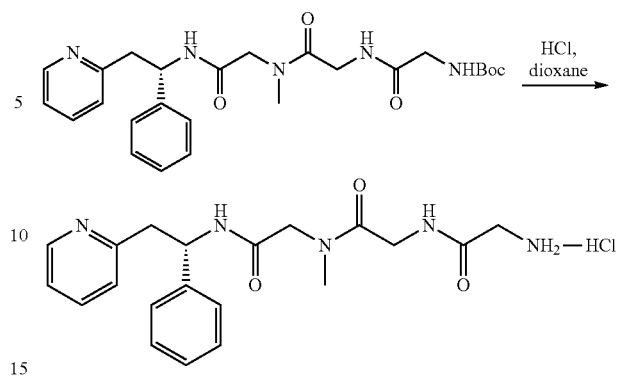

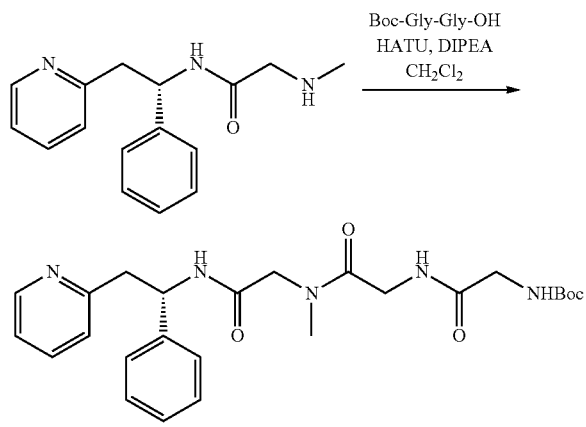

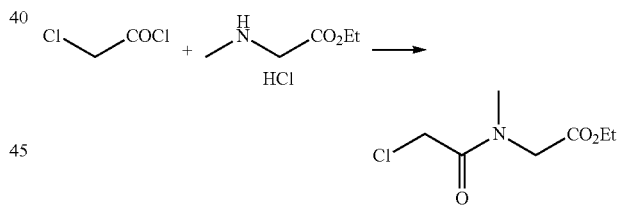

Example 2: 2-Methylamino-N-(1-phenyl-2-pyridin-2-yl-ethyl)-acetamide. To a solution of methyl-[(1-phenyl-2-pyridin-2-yl-ethylcarbamoyl)-methyl]-carbamic acid tert-butyl ester (465 mg, 1.26 mmol) in methylene chloride (10 mL) at 0° C. was added trifluoroacetic acid (2 mL) and the mixture was allowed to warm to ambient temperature. After 2 hours the reaction mixture was concentrated. The residue was diluted with Ethyl acetate and washed with NaHCO$_3$ (sat), and brine. The organics were dried over Na$_2$SO$_4$, filtered and concentrated to afford the title compound (151 mg, 45%) which was used without further purification. LCMS: 270.2 m/z [M+H].

Example 3: {[({Methyl-[(1-phenyl-2-pyridin-2-yl-ethyl-carbamoyl)-methyl]-carbamoyl}-methyl)-carbamoyl]-methyl}-carbamic acid tert-butyl ester. To a solution of 2-Methylamino-N-(1-phenyl-2-pyridin-2-yl-ethyl)-acetamide (75 mg, 0.28 mmol) in methylene chloride (5 mL) at ambient temperature were added Boc-Gly-Gly-OH (72 mg, 0.31 mmol), (1-[Bis(dimethylamino)methylene]-1H-1,2,3-triazolo[4,5-b]pyridinium-3-oxid hexafluoro phosphate) (HATU) (118 mg, 0.31 mmol) and N,N-diisopropylethylamine (146 µL, 0.84 mmol). After 22 hours the reaction mixture was concentrated. The residue was dissolved in Ethyl acetate and washed with water, NaHCO$_3$ (sat), and brine. The organics were dried over Na$_2$SO$_4$, filtered and concentrated. The crude residue was purified via normal phase chromatography (Isco, 2-10% MeOH/CH$_2$Cl$_2$, 20 min ramp) to afford the title compound (74 mg, 55%) as a colorless oil. LCMS: 484.2 m/z [M+H], 506.2 [M+Na].

Example 4: 2-Amino-N-({methyl-[(1-phenyl-2-pyridin-2-yl-ethylcarbamoyl)-methyl]-carbamoyl}-methyl)-acetamide. To a solution of {[({methyl-[(1-phenyl-2-pyridin-2-yl-ethylcarbamoyl)-methyl]-carbamoyl}-methyl)-carbamoyl]-methyl}-carbamic acid tert-butyl ester (74 mg, 0.15 mmol) in dioxane (3 mL) was added 4 N HCl in 1,4-dioxane (114 µL, 0.46 mmol). After 18 hours, the heterogeneous mixture was filtered and the solids were purified via reverse phase chromatography (Gilson, 10-60% MeCN/H$_2$O). Product containing fractions were combined and concentrated. The resultant residue was dissolved in 1,4-dioxane and 4 N HC in dioxane (100 µL) was added. After 1 hour the solids were filtered and observed to melt on the filter paper. The residue was dissolved in water and lyophilized to afford the title compound (38 mg, 59%) as an off-white hygroscopic solid. H NMR (300 MHz, MeOH-d$_4$) δ ppm 8.71-8.81 (m, 1H), 8.44-8.61 (m, 1H), 7.89-8.11 (m, 2H), 7.27-7.53 (m, 5H), 5.39-5.56 (m, 1H), 4.71-5.08 (m, 9H), 3.48-4.27 (m, 9H), 2.84-3.12 (m, 2H), 2.69-2.84 (m, 1H). LCMS: 384.2 m/z [M+H], 406.2 m/z [M+Na].

Example 5: [(2-Chloroacetyl)-methyl-amino]-acetic acid ethyl ester: A mixture of sarcosine ethyl ester hydrochloride (3.0 g, 19 mmol) and N, N-diisopropylethylamine (5.8 g, 45 mmol, 8.1 mil) in methylene chloride (90 ml) was stirred in an ice bath treated with a solution of chloroacetyl chloride (2.0 g, 17 mmol, 1.4 ml) in methylene chloride (10 ml) over 20 minutes. The mixture was stirred 30 minutes then washed with 1N HCl (50 ml). The aqueous layer was extracted with methylene chloride (50 ml) and the combined organic extracts were dried (MgSO$_4$) and evaporated to leave a reddish brown oil (3.3 g, 100%). $^1$HNMR (300 MHz, CDCl$_3$): δ=4.22 (q, J=7.0 Hz, 2H, 3:1 conformational mix), 4.15 (s, 2H), 4.14 and 4.03 (s, 2H, 3:1 conformational mix), 3.19 and 3.03 (s, 3H, 3:1 conformational mix), 1.29 (t, J=7.0 Hz, 3H).

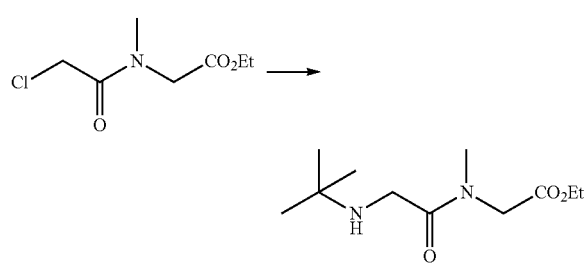

Example 6: [(2-tert-Butylamino-acetyl)-methyl-amino]-acetic acid ethyl ester: A mixture of ethyl chloroacetylsarcosine (3.0 g, 15 mmol) in methylene chloride (30 ml) was treated with t-butylamine (4.4 g, 60 mmol, 6.3 ml) and stirred for 20 hours. The mixture was extracted with 1N HCl (2×50 ml) and the combined acidic layers were neutralized with solid sodium carbonate. The aqueous layer was extracted with ethyl acetate (2×50 ml), combined, washed with brine (25 ml), dried (MgSO4) and evaporated to leave a reddish brown oil (2.4 g, 70%). $^1$HNMR (300 MHz, CDCl$_3$): δ=4.22 and 4.20 (q, J=7.0 Hz, 2H, 3:1 conformational mix), 4.14 and 4.08 (s, 2H, 3:1 conformational mix), 3.47 and 3.34 (s, 2H, 3:1 conformational mix), 3.06 and 3.01 (s, 3H, 3:1 conformational mix), 1.30 (t, J=7.0 Hz, 3H), 1.12 and 1.09 (s, 9H, 3:1 conformational mix).

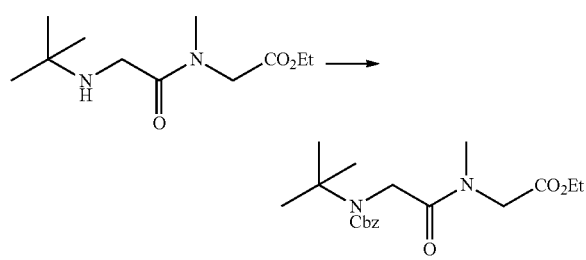

Example 7:1 [2-(Benzyloxycarbonyl-tert-butyl-amino)-acetyl]-methyl-amino)-acetic acid ethyl ester: A solution of t-butylglycylsarcosine ethyl ester (2.3 g, 10 mmol) and N,N-diisopropylethylamine (1.5 g, 12 mmol, 2.2 ml) in methylene chloride (50 ml) was cooled in ice and treated with a solution of benzyl chloroformate (2.1 g, 12 mmol, 1.7 ml) in methylene chloride (10 ml) over 20 minutes. The reaction mixture was allowed to warm to 20° C. over 2 hours and then stirred at this temperature for 20 hours. The mixture was washed with 1N HCl (30 ml), dried (MgSO$_4$) and evaporated. The crude product was purified by chromatography on silica gel eluted with a gradient of ethyl acetate in hexanes (10-50%) to leave 1.5 g (41%) of thick oil. $^1$HNMR (300 MHz, CDCl$_3$): δ=7.32 (m, 5H), 5.12 (s, 2H), 4.25 and 3.95 (s, 2H, 3:1 conformational mix), 4.18 (q, J=7.0 Hz, 21-), 4.10 (s, 2H), 3.02 and 2.98 (s, 3H, 3:1 conformational mix), 1.44 (s, 9H), 1.26 (t, J=7.0 Hz).

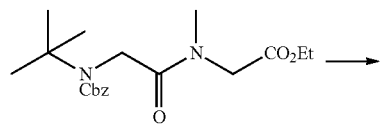

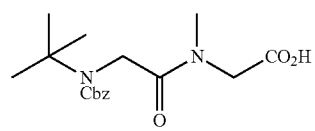

Example 8: {[2-(Benzyloxycarbonyl-tert-butyl-amino)-acetyl]-methyl-amino}-acetic acid: A solution of N-(benzyloxycarbonyl)-N-t-butylglycylsarcosine ethyl ester (1.3 g, 3.6 mmol) in ethanol (40 ml) was treated with 1N sodium hydroxide solution (7.2 ml). The solution stirred for 45 minutes then approximately half of the ethanol was evaporated under reduced pressure. The residue was treated with 1N HC (100 ml) and extracted with methylene chloride (2×50 ml). The combined organic extracts were dried (MgSO$_4$) and evaporated to leave a thick oil (1.2 g, 100%). $^1$HNMR (300 MHz, CDCl$_3$): δ=7.60 (bs, 1H), 7.32 (m, 5H), 5.10 (s, 2H), 4.15 and 3.96 (s, 2H, 3:1 conformational mix), 4.13 (s, 2H), 3.01 and 2.98 (s, 3H, 3:1 conformational mix), 1.41 (s, 9H).

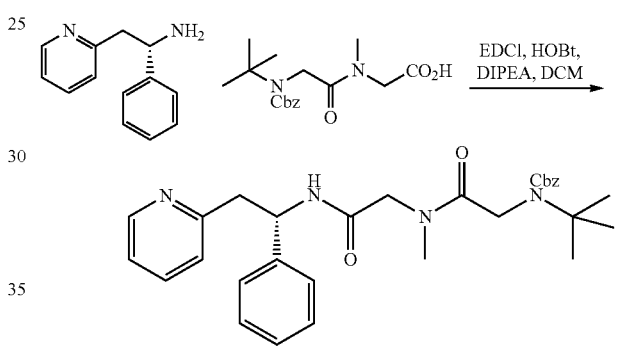

Example 9: tert-Butyl-({methyl-[(1-phenyl-2-pyridin-2-yl-ethylcarbamoyl)-methyl]-carbamoyl}-methyl)-carbamic acid benzyl ester: To a solution of lanicemine (48 mg, 0.24 mmol) in CH$_2$Cl$_2$ (5 mL) were added {[2-(benzyloxycarbonyl-tert-butyl-amino)-acetyl]-methyl-amino}-acetic acid (81 mg, 0.24 mmol), 1-ethyl-3-(3-dimethylaminopropyl)carbodiimide (EDCI) (51 ng, 0.26 mmol), hydroxybenzotriazole (HOBt) (40 mg, 0.26 mmol) and N,N-diisopropylethylamine (62 mg, 0.48 mmol). After 16 hours the reaction mixture was adsorbed directly onto silica gel and purified via normal phase chromatography (5-20% MeOH/CH$_1$Cl$_2$, 20 minute gradient) and the product-containing fractions were combined and concentrated to afford the title compound (130 mg, quant) as a colorless oil. LCMS: 461.1 m/z [M-tBu], 517.3 m/z [M+H], 539.2 [M+Na].

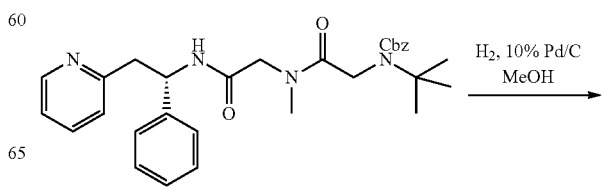

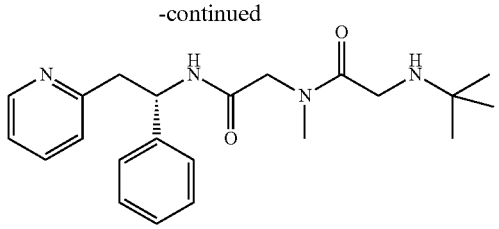

Example 10: 2-tert-Butylamino-N-methyl-N-[(1-phenyl-2-pyridin-2-yl-ethylcarbamoyl)-methyl]-acetamide: To a solution of tert-Butyl-({methyl-[(1-phenyl-2-pyridin-2-yl-ethylcarbamoyl)-methyl]-carbamoyl}-methyl)-carbamic acid benzyl ester (124 mg, 0.24 mmol) in MeOH (10 mL) was added 10% Pd/C (40 mg) and the mixture was placed under a 1 atm of $H_2$. After 18 hours the reaction mixture was filtered through a cartridge filter and concentrated. The residue was dissolved in 1,4-dioxane (5 mL) and 4 N HCl/1,4-dioxane was added. The resultant heterogeneous mixture was stirred for 30 minutes and filtered, and the filter cake was washed with $Et_2O$. The resultant hygroscopic solids were dissolved in water, frozen and lyophilized to afford the title compound (72 mg, 78%) as an off-white solid. $^1$H NMR (300 MHz, DMSO-$d_6$) δ ppm 9.64 (d, J=9.09 Hz, 1H), 9.07 (d, J=9.09 Hz, 1H), 8.60-8.92 (m, 5H), 8.38-8.54 (m, 2H), 7.99-8.20 (m, 2H), 7.81-7.98 (m, 2H), 7.45-7.58 (m, 4H), 7.21-7.41 (m, 6H), 5.28-5.43 (m, 2H), 4.15-4.19 (m, 1H), 3.86-4.07 (m, 6H), 3.36-3.74 (m, 16H), 3.01-3.07 (m, 1H), 2.81-2.96 (m, 4H), 2.54-2.71 (m, 4H), 1.72 (s, 1H), 1.13-1.38 (m, 19H), 0.74-0.97 (m, 1H). LCMS: 327.2 m/z [M-tBu], 383.2 m/z [M+H], 405.1 m/z [M+Na].

FORMULATIONS

The present invention also relates to compositions or formulations which comprise the Lanicemine prodrug agents according to the present invention. In general, the compositions of the present invention comprise an effective amount of one or more Lanicemine prodrug agents and salts thereof according to the present invention which are effective and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally, parenterally or as orally dissolvable tablets ("ODT's") or sublingual preparations, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known prodrug agents. Oral formulations containing a compound disclosed herein can comprise any conventionally used oral form, including tablets, capsules, buccal forms, ODTs or other sublingual formulations, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethyl cellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more Lanicemine prodrugs according to the present invention and one or more excipients; from about 0.01 mg to about 100 mg of one or more Lanicemine prodrugs according to the present invention and one or more excipients; and from about 0.1 mg to about 10 mg of one or more Lanicemine prodrugs according to the present invention; and one or more excipients.

PROCEDURES

The following procedures can be utilized in evaluating and selecting compounds as Lanicemine prodrugs.

Stability in Simulated Gastric Fluid (SGF) and Simulated Intestinal Fluid (SIF). Procedure from Baudy et. al. (J. Med. Chem. 2009, 52, 771-778) are used. The physiological stability of Lanicemine prodrug agent was determined by examining the stability of the compound in SGF, and SIF at 37° C. The compounds were prepared in a 9:1 mixture of the appropriate test component (SGF, SIF and acetonitrile to a final concentration of 0.01 mg/mL The samples were thoroughly mixed and maintained at 37° C. Each sample was injected consecutively onto an Agilent 1100 system (Luna C18, 3 μm, 50 mm×3 mm; 1 mL/min; mobile phase of 0.1% trifluoroacetic acid in water/0.1% trifluoroacetic acid in acetonitrile) after a 3 hour period. The percent remaining of prodrug was calculated by comparing the area of prodrug compound versus Lanicemine generated. The identities of the parent compounds and conversion products were confirmed by LC/MS.

Plasma Stability: Assessment of plasma stability was carried out by individual incubations of Lanicemine prodrug agent in fresh mouse or human control plasma at a concentration of 1 uM for 1 hour at 37° C. After which, the samples were de-proteinized by addition of 2 volumes of acetonitrile containing 0.1% formic acid and internal standard, vortex mixed for 2 minutes and centrifuged at 4000 rpm for 10 minutes to pellet precipitated protein. The resulting supernatant containing the Lanicemine prodrug agent was diluted 5-fold with water containing 0.1% formic acid and submitted to LC-MS/MS analysis. All determinations were done in triplicate. Plasma stability was expressed as percent of control remaining.

Metabolic Stability: In vitro metabolic stability was determined in pooled mouse or human liver microsomes (BD Gentest) at a protein concentration of 0.5 mg/mL in reaction buffer (100 mM $KH_2PO_4$, pH 7.4 and 12 mM $MgCl_2$). Each Lanicemine prodrug agent was added to a final concentration of 1 uM. This mixture was pre-warmed to 37° C. for 10 minutes prior to starting the reaction with the addition of β-Nicotinamide adenine dinucleotide 2'-phosphate reduced (NADPH) to a final concentration of 1 mM. A parallel incubation lacking NADPH served as the control. After incubation for 30 ruin at 37° C., the reactions were quenched by the addition of acetonitrile containing 0.1% formic acid and internal standard, vortex mixed for 2 minutes and centrifuged at 4000 rpm for 10 minutes to pellet the precipitated protein. The resulting supernatant containing the Lanicemine prodrug agent and its potential metabolites was diluted 5-fold with water containing 0.1% formic acid and submitted to LC-MS/MS analysis. Metabolic stability was expressed as percent of control remaining.

LC-MS/MS Analysis: An aliquot from each incubation was analyzed by LC-MS/MS with SRM detection in the positive ionization mode using an ABSciex API 5500 QTrap Mass Spectrometer interfaced via the ABSciex Turbo V IonSpray source (ESI) to an Eksigent ExpressHT LC system. Best peak shape and separation from interfering matrix species was afforded by an Eksigent 3C18-CL-300, 3μ, 50×1 mm column. A fast gradient, from 15 to 85% organic in 2.5 minutes, with run time of 5.0 minutes, and flow rate of 50 uL/min was utilized. Peak areas were integrated using MultiQuant v2.0 software from ABSciex.

RatPharmacokinetic studies of the compounds of the disclosure: The pharmacokinetics of the compound of the disclosure and released Lanicemine were evaluated following either a single intravenous or oral administration of the prodrug to fasted male Sprague-Dawley rats at suggested dose levels (mg/Kg body weight). Blood samples were collected at pre-determined time points including a 0 hour time point and usually between 7 and 8 additional time points not exceeding a 24 hour period. Plasma concentrations of the Lanicemine prodrug agent and Lanicemine were determined by LC-MS/MS and pharmacokinetic parameters were determined using WinNonlin (v6.3).

Plasma samples were extracted and analyzed using the methods described in Plasma S ample Extraction and Analysis. Average plasma concentrations for selected examples and plasma pharmacokinetic parameters are determined. All data are expressed as ng/mL of the free base. Samples that were below the limit of quantification (0.5 ng/mL) are not used in the calculation of averages.

Pharmacokinetic parameters were calculated from the time course of the plasma concentrations. Pharmacokinetic parameters were determined with Phoenix Winnonlin (v6.3) software using a non-compartmental model. The maximum plasma concentration (Cmax) and time to the maximum plasma concentration (Tmax) of the compound of the disclosure were observed from the data. The area under the concentration-time curve (AUC) of the compound of the disclosure was calculated using the trapezoidal formula with calculation to the last quantifiable data point, and to infinity if applicable. Plasma half-life (t½) was calculated from 0.693/slope of the terminal elimination phase. Mean residence time, MRT, was calculated by dividing the area under the moment curve (AUMC) by the AUC. Any samples below the limit of quantitation (0.5 ng/mL) were treated as zero for pharmacokinetic data analysis.

Plasma Sample Extraction and Analysis: Analytical stock solutions (1.00 mg/mL) of the free compound of the disclosure were prepared in DMSO. Standards were prepared in diluted matrix containing 1 part 10% formic acid and 9 parts Sprague-Dawley rat plasma containing sodium heparin as the anticoagulant (pre-diluted with 1 part of 0.5M citric acid and 9 parts whole blood). Working solutions were prepared in 50:50 acetonitrile:water. Working solutions were then added to plasma to make calibration standards to final concentrations of 1000, 500, 100, 50, 10, 5, 1, and 0.5 ng/mL. Standards contained both the Lanicemine prodrug agent and Lanicemine. Standards were treated identically to the study samples.

Sample Extraction: Plasma samples were extracted via acetonitrile precipitation on a Tomtec Quadra 96-Model 320 liquid handling system in a 96-well plate format.

Step 1
1) Standards: Add 10 µL of appropriate working solution to 50 µL of blank matrix in a 96-well plate.
2) Blanks: Add 10 µL 50:50 acetonitrile:water to 50 µL of blank matrix in a 96-well plate.
3) Samples: Add 10 µL 50:50 acetonitrile:water to 50 µL of study sample in a 96-well plate.
4) Cap and mix.

Step 2: Using the Tomtec, add 50 µL of sample to 150 µL of acetonitrile (containing 100 ng/mL propranolol as an internal standard) that has been pre-loaded onto a Sirocco Protein Precipitation plate (Waters Corp.)

Step 3: Using the Tomtec, mix the samples via air aspiration

Step 4: Apply vacuum and collect filtrates into clean polypropylene 96-well plate. Cap for analysis.

HPLC Conditions:
Instrument: Waters Acquity UPLC
Column: Waters Acquity BEH C18, 100×2.1 mm id, 1.7 µm
Mobile Phase Buffer: 40 mM ammonium formate, pH 3.5
Aqueous Reservoir (A): 10% buffer, 90% water
Organic Reservoir (B): 10% buffer, 90% acetonitrile
Gradient Program:

| Time (min) | Grad. Curve | % A | % B |
| --- | --- | --- | --- |
| 0.00 | 6 | 90 | 10 |
| 3.75 | 6 | 0 | 100 |
| 4.00 | 6 | 90 | 10 |
| 5.00 | 6 | 90 | 10 |

Flow Rate: 400 µL/min
Injection Volume: 5 µL
Run Time: 5.0 min
Column Temperature: 40° C.
Sample Temperature: 8° C.

Strong Autosampler Wash: 1:1:1 (v:v:v) water:methanol:isopropanol with 0.2% formic acid
Weak Autosampler Wash: 4 mM ammonium formate
Mass Spectrometer Conditions:
Instrument: PE Sciex API4000
Interface: Electrospray ("Turbo Ion Spray")
Mode: Multiple Reaction Monitoring (MRM)
Gases: CUR 30, CAD 10, GS1 50. GS2 50
Source Temperature: 550° C.
Polarity: positive

What is claimed is:
1. A compound having formula (I):

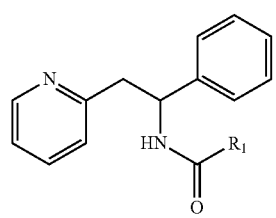

(I)

or a hydrate, a solvate, or a pharmaceutically acceptable salt thereof, wherein:

$R^1$ is selected from the group consisting of $C_1$-$C_6$ fluoroalkyl, $OR^2$, $(CR^{6a}R^{6b})_m NHR^7$,

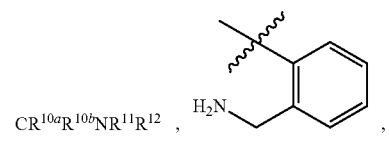

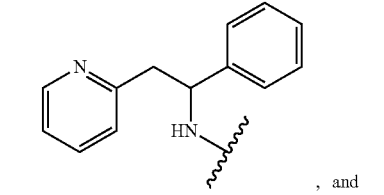
, and

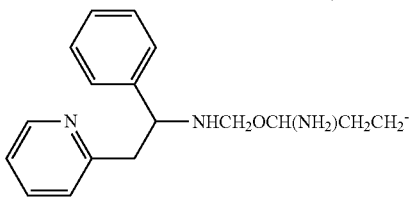
;

$R^2$ is selected from the group consisting of $CH_2(CH_2)_n NR^{3a}R^{3b}$,

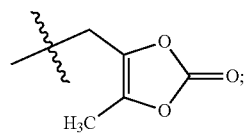
;

$R^{3a}$ and $R^{3b}$ are independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, and $CO_2R^4$;

$R^{3a}$ and $R^{3b}$ cannot both be $C_1$-$C_6$ alkyl;

$R^{3a}$ and $R^{3b}$ are taken together with the atom to which they are bound to form an optionally substituted three to six membered saturated heterocyclic ring consisting of two to five carbon atoms and a member selected from the group consisting of O, $NR^5$, S, and $SO_2$;

n is 1 or 2;

$R^4$ is selected from the group consisting of $C_1$-$C_6$ alkyl, $C_3$-$C_7$ branched alkyl, $C_1$-$C_6$ cycloalkyl, $C_2$-$C_6$ alkenyl, $C_2$-$C_6$ alkynyl, optionally substituted phenyl, and optionally substituted benzyl;

$R^5$ is selected from the group consisting of $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{6a}$ and $R^{6b}$ are at each occurrence independently selected from the group consisting of hydrogen, optionally substituted $C_1$-$C_6$ alkyl, optionally substituted $C_3$-$C_7$ branched alkyl, optionally substituted $C_3$-$C_7$ cycloalkyl, $C_2$-$C_6$ alkenyl, and $C_2$-$C_6$ alkynyl;

$R^{6a}$ and $R^{6b}$ are taken together with the atom to which they are bound to form an optionally substituted 6 membered ring;

m is 1, 2, or 3;

$R^7$ is selected from the group consisting of $COCR^{8a}R^{8b}$ ($NHR^9$),

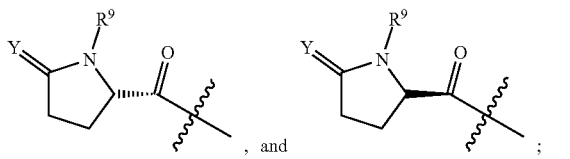
, and ;

$R^{8a}$ and $R^{8b}$ are at each occurrence independently selected from the group consisting of hydrogen, $CH_3$, $CH(CH_3)_2$, $CH_2CH(CH_3)_2$, $CH(CH_3)CH_2CH_3$, $CH_2OH$, $CH(OH)CH_3$, $CH_2Ph$, $CH_2$(4-OH-Ph), $(CH_2)_4NH$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$;

$R^9$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

Y is at each occurrence independently selected from the group consisting of $H_2$ or O;

$R^{10a}$ and $R^{10b}$ are at each occurrence independently selected from the group consisting of hydrogen, $CH_3$, $CH_2CH_3$, $CH(CH_3)_2$, $CH_2CH(CH_3)_2$, $CH(CH_3)CH_2CH_3$, $CH_2OH$, $CH_2OCH_2Ph$, $CH(OH)CH_3$, $CH_2Ph$, $CH_2$(4-OH-Ph), $(CH_2)_4N_2$, $(CH_2)_3NHC(NH_2)NH$, $CH_2$(3-indole), $CH_2$(5-imidazole), $CH_2$(CCH), CH2(cyclohexyl), $CH_2CO_2H$, $CH_2CH_2CO_2H$, $CH_2CONH_2$, and $CH_2CH_2CONH_2$;

$R^{10a}$ and $R^{10b}$ are taken together with the atom to which they are bound to form an optionally substituted three to six membered saturated carbocyclic ring;

$R^{11}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_1$-$C_6$ haloalkyl, and $C_2$-$C_6$ alkynyl;

$R^{11}$ is at each occurrence independently selected from the group consisting of hydrogen, $C_1$-$C_6$ alkyl, $COCR^{13a}R^{13b}NR^{15a}R^{15b}$, $COCR^{13a}R^{13b}OR^{14}$, $S_2CR^{13a}R^{13b}NR^{15a}R^{15b}$ $COCR^{13a}R^{13b}NHSO_2R^{15a}$

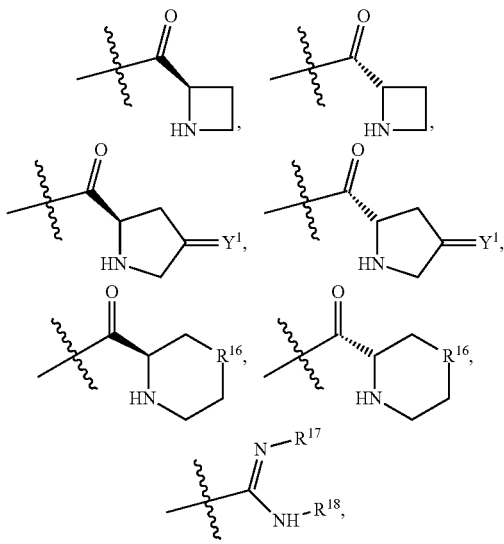

and $(CR^{19a}R^{19b})_qNHR^{20}$, and when $R^{12}$ is hydrogen, $R^{11}$ cannot be hydrogen;

$R^{11}$ and $R^{12}$ are taken together with the atom to which they are bound to form an optionally substituted four to six membered saturated heterocyclic ring containing a nitrogen atom and optionally containing an additional heteroatom from the group consisting of N and O;

$R^{13a}$ and $R^{13b}$ are at each occurrence independently selected from the group consisting of hydrogen, $CH_3$, $CH_2CH_3CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$;

$R^{13a}$ and $R^{13b}$ are taken together with the atom to which they are bound to form an optionally substituted three to six membered saturated carbocyclic ring;

$R^{13a}$ and $R^{13b}$ are taken, together with the atom to which they are bound to form an optionally substituted six membered saturated heterocyclic ring with one O atom within the ring;

$R^{13a}$ and $R^{14}$ are taken together with the atoms to which they are bound to form an optionally substituted four to six membered ring containing one nitrogen atom;

$R^{13a}$ and $R^{15b}$ are taken together with the atoms to which they are bound to form an optionally substituted four to six membered ring containing one nitrogen atom;

$Y^1$ is at each occurrence independently selected from the group consisting of $H_2$, O, and —H/—$OCH_2Ph$;

$R^{14}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{15a}$ and $R^{15b}$ are at each occurrence independently selected from the group consisting of H, $C_1$-$C_6$alkyl, $C_3$-$C_7$ branched alkyl, $C_3$-$C_7$ cycloalkyl, $C_2$-$C_6$ alkenyl, $C_2$-$C_6$ alkynyl $C_1$-$C_6$ fluoroalkyl, $COR^{21}$, $CH_2R^{21}$, $SO_2R^{22}$, an optionally substituted four to six membered saturated heterocyclic ring containing a heteroatom selected from the group consisting of

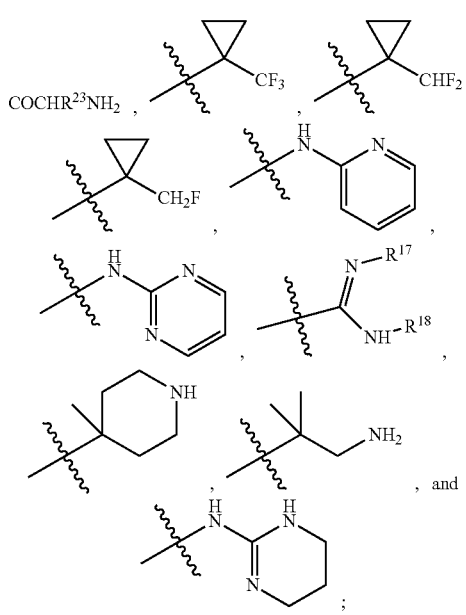

$R^{15a}$ and $R^{15b}$ are taken together with the atom to which they are bound to form an optionally substituted three to six membered saturated heterocyclic ring consisting of two to five carbon atoms and a member selected from the group consisting of O, $NR^5$, S, and $SO_2$;

$R^{16}$ is at each occurrence independently selected from the group consisting of $CH_2$, O, C=O, and NH;

$R^{17}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{18}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{17}$ and $R^{18}$ are taken together with the atoms to which they are bound to form an optionally substituted five or six membered ring containing two nitrogen atoms;

$R^{19a}$ and $R^{18b}$ are at each occurrence independently selected from the group consisting of hydrogen, optionally substituted $C_1$-$C_6$ alkyl, optionally substituted $C_3$-$C_7$ branched alkyl, optionally substituted $C_3$-$C_7$ cycloalkyl, optionally substituted $C_2$-$C_6$ alkenyl, and optionally substituted $C_2$-$C_6$ alkynyl;

$R^{19a}$ and $R^{19b}$ are taken together with the atom to which they are bound to form an optionally substituted 3 to 6 membered carbocyclic ring;

$R^{20}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

q is 1, or 2;

$R^{2'}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, $C_1$-$C_6$ fluoroalkyl, optionally substituted aryl, and optionally substituted heteroaryl;

$R^{22}$ is at each occurrence independently selected from the group consisting of $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted aryl, optionally substituted heteroaryl;

$R^{23}$ is selected from the group consisting of H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$;

$R^{24}$ is at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted aryl, optionally substituted heteroaryl, $COR^{25}$, and $SO_2$—$C_{1-6}$alkyl;

$R^{25}$ is at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted aryl, optionally substituted heteroaryl, $C_3$-$C_6$ alkoxy, and $C_1$-$C_6$ alkylamino, wherein substituted refers to a moiety having one or more hydrogen atoms replaced with a substituent selected from the group consisting of halogen, —CN, —$NO_2$, =O, —$OR^{26}$, —$SR^{26}$, —$N(R^{26})_2$, —$NR^{26}C(O)R^{26}$, —$SO_2R^{26}$, —$SO_2OR^{26}$, —$SO_2N(R^{26})_2$, —$C(O)R^{26}$, —$C(O)OR^{26}$, —$C(O)N(R^{26})_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1 to 10 groups selected independently from the group consisting of halogen, —CN, —$NO_2$, =O, and $R^{26}$, wherein $R^{26}$, at each occurrence, independently is hydrogen, —$OR^{27}$, —$SR^{27}$, —$C(O)R^{27}$, —$C(O)OR^{27}$, —$C(O)N(R^{27})_2$, —$SO_2R^{27}$, —$S(O)_2OR^{27}$, —$N(R^{27})_2$, —$NR^{27}C(O)R^{27}$, $C_{1-6}$ alkyl, $C_{1-6}$ haloalkyl, $C_{2-8}$ alkenyl, $C_{2-8}$ alkynyl, $C_{3-6}$ cycloalkyl aryl, heterocycle, or heteroaryl, or two $R^{26}$ units taken together with the atom(s) to which they are bound form an optionally substituted carbocycle or heterocycle wherein said carbocycle or heterocycle has 3 to 7 ring atoms, wherein $R^{27}$, at each occurrence, independently is hydrogen, $C_{1-6}$ alkyl, $C_{1-6}$ haloalkyl, $C_{2-8}$ alkenyl, $C_{2-8}$ alkynyl, $C_{3-6}$ cycloalkyl, aryl, heterocycle, or heteroaryl, or two $R^{27}$ units taken together with the atom(s) to which they are bound form an optionally substituted carbocycle or heterocycle wherein said carbocycle or heterocycle has 3 to 7 ring atoms.

2. The compound of claim 1 having the formula (II):

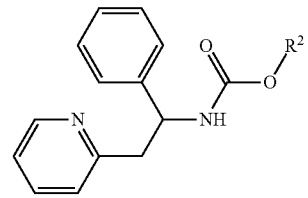

(II)

or a hydrate, a solvate, or a pharmaceutically acceptable salt thereof.

3. The compound of claim 1 having the formula (II):

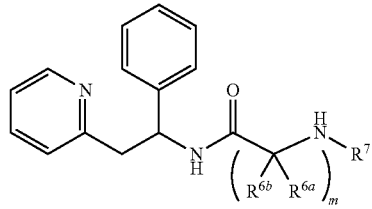

(III)

or a hydrate, a solvate, or a pharmaceutically acceptable salt thereof.

4. The compound of claim 1 having the formula (IV):

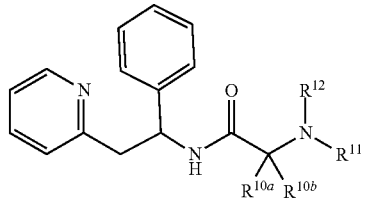

(IV)

or a hydrate, a solvate, or a pharmaceutically acceptable salt thereof.

5. The compound of claim 1 having the formula (V):

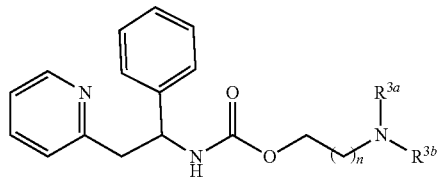

(V)

or a hydrate, a solvate, or a pharmaceutically acceptable salt thereof.

6. The compound of claim 1 having the formula (VI):

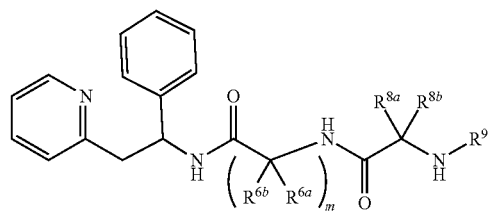

(VI)

or a hydrate, a solvate, or a pharmaceutically acceptable salt thereof.

7. The compound of claim 1 having the formula (VII):

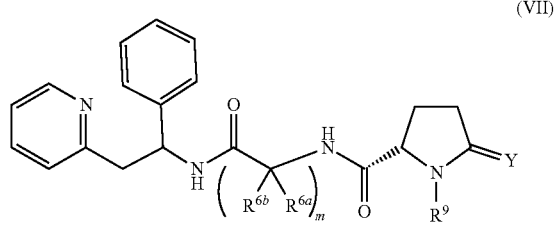

(VII)

or a hydrate, a solvate, or a pharmaceutically acceptable salt thereof.

8. The compound of claim 1 having the formula (VIII):

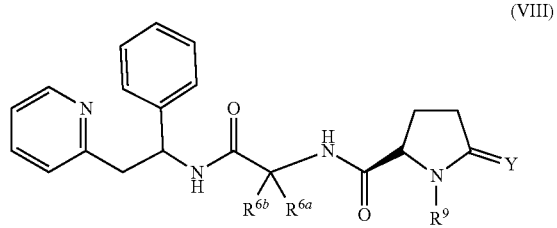

(VIII)

or a hydrate, a solvate, or a pharmaceutically acceptable salt thereof.

9. The compound of claim 1 having the formula (IX):

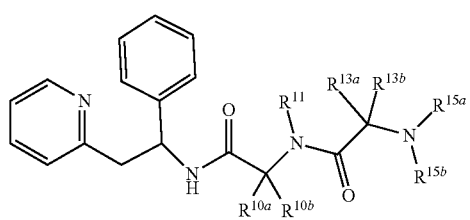

(IX)

or a hydrate, a solvate, or a pharmaceutically acceptable salt thereof.

10. The compound of claim 1 having the formula (X):

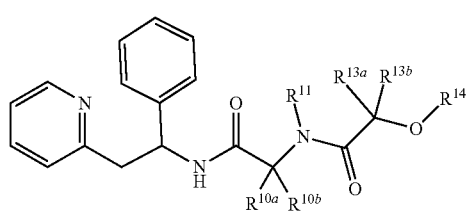

(X)

or a hydrate, a solvate, or a pharmaceutically acceptable salt thereof.

11. The compound of claim 1 having the formula (XI):

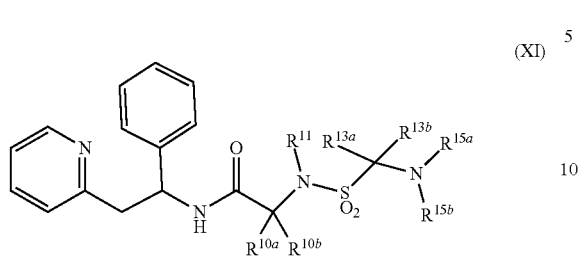

(XI)

or a hydrate, a solvate, or a pharmaceutically acceptable salt thereof.

12. The compound of claim 1 having the formula (XII):

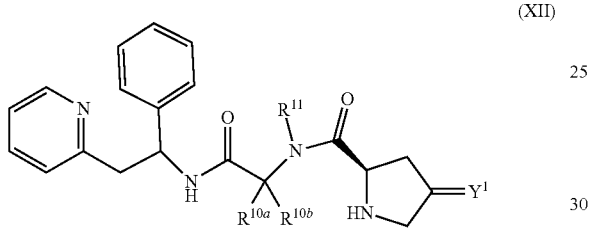

(XII)

or a hydrate, a solvate, or a pharmaceutically acceptable salt thereof.

13. The compound of claim 1 having the formula (XIII):

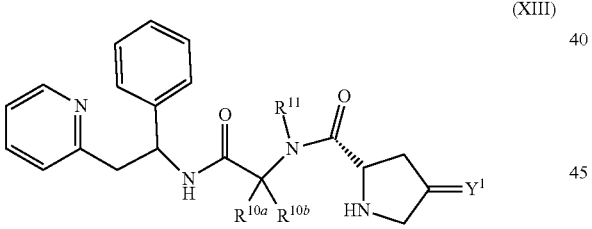

(XIII)

or a hydrate, a solvate, or a pharmaceutically acceptable salt thereof.

14. The compound of claim 1 having the formula (XIV):

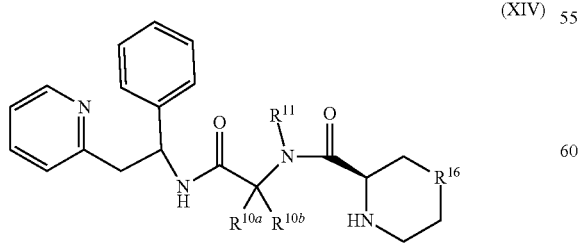

(XIV)

or a hydrate, a solvate, or a pharmaceutically acceptable salt thereof.

15. The compound of claim 1 having the formula (XV):

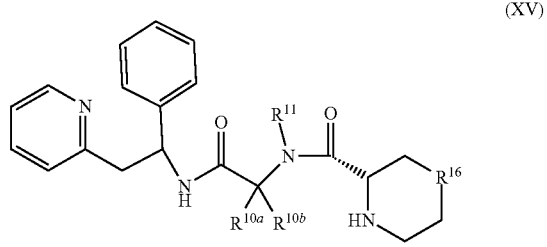

(XV)

or a hydrate, a solvate, or a pharmaceutically acceptable salt thereof.

16. The compound of claim 1 having the formula (XVI):

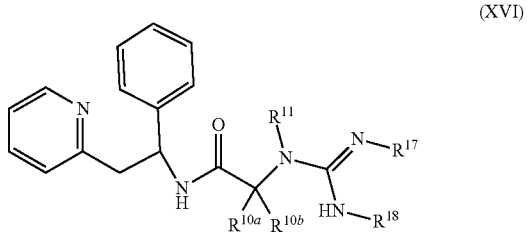

(XVI)

or a hydrate, a solvate, or a pharmaceutically acceptable salt thereof.

17. The compound of claim 1 having the formula (XVII):

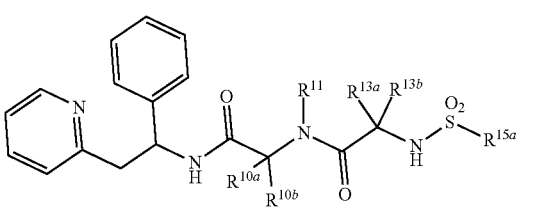

(XVII)

or a hydrate, a solvate, or a pharmaceutically acceptable salt thereof.

18. The compound according to claim 1 that is:
Methyl-[(1-phenyl-2-pyridin-2-yl-ethylcarbamoyl)-methyl]-carbamic acid tert-butyl ester;
2-Methylamino-N-(1-phenyl-2-pyridin-2-yl-ethyl)-acetamide;
2-Methylamino-N-(1-phenyl-2-pyridin-2-yl-ethyl)-acetamide;
{[({Methyl-[(1-phenyl-2-pyridin-2-yl-ethylcarbamoyl)-methyl]-carbamoyl}-methyl)-carbamoyl]-methyl}-carbamic acid tert-butyl ester;
2-Amino-N-({methyl-[(1-phenyl-2-pyridin-2-yl-ethylcarbamoyl)-methyl]-carbamoyl}-methyl)-acetamide;
tert-Butyl-({methyl-[(1-phenyl-2-pyridin-2-yl-ethylcarbamoyl)-methyl]-carbamoyl}-methyl)-carbamic acid benzyl ester;
2-tert-Butylamino-N-methyl-N-[(1-phenyl-2-pyridin-2-yl-ethylcarbamoyl)-methyl]acetamide;
2-(methylamino)-N-(2-oxo-2-((2-(2-pyridyl)-1-(phenyl)ethyl)amino)ethyl)acetamide;
(S)—N-(2-oxo-2-((2-(2-pyridyl)-1-(phenyl)ethyl)amino)ethyl)pyrrolidine-2-carboxamide;

(R)-2-amino-N-(2-oxo-2-((2-(2-pyridyl)-1-(phenyl)ethyl-amino)ethyl)propanamide;
3-amino-N-(2-oxo-2-((2-(2-pyridyl)-1-(phenyl)ethyl)amino)ethyl) propanamide;
1-amino-N-(2-oxo-2-((2-(2-pyridyl)-1-(phenyl)ethyl)amino)ethyl) cyclopropane-1-carboxamide;
(S)—N-(2-oxo-2-((2-(2-pyridyl)-1-(phenyl)ethyl)amino)ethyl)azetidine-2-carboxamide;
2-amino-2-methyl-N-(2-oxo-2-((2-(2-pyridyl)-1-(phenyl)ethyl)amino)ethyl)propanamide;
(S)-2-(methylamino)-N-(2-oxo-2-((2-(2-pyridyl)-1-(phenyl)ethyl)amino)ethyl)propanamide;
(R)-2-(methylamino)-N-(2-oxo-2-((2-(2-pyridyl)-1-(phenyl)ethyl)amino)ethyl)propanamide;
(R)-2-amino-3-hydroxy-N-(2-oxo-2-((2-(4-pyridyl2-pyridyl)-1-(phenyl)ethyl)amino)ethyl)propanamide;
(R)-2-amino-N-(2-oxo-2-((2-(2-pyridyl)-1-(phenyl)ethyl)amino)ethyl)pent-4-ynamide;
(S)-2-amino-N-(2-oxo-2-(2-(2-pyridyl)-1-(phenyl)ethyl)amino)ethyl)pent-4-ynamide;
(R)—N-(2)-oxo-2-((2-(2-pyridyl)-1-(phenyl)ethyl)amino)ethyl)pyrrolidine-2-carboxamide;
1-amino-N-(2-oxo-2-((2-(2-pyridyl)-1-(phenyl)ethyl-amino)ethyl)cyclobutane-1-carboxamide;
(S)-2-amino-N-(2-oxo-2-((2-(2-pyridyl)-1-(phenyl)ethyl)amino)ethyl)pentanamide;
(R)-2-amino-3-methyl-N-(2-oxo-2-((2-(2-pyridyl-1-(phenyl)ethyl)amino)ethyl)butanamide;
(S)-4-oxo-N-(2-oxo-2-(2-(2-pyridyl)-1-(phenyl)ethyl-amino)ethyl)pyrrolidine-2-carboxamide;
(S)—N-(2-oxo-2-((2-(2-pyridyl)-1-(phenyl)ethyl)amino)ethyl)piperidine-2-carboxamide;
(S)—N-(2-oxo-2-((2-(2-pyridyl)-1-(phenyl)ethyl)amino)ethyl)morpholine-3-carboxamide;
(R)—N-(2-oxo-2-((2-(2-pyridyl)-1-(phenyl)ethyl)amino)ethyl)morpholine-3-carboxamide;
(R)-2-amino-4-methyl-N-(2-oxo-2-((2-(2-pyridyl)-1-(phenyl)ethyl)amino)ethyl)pentanamide;
(R)-4-oxo-N-(2-oxo-2-((2-(2-pyridyl)-1-(phenyl)ethyl)amino)ethyl)piperidine-2-carboxamide;
4-amino-N-(2-oxo-2-((2-(2-pyridyl)-1-(phenyl)ethyl)amino)ethyl)tetrahydro-2H-pyran-4-carboxamide;
(R)-2-amino-N1-(2-oxo-2-((2-(2-pyridyl)-1-(phenyl)ethyl)amino)ethyl)pentanediamide;
(R)-2-amino-N-(2-oxo-2-((2-(2-pyridyl)-1-(phenyl)ethyl)amino)ethyl)-3-phenylpropanamide;
(R)-2-amino-3-cyclohexyl-N-(2-oxo-2-((2-(2-pyridyl)-1-(phenyl)ethyl)amino)ethyl)propanamide;
(R)-2-amino-3-(benzyloxy)-N-(2-oxo-2-((2-(2-pyridyl)-1-(phenyl)ethyl)amino)ethyl)propanamide;
(S)-2-amino-3-(benzyloxy)-N-(2-oxo-2-((2-(2-pyridyl)-1-(phenyl)ethyl)amino)ethyl)propanamide;
(R)-2-amino-3-(1H-indol-3-yl)-N-(2-oxo-2-((2-(2-pyridyl)-1-(phenyl)ethyl)amino)ethyl)propanamide;
(2S,4R)-4-(benzyloxy)-N-(2-oxo-2-((2-(2-pyridyl)-1-(phenyl)ethyl)amino)ethyl)pyrrolidine-2-carboxamide;
(S)—N-(2-oxo-2-((2-(2-pyridyl)-1-(phenyl)ethyl)amino)ethyl)piperazine-2-carboxamide;
(R)-2-amino-4-(benzyloxy)-N-(2-oxo-2-((2-(2-pyridyl)-1-(phenyl)ethyl)amino)ethyl)butanamide;
(S)-1-glycyl-N-(2-(2-pyridyl)-1-(phenyl)ethyl)azetidine-2-carboxamide;
(S)-1-(3-aminopropanoyl)-N-(2-(2-pyridyl)-1-(phenyl)ethyl)azetidine-2-carboxamide
(S)-1-(1-(aminomethyl)cyclopropane-1-carbonyl)-N-(2-(2-pyridyl)-(phenyl)ethyl)azetidine-2-carboxamide;
(S)-1-(1-(aminomethyl)cyclopentane-1-carbonyl)-N-(2-(2-pyridyl)-1-(phenyl)ethyl)azetidine-2-carboxamide;
(S)-1-glycyl-N-(2-(2-pyridyl)-1-(phenyl)ethyl)piperidine-2-carboxamide;
(S)-1-(3-aminopropanoyl)-N-(2-(2-pyridyl)-1-(phenyl)ethyl)piperidine-2-carboxamide;
(S)-1-(3-aminopropanoyl)-N-(2-(2-pyridyl)-1-(phenyl)ethyl)piperidine-2-carboxamide;
(R)-1-(methylglycyl)-N-(2-(2-pyridyl)-1-(phenyl)ethyl)piperidine-2-carboxamide;
1-(2-aminoacetamido)-N-(2-(2-pyridyl)-1-(phenyl)ethyl)cyclopropane-1-carboxamide;
1-(2-(methylamino)acetamido)-N-(2-(2-pyridyl)-1-(phenyl)ethyl)cyclopropane-1-carboxamide;
1-(2-aminoacetamido)-N-(2-(2-pyridyl)-1-(phenyl)ethyl)cyclobutane-1-carboxamide;
1-(2-(methylamino)acetamido)-N-(2-(2-pyridyl)-1-(phenyl)ethyl)cyclobutane-1-carboxamide;
1-(3-amino-2,2-dimethylpropanamido)-N-(2-(2-pyridyl)-1-(phenyl)ethyl)cyclobutane-1-carboxamide;
1-(aminomethyl)-N-(1-((2-(2-pyridyl)-1-(phenyl)ethyl)carbamoyl)cyclobutyl) cyclopentane-1-carboxamide;
1-(2-(isopropylamino)acetamido)-N-(2-(2-pyridyl)-1-(phenyl)ethyl)cyclobutane-1-carboxamide;
1-(2-(isopropylamino)acetamido)-N-(2-(2-pyridyl)-1-(phenyl)ethyl)cyclobutane-1-carboxamide;
1-(aminomethyl)-N-(1-((2-(2-pyridyl)-1-(phenyl)ethyl)carbamoyl)cyclobutyl) cyclohexane-1-carboxamide;
(R)-1-(2-aminopropanamido)-N-(2-(2-pyridyl)-1-(phenyl)ethylcyclobutane-1-carboxamide;
(R)-1-(2-amino-3-methylbutanamido)-N-(2-(2-pyridyl)-1-(phenyl)ethyl)cyclobutane-1-carboxamide;
(S)-2-(2-aminoacetamido)-3-phenyl-N-(2-(2-pyridyl)-1-(phenyl)ethyl)propanamide;
(S)-2-(2-(methylamino)acetamido)-3-phenyl-N-(2-(2-pyridyl)-1-(phenyl)ethyl)propanamide;
(S)-2-((R)-2-aminopropanamido)-3-phenyl-N-(2-(2-pyridyl)-1-(phenyl)ethyl)propanamide;
(S)-2-((S)-2-aminopropanamido)-3-phenyl-N-(2-(2-pyridyl)-1-(phenyl)ethyl)propanamide;
(R)-2-amino-3-methyl-N—((S)-1-oxo-3-phenyl-1-((2-(2-pyridyl)-1-(phenyl)ethyl)amino)propan-2-yl)butanamide;
(S)-2-amino-2-methyl-N-(1-oxo-3-phenyl-1-((2-(2-pyridyl)-1-(phenyl)ethyl)amino)propan-2-yl)propanamide;
(S)-1-amino-N-(1-oxo-3-phenyl-1-((2-(2-pyridyl)-1-(phenyl)ethyl)amino)propan-2-yl)cyclopropane-1-carboxamide;
(S)-1-amino-N-(1-oxo-3-phenyl-1-((2-(2-pyridyl)-1-(phenyl)ethyl)amino)propan-2-yl)cyclobutane-1-carboxamide;
1-(3-amino-2,2-dimethylpropanamido)-N-(2-(2-pyridyl)-1-(phenyl)ethyl)cyclobutane-1-carboxamide;
(R)-2-(2-aminopropanamido)-2-methyl-N-(2-(2-pyridyl)-1-(phenyl)ethyl)propanamide;
(S)-2-(2-aminopropanamido)-2-methyl-N-(2-(2-pyridyl)-1-(phenyl)ethyl)propanamide;
2-(2-aminoacetamido)-2-methyl-N-(2-(2-pyridyl)-1-(phenyl)ethyl)propanamide;
(R)-2-amino-N-(2-methyl-1-oxo-1-((2-(2-pyridyl)-1-(phenyl)ethyl)amino)propan-2-yl)-3-phenylpropanamide;
(S)-2-amino-3-(benzyloxy)-N-(2-methyl-1-oxo-1-((2-(2-pyridyl)-1-(phenyl)ethyl)amino)propan-2-yl)propanamide;

1-amino-N-(2-methyl-1-oxo-1-((2-(2-pyridyl)-1-(phenyl)ethyl)amino)propan-2-yl)cyclopropane-1-carboxamide;

1-amino-N-(2-methyl-1-oxo-1-((2-(2-pyridyl)-1-(phenyl)ethyl)amino)propan-2-yl)cyclobutane-1-carboxamide;

2-amino-2-methyl-N-(2-methyl-1-oxo-1-((2-(2-pyridyl)-1-(phenyl)ethyl)amino)propan-2-yl)propanamide;

3-amino-2,2-dimethyl-N-(2-methyl-1-oxo-1-((2-(2-pyridyl)-1-(phenyl)ethyl)amino)propan-2-yl)propanamide;

1-(aminomethyl)-N-(2-methyl-1-oxo-1-((2-(2-pyridyl)-1-(phenyl)ethyl)amino)propan-2-yl)cyclopropane-1-carboxamide;

1-(aminomethyl)-N-(2-methyl-1-oxo-1-((2-(2-pyridyl)-1-(phenyl)ethyl)amino)propan-2-yl)cyclopentane-1-carboxamide;

1-(aminomethyl)-N-(2-methyl-1-oxo-1-((2-(2-pyridyl)-1-(phenyl)ethyl)amino)propan-2-yl)cyclohexane-1-carboxamide;

2-methyl-2-(2-(methylamino)acetamido)-N-(2-(2-pyridyl)-1-(phenyl)ethyl)propanamide;

2-(2-(ethylamino)acetamido)-2-methyl-N-(2-(2-pyridyl)-1-(phenyl)ethyl)propanamide;

2-(2-(isopropylamino)acetamido)-2-methyl-N-(2-(2-pyridyl)-1-(phenyl)ethyl)propanamide;

2-(2-(tert-butylamino)acetamido)-2-methyl-N-(2-(2-pyridyl)-1-(phenyl)ethyl)propanamide;

(S)-2-(2-aminoacetamido)-N-(2-(2-pyridyl)-1-(phenyl)ethyl)propanamide;

(S)-2-amino-N—((S)-1-oxo-1-((2-(2-pyridyl)-1-(phenyl)ethylamino)propan-2-yl)propanamide;

(R)-2-amino-N—((S)-1-oxo-1-((2-(2-pyridyl)-1-(phenyl)ethyl)amino)propan-2-yl)propanamide;

3-Amino-N,2,2-trimethyl-N-(2-oxo-2-((2-(2-pyridyl)-1-(phenyl)ethyl)amino)ethyl)propanamide;

1-(aminomethyl)-N-methyl-N-(2-oxo-2-((2-(2-pyridyl)-1-(phenyl)ethyl)amino)ethyl)cyclopropane-1-carboxamide;

1-(aminomethyl)-N-methyl-N-(2-oxo-2-((2-(2-pyridyl)-1-(phenyl)ethyl)amino)ethyl)cyclopentane-1-carboxamide;

1-(aminomethyl)-N-methyl-N-(2-oxo-2-((2-(2-pyridyl)-1-(phenyl)ethyl)amino)ethyl)cyclohexane-1-carboxamide;

N-methyl-2-(methylamino)-N-(2-oxo-2-((2-(2-pyridyl)-1-(phenyl)ethyl)amino)ethyl)acetamide;

2-(ethylamino)-N-methyl-N-(2-oxo-2-((2-(2-pyridyl)-1-(phenyl)ethyl)amino)ethyl)acetamide;

2-(isopropylamino)-N-methyl-N-(2-oxo-2-((2-(2-pyridyl)-1-(phenyl)ethyl)amino)ethyl)acetamide;

2-(tert-butylamino)-N-methyl-N-(2-oxo-2-((2-(2-pyridyl)-1-(phenyl)ethyl)amino)ethyl)acetamide;

2-(dimethylamino)-N-methyl-N-(2-oxo-2-((2-(2-pyridyl)-1-(phenyl)ethyl) amino)ethyl)acetamide;

2-amino-N-methyl-N-(2-oxo-2-((2-(2-pyridyl)-1-(phenyl)ethyl)amino)ethyl)acetamide;

(S)-2-amino-N-methyl-N-(2-oxo-2-((2-(2-pyridyl)-1-(phenyl)ethyl)amino)ethyl)propanamide;

(R)-2-amino-N-methyl-N-(2-oxo-2-((2-(2-pyridyl)-1-(phenyl)ethyl)amino)ethyl)propanamide;

3-amino-N-methyl-N-(2-oxo-2-((2-(2-pyridyl)-1-(phenyl)ethylamino)ethyl) propanamide;

2-amino-N-ethyl-N-(2-oxo-2-((2-(2-pyridyl)-1-(phenyl)ethylamino) ethyl)acetamide;

2-amino-N-isopropyl-N-(2-oxo-2-((2-(2-pyridyl)-1-(phenyl)ethyl)amino)ethyl)acetamide;

2-(aminomethyl)-N-(2-(2-pyridyl)-1-(phenyl)ethyl)benzamide;

tert-butyl (4-oxo-4-((2-(2-pyridyl)-1-(phenyl)ethyl)amino)butyl)carbamate;

4-amino-N-(2-(2-pyridyl)-1-(phenyl)ethyl)butanamide;

(S)—N-(4-oxo-4-((2-(2-pyridyl)-1-(phenyl)ethyl)amino)butyl) pyrrolidine-2-carboxamide;

(S)-2-amino-4-methyl-N-(4-oxo-4-((2-(2-pyridyl)-1-(phenyl)ethyl)amino)butyl)pentanamide;

4-(2-aminoacetamido)-N-(2-(2-pyridyl)-1-(phenyl)ethyl)butanamide;

(S)-4-(2-aminopropanamido)-N-(2-(2-pyridyl)-1-(phenyl)ethylbutanamide;

(S)-2-amino-3-methyl-N-(4-oxo-4-((2-(2-pyridyl)-1-(phenyl)ethyl)amino)butyl)butanamide;

(S)-5-oxo-N-(4-oxo-4-((2-(2-pyridyl)-1-(phenyl)ethyl)amino)butyl)pyrrolidine-2-carboxamide;

(2S,3S)-2-amino-3-methyl-N-(4-oxo-4-((2-(2-pyridyl)-1-(phenyl)ethyl)amino)butyl)pentanamide;

(S)-4-amino-5-oxo-5-((4-oxo-4-((2-(2-pyridyl)-1-(phenyl)ethylamino)butyl)amino)pentanoic acid;

(S)-2-amino-4-(methylthio)-N-(4-oxo-4-((2-(2-pyridyl)-1-(phenyl)ethyl)amino)butyl)butanamide;

(S)-4-(2-amino-3-phenylpropanamido)-N-(2-(2-pyridyl)-1-(phenyl)ethylbutanamide;

(S)-3-amino-4-oxo-4-((4-oxo-4-((2-(2-pyridyl)-1-(phenyl)ethylamino) butyl)amino) butanoic acid;

(S)-4-amino-5-oxo-5-((4-oxo-4-((2-(2-pyridyl)-1-(phenyl)ethyl)amino)butyl)amino)pentanoic acid;

(S)-4-(2-amino-3-(1H-indol-3-yl)propanamido)-N-(2-(2-pyridyl)-1-(phenyl)ethyl)butanamide;

(S)—N-((1-(2-oxo-2-((2-(2-pyridyl)-1-(phenyl)ethyl)amino)ethyl)cyclohexyl)methyl)pyrrolidine-2-carboxamide;

(S)—N-((1-(2-oxo-2-((2-(2-pyridyl)-1-(phenyl)ethyl)amino)ethyl)cyclohexyl)methyl)pyrrolidine-2-carboxamide;

(S)-2-amino-4-methyl-N-((1-(2-oxo-2-((2-(2-pyridyl)-1-(phenyl)ethyl)amino)ethyl)cyclohexyl)methyl)pentanamide;

(S)-2-amino-3-methyl-N-((1-(2-oxo-2-((2-(2-pyridyl)-1-(phenyl)ethyl)amino)ethyl)cyclohexyl)methyl)butanamide;

2-amino-N-((1-(2-oxo-2-((2-(2-pyridyl)-1-(phenyl)ethyl)amino)ethyl) cyclohexyl)methyl)acetamide;

(S)-2-amino-N-((1-(2-oxo-2-((2-(2-pyridyl)-1-(phenyl)ethyl)amino)ethyl)cyclohexyl)methyl)propanamide;

2-(methylamino)-N-((1-(2-oxo-2-((2-(2-pyridyl)-1-(phenyl)ethyl)amino)ethyl) cyclohexyl)methyl)acetamide;

(R)-2-amino-3-methyl-N-((1-(2-oxo-2-((2-(2-pyridyl)-1-(phenyl)ethyl)amino)ethyl)cyclohexyl)methyl)butanamide;

(S)-5-oxo-N-((1-(2-oxo-2-((2-(2-pyridyl)-1-(phenyl)ethyl)amino)ethyl)cyclohexyl)methyl)pyrrolidine-2-carboxamide;

(S)-2-amino-N1-((1-(2-oxo-2-((2-(2-pyridyl)-1-(phenyl)ethylamino)ethyl)cyclohexyl)methyl)pentanediamide;

(S)-2-amino-4-(methylthio)-N-((1-(2-(2-pyridyl)-1-(phenyl)ethyl)amino)ethyl)cyclohexyl)methyl)butanamide;

(S)-2-amino-N-((1-(2-oxo-2-((2-(2-pyridyl)-1-(phenyl)ethyl)amino)ethyl)cyclohexyl)methyl)-3-phenylpropanamide;

(S)-3-amino-4-oxo-4-(((1-(2-oxo-2-((2-(2-pyridyl)-1-(phenyl)ethyl)amino)ethyl)cyclohexyl)methyl)amino) butanoic acid;

(S)-4-amino-5-oxo-5-(((1-(2-oxo-2-((2-(2-pyridyl)-1-(phenyl)ethyl)amino)ethyl)cyclohexyl)methyl)amino) pentanoic acid;
(S)-2-amino-3-(1H-indol-3-yl)-N-((1-(2-oxo-2-((2-(2-pyridyl)-1-(phenyl)ethyl)amino)ethyl)cyclohexyl) methyl)propanamide;
(R)-2-amino-3-methyl-N-(4-oxo-4-((2-(2-pyridyl)-1-(phenyl)ethyl)amino)butyl)butanamide;
(R)—N-(4-oxo-4-((2-(2-pyridyl)-1-(phenyl)ethyl)amino)butyl)pyrrolidine-2-carboxamide;
(R)-5-oxo-N-(4-oxo-4-((2-(2-pyridyl)-1-(phenyl)ethyl)amino)butyl)pyrrolidine-2-carboxamide;
(R)-2-amino-3-methyl-N-((1-(2-oxo-2-((2-(2-pyridyl)-1-(phenyl)ethyl)amino)ethyl) cyclohexyl)methyl)butanamide;
(S)—N-((1-(2-oxo-2-((2-(2-pyridyl)-1-(phenyl)ethyl)amino)ethyl)cyclohexyl)methyl)pyrrolidine-2-carboxamide;
(R)-5-oxo-N-((1-(2-oxo-2-((2-(2-pyridyl)-1-(phenyl)ethyl)amino)ethyl)cyclohexyl) methyl)pyrrolidine-2-carboxamide;
4-amino-3,3-dimethyl-N-(2-(2-pyridyl)-1-(phenyl)ethyl) butanamide;
(S)-3-(benzyloxy)-2-morpholino-N-(2-(2-pyridyl)-1-(phenyl)ethyl)propanamide;
(S)-3-(benzyloxy)-2-(dimethylamino)-N-(2-(2-pyridyl)-1-(phenyl)ethyl)propanamide;
2-(ethylamino)-N-methyl-N-(2-oxo-2-((2-(2-pyridyl)-1-(phenyl)ethyl)amino)ethyl)acetamide;
2-(isopropylamino)-N-methyl-N-(2-oxo-2-((2-(2-pyridyl)-1-(phenyl)ethyl)amino)ethyl)acetamide;
N-methyl-2-(methylsulfonamido)-N-(2-oxo-2-((2-(2-pyridyl)-1-(phenyl)ethyl)amino)ethyl)acetamide;
2-(tert-butoxy)-N-methyl-N-(2-oxo-2-((2-(2-pyridyl)-1-(phenyl)ethyl)amino)ethyl)acetamide;
N,4,4-trimethyl-N-(2-oxo-2-((2-(2-pyridyl)-1-(phenyl)ethyl)amino)ethyl) pentanamide;
tert-Butyl-(2-(methyl(2-oxo-2-((2-(2-pyridyl)-1-(phenyl)ethylamino)ethyl)amino)-2-oxoethyl)(1-(trifluoromethyl)cyclopropyl)carbamate;
N-methyl-N-(2-oxo-2-((2-(2-pyridyl)-1-(phenyl)ethyl)amino)ethyl)-2-((1-(trifluoromethyl)cyclopropyl)amino)acetamide;
N-methyl-N-(2-oxo-2-((2-(2-pyridyl)-1-(phenyl)ethyl)amino)ethyl)-2-((2,2,2-trifluoroethyl)amino)acetamide hydrochloride;
2-acetamido-N-methyl-N-(2-oxo-2-((2-(2-pyridyl)-1-(phenyl)ethyl)amino)ethyl) acetamide;
N-(2-(methyl(2-oxo-2-((2-(2-pyridyl)-1-(phenyl)ethyl)amino)ethyl)amino)-2-oxoethyl)propionamide;
N-(2-(methyl(2-oxo-2-((2-(2-pyridyl)-1-(phenyl)ethyl)amino)ethyl)amino)-2-oxoethyl)butyramide;
N-(2-(methyl(2-oxo-2-((2-(2-pyridyl)-1-(phenyl)ethyl)amino)ethyl)amino)-2-oxoethyl)isobutyramide;
N-(2-(methyl(2-oxo-2-((2-(2-pyridyl)-1-(phenyl)ethyl)amino)ethyl)amino)-2-oxoethyl)benzamide;
2,2,2-trifluoro-N-(2-(methyl(2-oxo-2-((2-(2-pyridyl)-1-(phenyl)ethyl)amino)ethyl) amino)-2-oxoethyl)acetamide;
N-methyl-N-(2-oxo-2-((2-(2-pyridyl)-1-(phenyl)ethyl)amino)ethyl)-2-((1,1,1-trifluoro-2-methylpropan-2-yl)amino)acetamide;
2-(2-oxopiperazin-1-yl)-N-(2-(2-pyridyl)-1-(phenyl)ethylacetamide;
(S)—N-methyl-N-(2-oxo-2-((2-(2-pyridyl)-1-(phenyl)ethyl)amino)ethyl)piperazine-2-carboxamide;
(R)—N-methyl-N-(2-oxo-2-((2-(2-pyridyl)-1-(phenyl)ethyl)amino)ethyl)piperazine-2-carboxamide;
Benzyl (2-(((2-(2-pyridyl)-1-(phenyl)ethyl)carbamoyl)oxy)ethyl)carbamate;
2-aminoethyl (2-(2-pyridyl)-1-(phenyl)ethyl)carbamate;
Benzyl ethyl(2-(((2-(2-pyridyl)-1-(phenyl)ethyl)carbamoyl)oxy) ethyl)carbamate;
2-(Ethylamino)ethyl (2-(2-pyridyl)-1-(phenyl)ethyl)carbamate;
Benzyl methyl(2-(((2-(2-pyridyl)-1-(phenyl)ethyl)carbamoyl)oxy) ethyl)carbamate;
2-(Methylamino)ethyl (2-(2-pyridyl)-1-(phenyl)ethyl)carbamate;
Benzyl isopropyl(2-(((2-(2-pyridyl)-1-(phenyl)ethyl)carbamoyl)oxy)ethyl)carbamate;
2-(Isopropylamino)ethyl (2-(2-pyridyl)-1-(phenyl)ethyl)carbamate;
(5-methyl-2-oxo-1,3-dioxol-4-yl)methyl (2-(2-pyridyl)-1-(phenyl)ethyl)carbamate;
4-amino-2,2-dimethyl-N-(2-(2-pyridyl)-1-(phenyl)ethyl) butanamide;
(S)-2-amino-N1,N5-bis(2-(2-pyridyl)-1-(phenyl)ethyl) pentanediamide;
2-(dimethylamino)-N-(2-(2-pyridyl)-1-(phenyl)ethyl)acetamide;
1,3-bis(2-(2-pyridyl)-1-(phenyl)ethyl)urea;
or a pharmaceutically acceptable salt thereof.

19. A composition comprising an effective amount of at least one compound according to claim 1 and at least one excipient.

20. The composition according to claim 19, wherein the at least one compound is at least one member selected from the group consisting of:
Methyl-[(1-phenyl-2-pyridin-2-yl-ethylcarbamoyl)-methyl]-carbamic acid tert-butyl ester;
2-Methylamino-N-(1-phenyl-2-pyridin-2-yl-ethyl)-acetamide;
2-Methylamino-N-(1-phenyl-2-pyridin-2-yl-ethyl)-acetamide;
{[({Methyl-[(1-phenyl-2-pyridin-2-yl-ethylcarbamoyl)-methyl]-carbamoyl}-methyl)-carbamoyl]-methyl}-carbamic acid tert-butyl ester;
2-Amino-N-({methyl-[(1-phenyl-2-pyridin-2-yl-ethylcarbamoyl)-methyl]-carbamoyl}-methyl)-acetamide;
tert-Butyl-({methyl-[(1-phenyl-2-pyridin-2-yl-ethylcarbamoyl)-methyl]-carbamoyl}-methyl)-carbamic acid benzyl ester;
2-tert-Butylamino-N-methyl-N-[(1-phenyl-2-pyridin-2-yl-ethylcarbamoyl)-methyl]-acetamide;
2-(methylamino)-N-(2-oxo-2-((2-(2-pyridyl)-1-(phenyl)ethyl)amino)ethyl)acetamide;
(S)—N-(2-oxo-2-((2-(2-pyridyl)-1-(phenyl)ethyl)amino)ethyl)pyrrolidine-2-carboxamide;
(R)-2-amino-N-(2-oxo-2-((2-(2-pyridyl)-1-(phenyl)ethylamino)ethyl)propanamide;
3-amino-N-(2-oxo-2-((2-(2-pyridyl)-1-(phenyl)ethyl)amino)ethyl) propanamide;
1-amino-N-(2-oxo-2-((2-(2-pyridyl)-1-(phenyl)ethyl)amino)ethyl)cyclopropane-1-carboxamide;
(S)—N-(2-oxo-2-((2-(2-pyridyl)-1-(phenyl)ethyl)amino)ethyl)azetidine-2-carboxamide;
2-amino-2-methyl-N-(2-oxo-2-((2-(2-pyridyl)-1-(phenyl)ethyl)amino)ethyl)propanamide;
(S)-2-(methylamino)-N-(2-oxo-2-((2-(2-pyridyl)-1(phenyl)ethyl)amino)ethyl)propanamide;
(R)-2-(methylamino)-N-(2-oxo-2-((2-(2-pyridyl)-1-(phenyl)ethyl)amino)ethyl)propanamide;

(R)-2-amino-3-hydroxy-N-(2-oxo-2-((2-(4-pyridyl2-pyridyl)-1-(phenyl)ethyl)amino)ethyl)propanamide;
(R)-2-amino-N-(2-oxo-2-((2-(2-pyridyl)-1-(phenyl)ethyl)amino)ethyl)pent-4-ynamide;
(S)-2-amino-N-(2-oxo-2-((2-(2-pyridyl)-1-(phenyl)ethyl)amino)ethyl)pent-4-ynamide;
(R)—N-(2-oxo-2-((2-(2-pyridyl)-1-(phenyl)ethyl)amino)ethyl)pyrrolidine-2-carboxamide;
1-amino-N-(2-oxo-2-((2-(2-pyridyl)-1-(phenyl)ethylamino)ethyl)cyclobutane-1-carboxamide;
(S)-2-amino-N-(2-oxo-2-((2-(2-pyridyl)-1-(phenyl)ethyl)amino)ethyl)pentanamide;
(R)-2-amino-3-methyl-N-(2-oxo-2-((2-(2-pyridyl)-1-(phenyl)ethyl)amino)ethyl)butanamide;
(S)-4-oxo-N-(2-oxo-2-(2-(2-pyridyl)-1-(phenyl)ethylamino)ethyl)pyrrolidine-2-carboxamide;
(S)—N-(2-oxo-2-((2-(2-pyridyl)-1-(phenyl)ethyl)amino)ethyl)piperidine-2-carboxamide;
(S)—N-(2-oxo-2-((2-(2-pyridyl)-1-(phenyl)ethyl)amino)ethyl)morpholine-3-carboxamide;
(R)—N-(2-oxo-2-((2-(2-pyridyl)-1-(phenyl)ethyl)amino)ethyl)morpholine-3-carboxamide;
(R)-2-amino-4-methyl-N-(2-oxo-2-((2-(2-pyridyl)-1-(phenyl)ethyl)amino)ethyl)pentanamide;
(R)-4-oxo-N-(2-oxo-2-((2-(2-pyridyl)-1-(phenyl)ethyl)amino)ethyl)piperidine-2-carboxamide;
4-amino-N-(2-oxo-2-((2-(2-pyridyl)-1-(phenyl)ethyl)amino)ethyl)tetrahydro-2H-pyran-4-carboxamide;
(R)-2-amino-N1-(2-oxo-2-((2-(2-pyridyl)-1-(phenyl)ethyl)amino)ethyl)pentanediamide;
(R)-2-amino-N-(2-oxo-2-((2-(2-pyridyl)-1-(phenyl)ethyl)amino)ethyl)-3-phenylpropanamide;
(R)-2-amino-3-cyclohexyl-N-(2-oxo-2-((2-(2-pyridyl)-1-(phenyl)ethyl)amino)ethyl)propanamide;
(R)-2-amino-3-(benzyloxy)-N-(2-oxo-2-((2-(2-pyridyl)-1-(phenyl)ethyl)amino)ethyl)propanamide;
(S)-2-amino-3-(benzyloxy)-N-(2-oxo-2-((2-(2-pyridyl)-1-(phenyl)ethyl)amino)ethyl)propanamide;
(R)-2-amino-3-(1H-indol-3-yl)-N-(2-oxo-2-((2-(2-pyridyl)-1-(phenyl)ethyl)amino)ethyl)propanamide;
(2S,4R)-4-(benzyloxy)-N-(2-oxo-2-((2-(2-pyridyl)-1-(phenyl)ethyl)amino)ethyl)pyrrolidine-2-carboxamide;
(S)—N-(2-oxo-2-((2-(2-pyridyl)-1-(phenyl)ethyl)amino)ethyl)piperazine-2-carboxamide;
(R)-2-amino-4-(benzyloxy)-N-(2-oxo-2-((2-(2-pyridyl)-1-(phenyl)ethyl)amino)ethyl)butanamide;
(S)-1-glycyl-N-(2-(2-pyridyl)-1-(phenyl)ethyl)azetidine-2-carboxamide;
(S)-1-(3-aminopropanoyl)-N-(2-(2-pyridyl)-1-(phenyl)ethyl)azetidine-2-carboxamide;
(S)-1-(1-(aminomethyl)cyclopropane-1-carbonyl)-N-(2-(2-pyridyl)-1-(phenyl)ethyl)azetidine-2-carboxamide;
(S)-1-(1-(aminomethyl)cyclopentane-1-carbonyl)-N-(2-(2-pyridyl)-1-(phenyl)ethyl)azetidine-2-carboxamide;
(S)-1-glycyl-N-(2-(2-pyridyl)-1-(phenyl)ethyl)piperidine-2-carboxamide;
(S)-1-(3-aminopropanoyl)-N-(2-(2-pyridyl)-1-(phenyl)ethyl)piperidine-2-carboxamide;
(S)-1-(3-aminopropanoyl)-N-(2-(2-pyridyl)-1-(phenyl)ethyl)piperidine-2-carboxamide;
(R)-1-(methylglycyl)-N-(2-(2-pyridyl)-1-(phenyl)ethyl)piperidine-2-carboxamide;
1-(2-aminoacetamido)-N-(2-(2-pyridyl)-1-(phenyl)ethyl)cyclopropane-1-carboxamide;
1-(2-(methylamino)acetamido)-N-(2-(2-pyridyl)-1-(phenyl)ethyl)cyclopropane-1-carboxamide;
1-(2-aminoacetamido)-N-(2-(2-pyridyl)-1-(phenyl)ethyl)cyclobutane-1-carboxamide;
1-(2-(methylamino)acetamido)-N-(2-(2-pyridyl)-1-(phenyl)ethyl)cyclobutane-1-carboxamide;
1-(3-amino-2,2-dimethylpropanamido)-N-(2-(2-pyridyl)-1-(phenyl)ethyl)cyclobutane-1-carboxamide;
1-(aminomethyl)-N-(1-((2-(2-pyridyl)-1-(phenyl)ethyl)carbamoyl)cyclobutyl) cyclopentane-1-carboxamide;
1-(2-(isopropylamino)acetamido)-N-(2-(2-pyridyl)-1-(phenyl)ethyl)cyclobutane-1-carboxamide;
1-(2-(isopropylamino)acetamido)-N-(2-(2-pyridyl)-1-(phenyl)ethyl)cyclobutane-1-carboxamide;
1-(aminomethyl)-N-(1-((2-(2-pyridyl)-1-(phenyl)ethyl)carbamoyl)cyclobutyl) cyclohexane-1-carboxamide;
(R)-1-(2-aminopropanamido)-N-(2-(2-pyridyl)-1-(phenyl)ethylcyclobutane-1-carboxamide;
(R)-1-(2-amino-3-methyl butanamido)-N-(2-(2-pyridyl)-1-(phenyl)ethyl)cyclobutane-1-carboxamide;
(S)-2-(2-aminoacetamido)-3-phenyl-N-(2-(2-pyridyl)-1-(phenyl)ethyl)propanamide;
(S)-2-(2-(methylamino)acetamido)-3-phenyl-N-(2-(2-pyridyl)-1-(phenyl)ethyl)propanamide;
(S)-2-((R)-2-aminopropanamido)-3-phenyl-N-(2-(2-pyridyl)-1-(phenyl)ethyl)propanamide;
(S)-2-((S)-2-aminopropanamido)-3-phenyl-N-(2-(2-pyridyl)-1-(phenyl)ethyl)propanamide;
(R)-2-amino-3-methyl-N—((S)-1-oxo-3-phenyl-1-((2-(2-pyridyl)-1-(phenyl)ethyl)amino)propan-2-yl)butanamide;
(S)-2-amino-2-methyl-N-(1-oxo-3-phenyl-1-((2-(2-pyridyl)-1-(phenyl)ethyl)amino)propan-2-yl)propanamide;
(S)-1-amino-N-(1-oxo-3-phenyl-1-((2-(2-pyridyl)-1-(phenyl)ethyl)amino)propan-2-yl)cyclopropane-1-carboxamide;
(S)-1-amino-N-(1-oxo-3-phenyl-1-((2-(2-pyridyl)-1-(phenyl)ethyl)amino)propan-2-yl)cyclobutane-1-carboxamide;
1-(3-amino-2,2-dimethylpropanamido)-N-(2-(2-pyridyl)-1-(phenyl)ethyl)cyclobutane-1-carboxamide;
(R)-2-(2-aminopropanamido)-2-methyl-N-(2-(2-pyridyl)-1-(phenyl)ethyl)propanamide;
(S)-2-(2-aminopropanamido)-2-methyl-N-(2-(2-pyridyl)-1-(phenyl)ethyl)propanamide;
2-(2-aminoacetamido)-2-methyl-N-(2-(2-pyridyl)-1-(phenyl)ethyl)propanamide;
(R)-2-amino-N-(2-methyl-1-oxo-1-((2-(2-pyridyl)-1-(phenyl)ethyl)amino)propan-2-yl)-3-phenylpropanamide;
(S)-2-amino-3-(benzyloxy)-N-(2-methyl-1-oxo-1-((2-(2-pyridyl)-1-(phenyl)ethyl)amino)propan-2-yl)propanamide;
1-amino-N-(2-methyl-1-oxo-1-((2-(2-pyridyl)-1-(phenyl)ethyl)amino)propan-2-yl)cyclopropane-1-carboxamide;
1-amino-N-(2-methyl-1-oxo-1-((2-(2-pyridyl)-1-(phenyl)ethyl)amino)propan-2-yl)cyclobutane-1-carboxamide;
2-amino-2-methyl-N-(2-methyl-1-oxo-1-((2-(2-pyridyl)-1-(phenyl)ethyl)amino)propan-2-yl)propanamide;
3-amino-2,2-dimethyl-N-(2-methyl-1-oxo-1-((2-(2-pyridyl)-1-(phenyl)ethyl)amino)propan-2-yl)propanamide;
1-(aminomethyl)-N-(2-methyl-1-oxo-1-((2-(2-pyridyl)-1-(phenyl)ethyl)amino)propan-2-yl)cyclopropane-1-carboxamide;

1-(aminomethyl)-N-(2-methyl-1-oxo-1-((2-(2-pyridyl)-1-(phenyl)ethyl)amino)propan-2-yl)cyclopentane-1-carboxamide;

1-(aminomethyl)-N-(2-methyl-1-oxo-1-((2-(2-pyridyl)-1-(phenyl)ethyl)amino)propan-2-yl)cyclohexane-1-carboxamide;

2-methyl-2-(2-(methylamino)acetamido)-N-(2-(2-pyridyl)-1-(phenyl)ethyl)propanamide;

2-(2-(ethylamino)acetamido)-2-methyl-N-(2-(2-pyridyl)-1-(phenyl)ethyl)propanamide;

2-(2-(isopropylamino)acetamido)-2-methyl-N-(2-(2-pyridyl)-1-(phenyl)ethyl)propanamide;

2-(2-(tert-butylamino)acetamido)-2-methyl-N-(2-(2-pyridyl)-1-(phenyl)ethyl)propanamide;

(S)-2-(2-aminoacetamido)-N-(2-(2-pyridyl)-1-(phenyl)ethyl)propanamide;

(S)-2-amino-N—((S)-1-oxo-1-((2-(2-pyridyl)-1-(phenyl)ethylamino)propan-2-yl)propanamide;

(R)-2-amino-N—((S)-1-oxo-1-((2-(2-pyridyl)-1-(phenyl)ethyl)amino)propan-2-yl)propanamide;

3-Amino-N,2,2-trimethyl-N-(2-oxo-2-((2-(2-pyridyl)-1-(phenyl)ethyl)amino)ethyl)propanamide;

1-(aminomethyl)-N-methyl-N-(2-oxo-2-((2-(2-pyridyl)-1-(phenyl)ethyl)amino)ethyl)cyclopropane-1-carboxamide;

1-(aminomethyl)-N-methyl-N-(2-oxo-2-((2-(2-pyridyl)-1-(phenyl)ethyl)amino)ethyl)cyclopentane-1-carboxamide;

1-(aminomethyl)-N-methyl-N-(2-oxo-2-((2-(2-pyridyl)-1-(phenyl)ethyl)amino)ethyl)cyclohexane-1-carboxamide;

N-methyl-2-(methylamino)-N-(2-oxo-2-((2-(2-pyridyl)-1-(phenyl)ethyl)amino)ethyl)acetamide;

2-(ethylamino)-N-methyl-N-(2-oxo-2-((2-(2-pyridyl)-1-(phenyl)ethyl)amino)ethyl)acetamide;

2-(isopropylamino)-N-methyl-N-(2-oxo-2-((2-(2-pyridyl)-1-(phenyl)ethyl)amino)ethyl)acetamide;

2-(tert-butylamino)-N-methyl-N-(2-oxo-2-((2-(2-pyridyl)-1-(phenyl)ethyl)amino)ethyl)acetamide;

2-(dimethylamino)-N-methyl-N-(2-oxo-2-((2-(2-pyridyl)-1-(phenyl)ethyl) amino)ethyl)acetamide;

2-amino-N-methyl-N-(2-oxo-2-((2-(2-pyridyl)-1-(phenyl)ethyl)amino) ethyl)acetamide;

(S)-2-amino-N-methyl-N-(2-oxo-2-((2-(2-pyridyl)-1-(phenyl)ethyl)amino)ethyl)propanamide;

(R)-2-amino-N-methyl-N-(2-oxo-2-((2-(2-pyridyl)-1-(phenyl)ethyl)amino)ethyl)propanamide;

3-amino-N-methyl-N-(2-oxo-2-((2-(2-pyridyl)-1-(phenylethylamino)ethyl) propanamide;

2-amino-N-ethyl-N-(2-oxo-2-((2-(2-pyridyl)-1-(phenyl)ethylamino) ethyl)acetamide;

2-amino-N-isopropyl-N-(2-oxo-2-((2-(2-pyridyl)-1-(phenyl)ethyl)amino)ethyl)acetamide;

2-(aminomethyl)-N-(2-(2-pyridyl)-1-(phenyl)ethyl)benzamide;

tert-butyl (4-oxo-4-((2-(2-pyridyl)-1-(phenyl)ethyl) amino)butyl)carbamate;

4-amino-N-(2-(2-pyridyl)-1-(phenyl)ethyl)butanamide;

(S)—N-(4-oxo-4-((2-(2-pyridyl)-1-(phenyl)ethyl)amino) butyl) pyrrolidine-2-carboxamide;

(S)-2-amino-4-methyl-N-(4-oxo-4-((2-(2-pyridyl)-1-(phenyl)ethyl)amino)butyl)pentanamide;

4-(2-aminoacetamido)-N-(2-(2-pyridyl)-1-(phenyl)ethyl)butanamide;

(S)-4-(2-aminopropanamido)-N-(2-(2-pyridyl)-1-(phenyl)ethylbutanamide;

(S)-2-amino-3-methyl-N-(4-oxo-4-((2-(2-pyridyl)-1-(phenyl)ethyl)amino)butyl)butanamide;

(S)-5-oxo-N-(4-oxo-4-((2-(2-pyridyl)-1-(phenyl)ethyl)amino)butyl)pyrrolidine-2-carboxamide;

(2S,3S)-2-amino-3-methyl-N-(4-oxo-4-((2-(2-pyridyl)-1-(phenyl)ethyl)amino)butyl)pentanamide;

(S)-4-amino-5-oxo-5-((4-oxo-4-((2-(2-pyridyl)-1-(phenyl)ethylamino)butyl)amino)pentanoic acid;

(S)-2-amino-4-(methylthio)-N-(4-oxo-4-((2-(2-pyridyl)-1-(phenyl)ethyl)amino)butyl)butanamide;

(S)-4-(2-amino-3-phenylpropanamido)-N-(2-(2-pyridyl)-1-(phenyl)ethylbutanamide;

(S)-3-amino-4-oxo-4-((4-oxo-4-((2-(2-pyridyl)-1-(phenylethylamino) butyl)amino) butanoic acid;

(S)-4-amino-5-oxo-5-((4-oxo-4-((2-(2-pyridyl)-1-(phenyl)ethyl)amino)butyl)amino)pentanoic acid;

(S)-4-(2-amino-3-(1H-indol-3-yl)propanamido)-N-(2-(2-pyridyl)-1-(phenyl)ethyl)butanamide;

(S)—N-((1-(2-oxo-2-((2-(2-pyridyl)-1-(phenyl)ethyl)amino)ethyl)cyclohexyl)methyl)pyrrolidine-2-carboxamide;

(S)—N-((1-(2-oxo-2-((2-(2-pyridyl)-1-(phenyl)ethyl)amino)ethyl)cyclohexyl)methyl)pyrrolidine-2-carboxamide;

(S)-2-amino-4-methyl-N-((1-(2-oxo-2-((2-(2-pyridyl)-1-(phenyl)ethyl) amino)ethyl)cyclohexyl)ethyl)pentanamide;

(S)-2-amino-3-methyl-N-((1-(2-oxo-2-((2-(2-pyridyl)-1-(phenyl)ethyl)amino)ethyl)cyclohexyl)methyl)butanamide;

2-amino-N-((1-(2-oxo-2-((2-(2-pyridyl)-1-(phenyl)ethyl)amino)ethyl) cyclohexyl)methyl)acetamide;

(S)-2-amino-N-((1-(2-oxo-2-((2-(2-pyridyl)-1-(phenyl)ethyl)amino)ethyl)cyclohexyl)methyl)propanamide;

2-(methylamino)-N-((1-(2-oxo-2-((2-(2-pyridyl)-1-(phenyl)ethyl)amino)ethyl) cyclohexyl)methyl)acetamide;

(R)-2-amino-3-methyl-N-((1-(2-oxo-2-((2-(2-pyridyl)-1-(phenyl)ethyl)amino)ethyl)cyclohexyl)methyl)butanamide;

(S)-5-oxo-N-((1-(2-oxo-2-((2-(2-pyridyl)-1-(phenyl)ethyl)amino)ethyl)cyclohexyl)methyl)pyrrolidine-2-carboxamide;

(S)-2-amino-N1-((1-(2-oxo-2-((2-(2-pyridyl)-1-(phenyl)ethylamino)ethyl)cyclohexyl)methyl)pentanediamide;

(S)-2-amino-4-(methylthio)-N-((1-(2-oxo-2-((2-(2-pyridyl)-1-(phenyl)ethyl)amino)ethyl)cyclohexyl)methyl)butanamide;

(S)-2-amino-N-((1-(2-oxo-2-((2-(2-pyridyl)-1-(phenyl)ethyl)amino)ethyl)cyclohexyl)methyl)-3-phenylpropanamide;

(S)-3-amino-4-oxo-4-(((1-(2-oxo-2-((2-(2-pyridyl)-1-(phenyl)ethyl)amino)ethyl)cyclohexyl)methyl)amino) butanoic acid;

(S)-4-amino-5-oxo-5-(((1-(2-oxo-2-((2-(2-pyridyl)-1-(phenyl)ethyl)amino)ethyl)cyclohexyl)methyl)amino) pentanoic acid;

(S)-2-amino-3-(1H-indol-3-yl)-N-((1-(2-oxo-2-((2-(2-pyridyl)-1-(phenyl)ethyl)amino)ethyl)cyclohexyl) methyl)propanamide;

(R)-2-amino-3-methyl-N-(4-oxo-4-((2-(2-pyridyl)-1-(phenyl)ethyl)amino)butyl)butanamide;

(R)—N-(4-oxo-4-((2-(2-pyridyl)-1-(phenyl)ethyl)amino) butyl)pyrrolidine-2-carboxamide;

(R)-5-oxo-N-(4-oxo-4-((2-(2-pyridyl)-1-(phenyl)ethyl) amino)butyl)pyrrolidine-2-carboxamide;

(R)-2-amino-3-methyl-N-((1-(2-oxo-2-((2-(2-pyridyl)-1-(phenyl)ethyl)amino)ethyl) cyclohexyl)methyl)butanamide;
(S)—N-((1-(2-oxo-2-((2-(2-pyridyl)-1-(phenyl)ethyl)amino)ethyl)cyclohexyl)methyl)pyrrolidine-2-carboxamide;
(R)-5-oxo-N-((1-(2-oxo-2-((2-(2-pyridyl)-1-(phenyl)ethyl)amino)ethyl)cyclohexyl) methyl)pyrrolidine-2-carboxamide;
4-amino-3,3-di methyl-N-(2-(2-pyridyl)-1-(phenyl)ethyl) butanamide;
(S)-3-(benzyloxy)-2-morpholino-N-(2-(2-pyridyl)-1-(phenyl)ethyl)propanamide;
(S)-3-(benzyloxy)-2-(dimethylamino)-N-(2-(2-pyridyl)-1-(phenyl)ethyl)propanamide;
2-(ethylamino)-N-methyl-N-(2-oxo-2-((2-(2-pyridyl)-1-(phenyl)ethyl)amino)ethyl)acetamide;
2-(isopropyl amino)-N-methyl-N-(2-oxo-2-((2-(2-pyridyl)-1-(phenyl)ethyl)amino)ethyl)acetamide;
N-methyl-2-(methylsulfonamido)-N-(2-oxo-2-((2-(2-pyridyl)-1-(phenylethyl)amino)ethyl)acetamide;
2-(tert-butoxy)-N-methyl-N-(2-oxo-2-((2-(2-pyridyl)-1-(phenyl)ethyl)amino)ethyl)acetamide;
N,4,4-trimethyl-N-(2-oxo-2-((2-(2-pyridyl)-1-(phenyl)ethyl)amino)ethyl) pentanamide;
tert-Butyl-(2-(methyl(2-oxo-2-((2-(2-pyridyl)-1-(phenyl)ethylamino)ethyl)amino)-2-oxoethyl)(1-(trifluoromethyl)cyclopropyl)carbamate;
N-methyl-N-(2-oxo-2-((2-(2-pyridyl)-1-(phenyl)ethyl)amino)ethyl)-2-((1-(trifluoromethyl)cyclopropyl)amino)acetamide;
N-methyl-N-(2-oxo-2-((2-(2-pyridyl)-1-(phenyl)ethyl)amino)ethyl)-2-((2,2,2-trifluoroethyl)amino)acetamide hydrochloride;
2-acetamido-N-methyl-N-(2-oxo-2-((2-(2-pyridyl)-1-(phenyl)ethyl)amino)ethyl) acetamide;
N-(2-(methyl(2-oxo-2-((2-(2-pyridyl)-1-(phenyl)ethyl)amino)ethyl)amino)-2-oxoethyl)propionamide;
N-(2-(methyl(2-oxo-2-((2-(2-pyridyl)-1-(phenyl)ethyl)amino)ethyl)amino)-2-oxoethyl)butyramide;
N-(2-(methyl(2-oxo-2-((2-(2-pyridyl)-1-(phenyl)ethyl)amino)ethyl)amino)-2-oxoethyl)isobutyramide;
N-(2-(methyl(2-oxo-2-((2-(2-pyridyl)-1-(phenyl)ethyl)amino)ethyl)amino)-2-oxoethyl)benzamide;
2,2,2-trifluoro-N-(2-(methyl(2-oxo-2-((2-(2-pyridyl)-1-(phenyl)ethyl)amino)ethyl) amino)-2-oxoethyl)acetamide;
N-methyl-N-(2-oxo-2-((2-(2-pyridyl)-1-(phenyl)ethyl)amino)ethyl)-2-((1,1,1-trifluoro-2-methylpropan-2-yl)amino)acetamide;
2-(2-oxopiperazin-11-yl)-N-(2-(2-pyridyl)-1-(phenyl)ethylacetamide;
(S)—N-methyl-N-(2-oxo-2-((2-(2-pyridyl)-1-(phenyl)ethyl)amino)ethyl)piperazine-2-carboxamide;
(R)—N-methyl-N-(2-oxo-2-((2-(2-pyridyl)-1-(phenyl)ethyl)amino)ethyl)piperazine-2-carboxamide;
Benzyl (2-(((2-(2-pyridyl)-1-(phenyl)ethyl)carbamoyl)oxy)ethyl)carbamate;
2-aminoethyl (2-(2-pyridyl)-1-(phenyl)ethyl)carbamate;
Benzyl ethyl(2-(((2-(2-pyridyl)-1-(phenyl)ethyl)carbamoyl)oxy) ethyl)carbamate;
2-(Ethylamino)ethyl (2-(2-pyridyl)-1-(phenyl)ethyl)carbamate;
Benzyl methyl(2-(((2-(2-pyridyl)-1-(phenyl)ethyl)carbamoyl)oxy) ethyl)carbamate;
2-(Methylamino)ethyl (2-(2-pyridyl)-1-(phenyl)ethyl) carbamate;
Benzyl isopropyl(2-(((2-(2-pyridyl)-1-(phenyl)ethyl)carbamoyl)oxy)ethyl)carbamate;
2-(Isopropylamino)ethyl (2-(2-pyridyl)-1-(phenyl)ethyl) carbamate;
(5-methyl-2-oxo-1,3-dioxol-4-yl)methyl (2-(2-pyridyl)-1-(phenyl)ethyl)carbamate;
4-amino-2,2-dimethyl-N-(2-(2-pyridyl)-1-(phenyl)ethyl) butanamide;
(S)-2-amino-N1,N5-bis(2-(2-pyridyl)-1-(phenyl)ethyl) pentanediamide;
2-(dimethylamino)-N-(2-(2-pyridyl)-1-(phenyl)ethyl)acetamide;
1,3-bis(2-(2-pyridyl)-1-(phenyl)ethyl)urea;
or a pharmaceutically acceptable salt thereof.

21. A method for treating depression and depressive disorders, said method comprising administering to a subject an effective amount of at least one compound according to claim 1.

22. The method of claim 21, wherein the at least one compound is administered in a composition further comprising at least one excipient.

23. A method for treating major depressive disorder, said method comprising administering to a subject an effective amount of at least one compound according to claim 1.

24. The method of claim 23, wherein the at least one compound is administered in a composition further comprising at least one excipient.

25. A method for treating or pain, said method comprising administering to a subject an effective amount of at least one compound according to claim 1.

26. The method of claim 25, wherein the at least one compound is administered in a composition further comprising at least one excipient.

27. A method for treating neuropathic pain, said method comprising administering to a subject an effective amount of at least one compound according to claim 1.

28. The method of claim 27, wherein the at least one compound is administered in a composition further comprising at least one excipient.

29. A method for treating diseases and conditions associated with dysregulation of NMDA receptor activity, said method comprising administering to a subject an effective amount of at least one compound according to claim 1.

30. The method of claim 29, wherein the at least one compound is administered in a composition further comprising at least one excipient.

31. The method of claim 29 wherein the diseases and conditions associated with dysregulation of NMDA receptor activity is selected from the group consisting of Rett Syndrome, suicidal ideation, bipolar disorder, bipolar depression, obsessive compulsive disorder, sarin gas poisoning, and status epilepticus.

32. The method of claim 30 wherein the diseases and conditions associated with dysregulation of NMDA receptor activity is selected from the group consisting of Rett Syndrome, suicidal ideation, bipolar disorder, bipolar depression, obsessive compulsive disorder, sarin gas poisoning, and status epilepticus.

* * * * *